(12) United States Patent
Olopade

(10) Patent No.: US 6,870,037 B1
(45) Date of Patent: *Mar. 22, 2005

(54) METHYLTHIOADENOSINE PHOSPHORYLASE COMPOSITIONS AND METHODS OF USE IN THE DIAGNOSIS AND TREATMENT OF PROLIFERATIVE DISORDERS

(75) Inventor: Olufunmilayo I. Olopade, Chicago, IL (US)

(73) Assignee: Arch Development Corporation, Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/674,311

(22) Filed: Jul. 1, 1996

Related U.S. Application Data
(60) Provisional application No. 60/000,831, filed on Jul. 2, 1995.

(51) Int. Cl.[7] .......................... C07H 21/04; C12Q 1/68
(52) U.S. Cl. ......................... 536/23.1; 530/350; 435/6; 435/7.1
(58) Field of Search ........................... 536/23.1; 435/6, 435/7.1, 252.3, 810; 530/350

(56) References Cited
PUBLICATIONS

Arap, Nishikawa, Furnari, Cavenee, and Huang, "Replacement of the p16/CDKN2 Gene Suppresses Human Glioma Cell Growth," *Cancer Research*, 55:1351–1354, Mar., 1995.

Bohlander, Dreyling, Hagos, Sveen, Olopade, and Diaz, "Mapping a Putative Tumor Suppressor Gene on Chromosome 9 Bands p21–p22 with Microdissection Probes," *Genomics*, 24:211–217, 1994.

Bohlander, Espinosa III, Le Beau, Rowley, and Diaz, "A Method for the Rapid Sequence–Independent Amplification of Microdissected Chromosomal Material," *Genomics*, 13:1322–1324, 1992.

Chen, Zhang, and Savarese, "Gene Deletion Chemoselectivity: Codeletion of the Genes for p16$^{INK4}$, Methylthioadenosine Phosphorylase, and the α– and β–Interferons in Human Pancreatic Cell Carcinoma Lines and Its Implications for Chemotherapy," *Cancer Research*, 56:1083–1090, Mar., 1996.

Cheng, Jhanwar, Klein, Bell, Lee, Altomare, Nobori, Olopade, Buckler, and Testa, "p16 Alterations and Deletion Mapping of 9p21–p22 in Malignant Mesothelioma," *Cancer Research*, 54:5547–5551, Nov., 1994.

Dreyling, Bohlander, Adeyanju, and Olopade, "Detection of CDKN2 Deletions in Tumor Cell Lines and Primary Glioma by Interphase Fluorescence in Situ Hybridization," *Cancer Research*, 55:984–988, Mar., 1995.

Dreyling, Olopade, and Bohlander, "Detection of Deletion of the Tumor Suppressor Region on 9p21 in Acute Leukemia by Fluorescence in Situ Hybridization to Interphase Nuclei," *Blood* (Abstract #1176), p. 298a, 1995.

Dreyling, Olopade, and Bohlander, "A method for screening arrayed cosmid libraries with mega insert yeast artificial chromosomes," *Nucleic Acids Research*, 23(6):1085–1086, 1995.

Hebert, Cayuela, Berkeley, and Sigaux, "Candidate Tumor–Suppressor Genes MTS1 (p16$^{INK4A}$) and MTS2 (p15$^{INK4B}$) Display Frequent Homozygous Deletions in Primary Cells From T– But Not From B–Cell Lineage Acute Lymphoblastic Leukemias," *Blood*, 84(12):4038–4044, Dec., 1994.

Hussussian, Struewing, Goldstein, Higgins, Ally, Sheahan, Clark Jr., Tucker, and Dracopoli, "Germline p16 mutations in familial melanoma," *Nature Genetics*, 8:15–21, Sep., 1994.

Kamatani, Nelson–Rees, and Carson, "Selective killing of human malignant cell lines deficient in methylthioadenosine phosphorylase, a purine metabolic enzyme," *Proc. Natl. Acad. Sci. USA*, 78(2):1219–1223, Feb., 1981.

Kamb, Shattuck–Eidens, Eeles, Liu, Gruis, Ding, Hussey, Tran, Miki, Weaver–Feldhaus, McClure, Aitken, Anderson, Bergman, Frants, Goldgar, Green, MacLennan, Martin, Meyer, Youl, Zone, Skolnick, and Cannon–Albright, "Analysis of the p16 gene (CDKN2) as a candidate for the chromosome 9p melanoma susceptibility locus," *Nature Gentics*, 8:22–26, Sep., 1994.

Kamb, Gruis, Weaver–Feldhaus, Liu, Harshman, Tavtigian, Stockert, Day III, Johnson, and Skolnick, "A Cell Cycle Regulator Potentially Involved in Genesis of Many Tumor Types, " *Science*, 264:436–440, Apr., 1994.

Lukeis, Irving, Garson, and Hasthorpe, "Cytogenetics of Non–Small Lung Cancer: Analysis of Consistent Non–Random Abnormalities," *Genes, Chromosomes & Cancer*, 2:116–124, 1990.

(List continued on next page.)

Primary Examiner—W. Gary Jones
Assistant Examiner—Jeanine Goldberg
(74) Attorney, Agent, or Firm—Fulbright & Jaworski L.L.P.

(57) ABSTRACT

Disclosed are novel nucleic acid and peptide compositions comprising methythlioadenosine phosphorylase (MTAP) and methods of use for MTAP amino acid sequences and DNA segments comprising MTAP in the diagnosis of human cancers and development of MTAP-specific antibodies. Also disclosed are methods for the diagnosis and treatment of tumors and other proliferative cell disorders, and idenification tumor suppressor genes and gene products from the human 9p21-p22 chromosome region. Such methods are useful in the diagnosis of multiple tumor types such as bladder cancer, lung cancer, breast cancer, pancreatic cancer, brain tumors, lymphomas, gliomas, melanomas, and leukemias.

18 Claims, 25 Drawing Sheets

PUBLICATIONS

Figure 1:
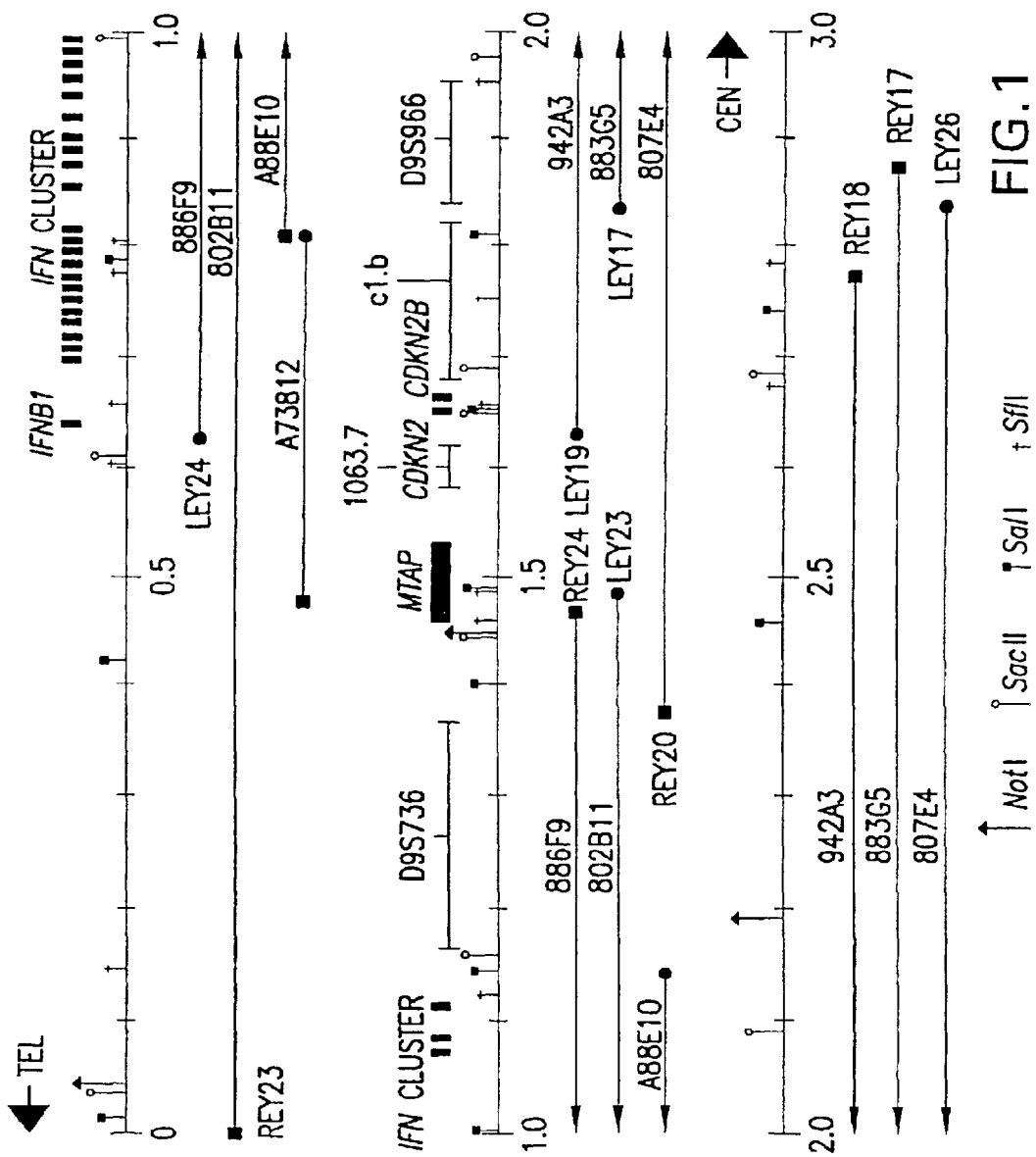

Mori, Miura, Aoki, Nishihira, Mori, and Nakamura, "Frequent Somatic Mutation of the MTS1/CDK4I (Multiple Tumor Suppressor/Cyclin–dependent Kinase 4 Inhibitor) Gene in Esophageal Squamous Cell Carcinoma," *Cancer Research*, 54:3396–3397, Jul., 1994.

Nobori, Szinai, Amox, Parker, Olopade, Buchhagen, and Carson, "Methylthioadenosine Phosphorylase Deficiency in Human Non–Small Cell Lung Cancers," *Cancer Research*, 53:1098–1101, Mar., 1993.

Nobori, Miura, Wu, Lois, Takabayashi, and Carson, "Deletions of the cyclin–dependent kinase–4 inhibitor gene in multiple human cancers," *Nature*, 368:753–756, Apr., 1994.

Nobori, Karras, Ragione, Waltz, Chen, and Carson, "Absence of Methylthioadenosine Phosphorylase in Huma Gliomas," *Cancer Research*, 51:3193–3197, Jun., 1991.

Olopade, Bohlander, Pomykala, Maltepe, Van Melle, Le Beau, and Diaz, "Mapping of the Shortest Region of Overlap of Deletions of the Short Arm of Chromosome 9 Associated with Human Neoplasia," *Genomics*, 14:437–443, 1992.

Olopade, Jenkins, Ransom, Malik, Pomykala, Nobori, Cowan, Rowley, and Diaz, "Molecular Analysis of Deletions of the Short Arm of Chromosome 9 in Human Gliomas," *Cancer Research*, 52:2523–2529, May, 1992.

Olopade, Buchhagen, Malik, Sherman, Nobori, Bader, Nau, Gazear, Minna, and Diaz, "Homozygous Loss of the Interferon Genes Defines the Critical Region on 9p That Is Deleted in Lung Cancers," *Cancer Research*, 53:2410–2415, May, 1993.

Olopade, Pomykala, Hagons, Sveen, Espinosa III, Dreyling, Gursky, Stadler, Le Beau, and Bohlander, "Construction of a 2.8–megabase yeast artificial chromosome contig and cloning of the human methylthioadenosine phosphorylase gene from the tumor suppressor region on 9p21," *Proc. Natl. Acad. Sci. USA*, 92:6489–6493, Jul., 1995.

Olopade, Ransom, Kimmel, Rowley, Diaz, and Jenkins, "Clinical Significance of Loss of the Interferon Genes in Gliomas," *Proceedings of ASCO (Abstract)*, 10:80, Mar., 1991.

Porterfield, Pomykala, Maltepe, Bohlander, Rowley, and Diaz, "The Use of Methylthioadenosine Phosphorylase Activity to Select for Human Chromosome 9 in Interspecies and Intraspecies Hybrid Cells," *Somatic Cell and Molecular Genetics*, 19(5):469–477, 1993.

Porterfield, Diaz, Rowley, and Olopade, "Induction of senescence in two human neoplastic cell lines by microcell transfer of human chromosome 9," *Proceedings of The American Association for Cancer Research (Abstract)*, 33:73, Mar., 1992.

Porterfield, Olopade, Rowley, and Diaz, "Analysis of Tumor Suppressor Gene on Human Chromosome 9 in Mouse × Human Somatic Cell Hybrids," *Somatic Cell and Molecular Genetics*, 20(5):391–400, 1994.

Povey, Armour, Farndon, Haines, Knowles, Olopade, Pilz, White, and Kwiatkowski, "REPORT on the Third International Workshop on Chromosome 9 held at Queen's College, Cambridge, UK, Apr. 9–11, 1994," *Ann. Hum. Genet. (Great Britain)*, 58:177–250, 1994.

Quesnel, Preudhomme, Philippe, Vanrumbeke, Dervite, Lai, Bauters, Wattel, and Fenaux, "p16 Gene Homozygous Deletions in Acute Lymphoblastic Leukemia," *Blood*, 85(3):657–663, Feb., 1995.

Schmidt, Ichimura, Reifenberger, and Collins, "CDKN2 (p16/MTS1) Gene Deletion or CDK4 Amplification Occurs in the Majority of Glioblastomas," *Cancer Research*, 54:6321–6324, Dec., 1994.

Serrano, Gomez–Lahoz, DePinho, Beach, and Bar–Sagi, "Inhibition of Ras–Induced Proliferation and Cellular Transformation by p16$^{INK4}$," *Science*, 267:249–252, Jan., 1995.

Serrano, Hannon, and Beach, "A new regulatory motif in cell–cycle control causing specific inhibitoin of cyclin D/CDK4," *Nature*, 366:704–707, Dec., 1993.

Thompson, Anderson, Prosser, Chetty, Carter, Evans, and Steel, "p53 Allele Losses, Mutations and Expression in Breast Cancer and Their Relationship to Clinico–Pathological Parameters," *Int. J. Cancer*, 50:528–532, 1992.

Vogelstein, Fearon, Stanley, Hamilgon, Scott, Kern, Preisinger, Leppert, Nakamura, White, Smits, and Bos, "Genetic Alterations During Colorectal–Tumor Development," *The New England Journal of Medicine*, 319(9):525–532, Sep., 1988.

Yamada, Wake, Fujimoto, Barrett, and Oshimura, "Multiple chromosomes carrying tumor suppressor activity for a uterine endometrial carcinoma cell line identified by microcell–mediated chromosome transfer," *Oncogene*, 5:1141–1147, 1990.

Zhang, Chen, and Saverese, "Codeletion of the Genes for p16$^{INK4}$, Methylthiadenosine Phosphorylase, Interferon–$\alpha_1$, Interferon–$\beta_1$, and other 9p21 Markers in Human Malignant Cell Lines," *Cancer Genet. Cytogenet.*, 86:22–28, 1996.

Carson, Willis and Kamatani, "Metabolism to Methionine and Growth Stimulation by 5'–Methylthioadenosine and 5'–Methylthioinosine," *Biochem. Biophys. Res. Comm.*, 112(2):391–397, 1983.

Kamatani and Carson, "Abnormal Regulation of Methylthioadenosine and Polyamine Metabolism in Methylthioadenosine Phosphorylase–deficient Human Leukemic Cell," *Cancer Res.*, 40:4178–4182, 1980.

Kamatani, Yu and Carson, "Deficiency of Methylthioadenosine Phosphorylase in Human Leukemic Cells In Vivo," *Blood*, 60(6):1387–1391, 1982.

Kamatani and Carson, "Dependence of Adenine Production Upon Polyamine Synthesis in Cultured Human Lymphoblasts," *Biochemica et Biophysica Acta*, 675:344–350, 1981.

Kamatani et al., "5'–Methylthioadenosine is the Major Source of Adenine in Human Cells," *Adv. Exp. Med. Biol.* 165(b):83–88, 1984.

Kamatani et al., "5'–Methylthioadenosine Phosphorylase Deficiency in Malignant Cells: Recessive Expression of the Defective Phenotype in Intraspecies (Mouse × Mouse) Hybrids)," *Adv. Exp. Med. Biol.* 165(b):279–283, 1984.

Kamatani, Nelson–Rees and Carson, "Selective Killing of Human Malignant Cell Lines Deficient in Methylthioadenosine Phosphorylase, a Purine Metabolic Enzyme," *Proc. Natl. Acad. Sci. USA*, 78(2):1219–1223, 1981.

Kamatani, Willis and Carson, "Sequential Metabolism of 5'–Isobutylthioadenosine by Methylthioadenosine Phosphorylase and Purine–Nucleoside Phosphorylase in Viable Human Cells," *Biochem. Biophys. Res. Comm.*, 104(4):1335–1342, 1982.

Kaneko et al., "Disturbance in the Metabolism of 5'–Methylthioadenosine and Adenine in Patients with Neoplastic Diseases, and in Those with a Deficiency in Adenine Phosphoribosyltransferase," *Metabolism*, 40(9):918–921, 1991.

Kaneko et al., "Measurement of 5'-Methylthioadenosine in Patients with Neoplasms," *Int. J. Cancer*, 45:8–11, 1990.

Kaneko et al., "5'-Methylthioadenosine in Urine from Normal Subjects and Cancer Patients," *Biochemica et Biophysica Acta*, 802:169–174, 1984.

Kubota, Kamatani and Carson, "Biochemical genetic Analysis of the Role of Methylthioadenosine Phosphorylase in a Murine Lymphoid Cell Line," *J. Biol. Chem.* 258(12):7288–7291, 1983.

```
   1 gaattccgct ccgcactgct cactcccgcg cagtgaggtt ggcacagcca ccgctctgtg
  61 gctcgcttgg ttcccttagt cccgagcgct cgcccactgc agattccttt cccgtgcaga
 121 catggcctct ggcaccacca ccaccgccgt gaagattgga ataattggtg aacaggcct
 181 ggatgatcca gaaattttag aaggaagaac tgaaaaatat gtggatactc catttggcaa
 241 gccatctgat gccttaattt tggggaagat aaaaaatgtt gattgcatcc tccttgcaag
 301 gcatggaagg cagcacacca tcatgccttc aaaggtcaaa taccaggcga acatctgggc
 361 tttgaaggaa gagggctgta cacatgtcat agtgaccaca gattgtggct ccttgaggga
 421 ggagattcag cccggcgata ttgtcattat tgatcagttc attgacagga ccactatgag
 481 acctcagtcc ttctatgatg aagtcattc ttgtgccaga ggagtgtgcc atattccaat
 541 ggatgagccg ttttgcccca aaacgagaga ggttcttata gagactgcta agaagctagg
 601 actccggtgc cactcaaagg gacaatggt cacaatcgag ggacctcgtt ttagctccag
 661 ggcagaaagc ttcatgttcc gcacctgggg ggcggatgtt atcaacatga ccacagttcc
 721 agaggtggtt cttgctaagg aggctggaat tgttacgca agtatcgcca tggcgacaga
 781 ttatgactgc tggaaggagc acgaggaagc agtttcggtg gaccgggtct taaagaccct
 841 gaaagaaaac gctaataaag ccaaaagctt actgctcact accatacctc agatagggtc
 901 cacagaatgg tcagaaaccc tccataacct gaagaatatg gcccagtttt ctgttttatt
 961 accaagacat taaagtagca tggctgccca ggagaaaaga agacattcta attccagtca
1021 ttttgggaat tcctgcttaa cttgaaaaaa atatgggaaa gacatgcagc tttcatgccc
1081 ttgcctatca aagagtatgt tgtaagaaag acaagacatt gtgtgtatta gagactcctg
1141 aatgatttag caacttcaa aatacagaag aaaagcaaat gactagtaaa catgtgggaa
1201 aaaatattac attttaaggg ggaaaaaaaa aaccccacca ttctcttctc cccctattaa
1261 atttgcaaca ataaagggtg gagggtaatc tctactttcc tatactgcca agaatgtga
1321 ggaagaaatg ggactctttg gttatttatt gatgcgactg taaattggta cagtatttct
1381 ggagggcaat ttggtaaaat gcatcaaaag acttaaaaat acggacgtcc tttggtgctg
1441 ggaaatctac atatagcaat ttctctttaa aaccatatca gagatgcata caaagaatta
1501 tatataaaga agggtgttta ataatgatag ttataataat aaataattga aacaatctga
1561 atcccttgca attggaggta aattatgtct tagttataat ctagattgtg aatcagccaa
1621 ctgaaaatcc tttttgcata tttcaatgtc ctaaaaagac acggttgctc tatatatgaa
1681 gtgaaaaaag gatatggtag cattttatag tactagtttt gctttaaaat gctatgtaaa
1741 tatacaaaaa aactagaaag aaatatatat aaccttgtta ttgtatttgg gggagggata
1801 ctgggataat ttttattttc tttgaatctt tctgtgtctt cacatttttc tacagtgaat
1861 ataatcaaat agtaaagggc cgtaaaaata aaagtggatt tagaaagatc cagttcttga
1921 aaacactgtt tctggtaatg aagcagaatt taagttggta atattaaggt gaatgtcatt
1981 taagggagtt acatctttat tctgctaaag aagaggatca ttgatttctg tacagtcaga
2041 acagtacttg ggtgtgcaac agctttctga gaaaagctag gtgtataata gttaactga
2101 aagtttaact atttaaaaga ctaaatgcac attttatggt atctgatatt ttaaaaagta
2161 atgtgagctt ctccttttta tgagttaaat tattttatac gagttggtaa tttgtgcctt
2221 ttaataaagt ggaagcttgc tttttaaaaa aaaaaaaaaa gcggaattc
```

FIG.3A

| | | |
|---:|:---|---:|
| 1 | MASGTTTTAVKIGIIGGTGLDDPEILEGRTEKYVDTPFGK | 40 |
| 41 | PSDALILGKIKNVDCILLARHGRQHTIMPSKVNYQANIWA | 80 |
| 81 | LKEEGCTHVIVTTACGSLREEIQPGDIVIIDQFIDRTTMR | 120 |
| 121 | PQSFYDGSHSCARGVCHIPMAEPFCPKTREVLIETAKKLG | 160 |
| 161 | LRCHSKGTMVTIEGPRFSSRAESFMFRTWGADVINMTTVP | 200 |
| 201 | EVVLAKEAGICYASIAMATDYDCWKEHEEAVSVDRVLKTL | 240 |
| 241 | KENANKAKSLLLTTIPQIGSTEWSETLHNLKNMAQFSVLL | 280 |
| 281 | PRH | 283 |

FIG.3B

34kd▸

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 2269 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 122..970

(xi) SEQUENCE DESCRIPTION: SEQ ID NO:1:

```
GAATTCCGCT CCGCACTGCT CACTCCCGCG CAGTGAGGTT GGCACAGCCA CCGCTCTGTG     60

GCTCGCTTGG TTCCCTTAGT CCCGAGCGCT CGCCCACTGC AGATTCCTTT CCCGTGCAGA    120

C ATG GCC TCT GGC ACC ACC ACC ACC GCC GTG AAG ATT GGA ATA ATT       166
  Met Ala Ser Gly Thr Thr Thr Thr Ala Val Lys Ile Gly Ile Ile
  1               5                  10                  15

GGT GGA ACA GGC CTG GAT GAT CCA GAA ATT TTA GAA GGA AGA ACT GAA     214
Gly Gly Thr Gly Leu Asp Asp Pro Glu Ile Leu Glu Gly Arg Thr Glu
                20                  25                  30

AAA TAT GTG GAT ACT CCA TTT GGC AAG CCA TCT GAT GCC TTA ATT TTG     262
Lys Tyr Val Asp Thr Pro Phe Gly Lys Pro Ser Asp Ala Leu Ile Leu
            35                  40                  45

GGG AAG ATA AAA AAT GTT GAT TGC ATC CTC CTT GCA AGG CAT GGA AGG     310
Gly Lys Ile Lys Asn Val Asp Cys Ile Leu Leu Ala Arg His Gly Arg
        50                  55                  60

CAG CAC ACC ATC ATG CCT TCA AAG GTC AAC TAC CAG GCG AAC ATC TGG     358
Gln His Thr Ile Met Pro Ser Lys Val Asn Tyr Gln Ala Asn Ile Trp
 65                  70                  75

GCT TTG AAG GAA GAG GGC TGT ACA CAT GTC ATA GTG ACC ACA GCT TGT     406
Ala Leu Lys Glu Glu Gly Cys Thr His Val Ile Val Thr Thr Ala Cys
 80                  85                  90                  95

GGC TCC TTG AGG GAG GAG ATT CAG CCC GGC GAT ATT GTC ATT ATT GAT     454
Gly Ser Leu Arg Glu Glu Ile Gln Pro Gly Asp Ile Val Ile Ile Asp
                100                 105                 110

CAG TTC ATT GAC AGG ACC ACT ATG AGA CCT CAG TCC TTC TAT GAT GGA     502
Gln Phe Ile Asp Arg Thr Thr Met Arg Pro Gln Ser Phe Tyr Asp Gly
            115                 120                 125

AGT CAT TCT TGT GCC AGA GGA GTG TGC CAT ATT CCA ATG GCT GAG CCG     550
Ser His Ser Cys Ala Arg Gly Val Cys His Ile Pro Met Ala Glu Pro
        130                 135                 140

TTT TGC CCC AAA ACG AGA GAG GTT CTT ATA GAG ACT GCT AAG AAG CTA     598
Phe Cys Pro Lys Thr Arg Glu Val Leu Ile Glu Thr Ala Lys Lys Leu
145                 150                 155

GGA CTC CGG TGC CAC TCA AAG GGG ACA ATG GTC ACA ATC GAG GGA CCT     646
Gly Leu Arg Cys His Ser Lys Gly Thr Met Val Thr Ile Glu Gly Pro
160                 165                 170                 175

CGT TTT AGC TCC CGG GCA GAA AGC TTC ATG TTC CGC ACC TGG GGG GCG     694
Arg Phe Ser Ser Arg Ala Glu Ser Phe Met Phe Arg Thr Trp Gly Ala
                180                 185                 190

GAT GTT ATC AAC ATG ACC ACA GTT CCA GAG GTG GTT CTT GCT AAG GAG     742
Asp Val Ile Asn Met Thr Thr Val Pro Glu Val Val Leu Ala Lys Glu
            195                 200                 205

GCT GGA ATT TGT TAC GCA AGT ATC GCC ATG GCG ACA GAT TAT GAC TGC     790
```

```
Ala Gly Ile Cys Tyr Ala Ser Ile Ala Met Ala Thr Asp Tyr Asp Cys
        210                 215                 220

TGG AAG GAG CAC GAG GAA GCA GTT TCG GTG GAC CGG GTC TTA AAG ACC    838
Trp Lys Glu His Glu Glu Ala Val Ser Val Asp Arg Val Leu Lys Thr
    225                 230                 235

CTG AAA GAA AAC GCT AAT AAA GCC AAA AGC TTA CTG CTC ACT ACC ATA    886
Leu Lys Glu Asn Ala Asn Lys Ala Lys Ser Leu Leu Leu Thr Thr Ile
240                 245                 250                 255

CCT CAG ATA GGG TCC ACA GAA TGG TCA GAA ACC CTC CAT AAC CTG AAG    934
Pro Gln Ile Gly Ser Thr Glu Trp Ser Glu Thr Leu His Asn Leu Lys
            260                 265                 270

AAT ATG GCC CAG TTT TCT GTT TTA TTA CCA AGA CAT TAAAGTAGCA         980
Asn Met Ala Gln Phe Ser Val Leu Leu Pro Arg His
            275                 280

TGGCTGCCCA GGAGAAAAGA AGACATTCTA ATTCCAGTCA TTTTGGGAAT TCCTGCTTAA  1040
CTTGAAAAAA ATATGGGAAA GACATGCAGC TTTCATGCCC TTGCCTATCA AAGAGTATGT  1100
TGTAAGAAAG ACAAGACATT GTGTGTATTA GAGACTCCTG AATGATTTAG ACAACTTCAA  1160
AATACAGAAG AAAAGCAAAT GACTAGTAAA CATGTGGGAA AAATATTAC ATTTTAAGGG   1220
GGAAAAAAAA AACCCCACCA TTCTCTTCTC CCCCTATTAA ATTTGCAACA ATAAAGGGTG  1280
GAGGGTAATC TCTACTTTCC TATACTGCCA AAGAATGTGA GGAAGAAATG GGACTCTTTG  1340
GTTATTTATT GATGCGACTG TAAATTGGTA CAGTATTTCT GGAGGGCAAT TTGGTAAAAT  1400
GCATCAAAAG ACTTAAAAAT ACGGACGTCC TTTGGTGCTG GGAACTCTAC ATCTAGCAAT  1460
TTCTCTTTAA AACCATATCA GAGATGCATA CAAAGAATTA TATATAAAGA AGGGTGTTTA  1520
ATAATGATAG TTATAATAAT AAATAATTGA ACAATCTGA ATCCCTTGCA ATTGGAGGTA   1580
AATTATGTCT TAGTTATAAT CTAGATTGTG AATCAGCCAA CTGAAAATCC TTTTTGCATA  1640
TTTCAATGTC CTAAAAAGAC ACGGTTGCTC TATATATGAA GTGAAAAAAG GATATGGTAG  1700
CATTTTATAG TACTAGTTTT GCTTTAAAAT GCTATGTAAA TATACAAAAA AACTAGAAAG  1760
AAATATATAT AACCTTGTTA TTGTATTTGG GGGAGGGATA CTGGGATAAT TTTTATTTTC  1820
TTTGAATCTT TCTGTGTCTT CACATTTTTC TACAGTGAAT ATAATCAAAT AGTAAAGGGC  1880
CGTAAAAATA AAAGTGGATT TAGAAAGATC CAGTTCTTGA AAACACTGTT TCTGGTAATG  1940
AAGCAGAATT TAAGTTGGTA ATATTAAGGT GAATGTCATT TAAGGGAGTT ACATCTTTAT  2000
TCTGCTAAAG AAGAGGATCA TTGATTTCTG TACAGTCAGA ACAGTACTTG GGTGTGCAAC  2060
AGCTTTCTGA GAAAGCTAG GTGTATAATA GTTTAACTGA AAGTTTAACT ATTTAAAAGA   2120
CTAAATGCAC ATTTTATGGT ATCTGATATT TTAAAAAGTA ATGTGAGCTT CTCCTTTTTA  2180
TGAGTTAAAT TATTTTATAC GAGTTGGTAA TTTGTGCCTT TTAATAAAGT GGAAGCTTGC  2240
TTTTTAAAAA AAAAAAAAAA GCGGAATTC                                   2269

(2) INFORMATION FOR SEQ ID NO:2:

(i) SEQUENCE CHARACTERISTICS:
        (A) LENGTH: 283 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ser Gly Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
```

```
                    20                  25                  30
    Tyr Val Asp Thr Pro Phe Gly Lys Pro Ser Asp Ala Leu Ile Leu Gly
            35                  40                  45

Lys Ile Lys Asn Val Asp Cys Ile Leu Leu Ala Arg His Gly Arg Gln
        50                  55                  60

His Thr Ile Met Pro Ser Lys Val Asn Tyr Gln Ala Asn Ile Trp Ala
    65                  70                  75                  80

Leu Lys Glu Glu Gly Cys Thr His Val Ile Val Thr Thr Ala Cys Gly
                    85                  90                  95

Ser Leu Arg Glu Glu Ile Gln Pro Gly Asp Ile Val Ile Ile Asp Gln
                100                 105                 110

Phe Ile Asp Arg Thr Thr Met Arg Pro Gln Ser Phe Tyr Asp Gly Ser
            115                 120                 125

His Ser Cys Ala Arg Gly Val Cys His Ile Pro Met Ala Glu Pro Phe
        130                 135                 140

Cys Pro Lys Thr Arg Glu Val Leu Ile Glu Thr Ala Lys Lys Leu Gly
    145                 150                 155                 160

Leu Arg Cys His Ser Lys Gly Thr Met Val Thr Ile Glu Gly Pro Arg
                    165                 170                 175

Phe Ser Ser Arg Ala Glu Ser Phe Met Phe Arg Thr Trp Gly Ala Asp
                180                 185                 190

Val Ile Asn Met Thr Thr Val Pro Glu Val Val Leu Ala Lys Glu Ala
            195                 200                 205

Gly Ile Cys Tyr Ala Ser Ile Ala Met Ala Thr Asp Tyr Asp Cys Trp
        210                 215                 220

Lys Glu His Glu Glu Ala Val Ser Val Asp Arg Val Leu Lys Thr Leu
    225                 230                 235                 240

Lys Glu Asn Ala Asn Lys Ala Lys Ser Leu Leu Thr Thr Ile Pro
                    245                 250                 255

Gln Ile Gly Ser Thr Glu Trp Ser Glu Thr Leu His Asn Leu Lys Asn
                260                 265                 270

Met Ala Gln Phe Ser Val Leu Leu Pro Arg His
            275                 280

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:3:

GCCGTGAAGG TGAGA                                                        15

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:4:

TCTTAGATTG GAATA                                                        15

(2) INFORMATION FOR SEQ ID NO:5:
```

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:5:

TTTGGCAAGG TTAAT                                                    15

(2) INFORMATION FOR SEQ ID NO:6:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:6:

ATGCAGCCAT CTGAT                                                    15

(2) INFORMATION FOR SEQ ID NO:7:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (xi) SEQUENCE DESCRIPTION: SEQ ID NO:7:

CTTGCAAGGT ATGG                                                     14

(2) INFORMATION FOR SEQ ID NO:8:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (xi) SEQUENCE DESCRIPTION: SEQ ID NO:8:

CCATAGGCAT GGA                                                      13

(2) INFORMATION FOR SEQ ID NO:9:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:9:

ACGAGAGAGG TGTGT                                                    15

(2) INFORMATION FOR SEQ ID NO:10:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:10:

TTCTAGGTTC TTATA                                                    15

(2) INFORMATION FOR SEQ ID NO:11:

(i) SEQUENCE CHARACTERISTICS:

```
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:11:

GAGGAAGCAG TAGGT                                                   15

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:12:

CTCTAGGTTT CGGTG                                                   15

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:13:

AACCTGAAGG TAAGT                                                   15

(2) INFORMATION FOR SEQ ID NO:14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:14:

ATCCAGAATA TGGCC                                                   15

(2) INFORMATION FOR SEQ ID NO:15:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:15:

TTGCTTTTTT AACTC                                                   15
```

METHYLTHIOADENOSINE PHOSPHORYLASE COMPOSITIONS AND METHODS OF USE IN THE DIAGNOSIS AND TREATMENT OF PROLIFERATIVE DISORDERS

The present application is a continuation-in-part of U.S. Provisional Patent Application No. 60/000,831 filed Jul. 2, 1995, the entire content of which is incorporated herein by reference.

The United States government has certain rights in the present invention pursuant to Grant DE-FG02-86ER60408 from the Department of Energy, Grant CA14599-19 from the National Cancer Institute, and Grants CA40046 and CA42557 from the United States Public Health Service.

1. BACKGROUND OF THE INVENTION

1.1 Field of the Invention

The present invention relates generally to the field of molecular biology. More specifically, it concerns novel amino acid sequences comprising the human methylthioadenosine phosphorylase (MTAP) enzyme, and the nucleic acid segments comprising the MTAP gene. Disclosed are methods and compositions related to cancer therapy involving the tumor suppressor region of human chromosome 9p21.

1.2 Description of the Related Art
1.2.1 Tumors from 9p Abnormalities

Unbalanced translocations or interstitial deletions of 9p are recurring abnormalities in a variety of tumor types including acute lymphoblastic leukemia, glioma, melanoma, non-small cell lung cancer, head and neck cancer, bladder cancer and mesothelioma (Mitelman, 1994). Homozygous deletions of DNA sequences on 9p or loss of heterozygosity have now been described in multiple tumor types (Díaz etal., 1988; 1990; Olopade etal., 1992; 1993; Kamb et al., 1994; Nobori et al., 1994). A number of the cell lines and patient samples with 9p gene deletions also lack MTAP enzyme activity. The gene encoding MTAP had not been cloned but was previously mapped to 9p22-9q13 (Carerra et al., 1984). In a few cases, the deletions that included both the IFN gene cluster and the MTIAP gene were interstitial and submicroscopic, suggesting that these genes or a tumor suppressor gene closely linked to them were the target of the 9p deletions. This hypothesis was further supported by the linkage of a gene that confers susceptibility to melanoma (MLM) to 9p21 in the region between D9S126 and the IFNA gene cluster (Cannon-Albright et al., 1992).

CDKN2 ($p16^{INK4A}$) was recently proposed as a candidate TSG in this locus because the gene has been shown to be rearranged, deleted or mutated in a majority of tumor cell lines (Kamb et al., 1994; Nobori et al., 1994). This gene codes for a 16 kDa protein (p16) that inhibits CDK4 and CDK6 by binding in competition with cyclin D (Serrano et al., 1993). In humans, CDKN2 is adjacent to a gene encoding a similar protein, now called CDKN2B ($p16^{INK4B}$) which shares 44% homology with CDKN2 in the first 50 amino acids and up to 97 percent homology in the remainder of the protein (Hannon and Beach, 1994). Whether CDKN2 is MLM remains unclear, because two recent studies provide conflicting evidence. Hussussian et al. described six different disease-related germline mutations in CDKN2 in 33 of 36 melanoma cases from 9 families and suggested that CDKN2 likely is MLM (Hussussian et al., 1994). This is in contrast to 2/13 mutations in 9p21-linked families and 0/38 familial melanoma cases described (Kamb et al., 1994).

These reports raise the possibility that CDKN2 may not be the only clinically relevant TSG on 9p and that loss of tumor suppression may involve inactivation of other as yet unidentified genes in the region in certain tumor types. Two additional regions of non overlapping homozygous deletions on 9p21 were found in malignant mesothelioma; one telomeric to CDKN2 and the other centromeric to it (Cheng et al., 1994).

The coincident loss of MTAP enzyme activity in many tumor cell lines with homozygous IFN gene deletions suggests that MTAP is closely linked to the IFN gene cluster. It was suggested that 9p TSG should be localized between the IFN gene cluster and the MTAP locus based on IFN gene rearrangements seen in two cell lines and leukemia cells from one patient with deletions on 9p (Olopade et al., 1992). In the reports published to date, it has been difficult to determine the exact position of the MTAP gene in relation to the homozygous deletions on 9p.

1.2.2 Transformation of Tumor Cells

The malignant transformation of tumor cells is known to be driven by the accumulation of various genetic alterations including numerical and structural chromosomal alterations. Among the specific alterations associated with neoplasms, the loss of tumor suppressor genes has been recognized as an important component. However, at present, deletions or mutations of the two commonly inactivated tumor suppressor genes, TP53 and RB[1], have been detected only in the minority of patients with acute lymphoblastic leukemia (ALL) (Ahuja et al., 1991; Fenaux etal., 1992).

In contrast, cytogenetic deletions of chromosomal band 9p21 have been detected in 10–15% of ALL cases indicating the presence of a novel tumor suppressor gene in this region (Kowalczyk, 1983; Chilcote, 1985; Pollak, 1987). The IFN gene cluster which is located on 9p21 was found to be deleted in 43% of leukemia derived cell lines and 29% of primary leukemia samples (Díaz etal, 1988; 1990). Recently, the CDKN2 gene ($p16^{INK4B}$, MTS I, CDK4I) which encodes an inhibitor of the cyclin-dependent kinase 4, has been found to be homozygously deleted in tumor cell lines and has been proposed as a candidate tumor suppressor gene in this region (Serrano et al., 1993; Kamb et al., 1994; Nobori et al., 1994). However, the frequency of point mutations of this gene in hematological malignancies has been very low suggesting that CDKN2 may be not the critically relevant gene on 9p (Quesnel et al., 1994). Moreover, the extent of the homozygous deletions on 9p have not been clearly delineated in primary tumors. 20 hematological malignancies were examined with cytogenetically well characterized 9p rearrangements to define the critical region of 9p.

1.2.3 Deletions in 9p21

There are now numerous reports of large homozygous or hemizygous deletions involving 9p2l in diverse types of tumors. The shortest region of overlap in the different tumor types varies and covers a large region on 9p21 usually from D9S171 to D9S162. Cannon-Albright et al. have recently refined their location for the melanoma susceptibility gene (MLM) to a region between D9S736 and D9S171, a genetic distance of at least 2 cM. Ishiiki et al. have also defined an interstitial deletion between D9S162 and D9S169, a region of 21 cM in the tumor from a patient with familial melanoma. This region encompassed both the region homozygously deleted in melanoma cell lines and the MLM locus, and also overlapped the hemizygous germline deletion seen in lymphocytes from the patient described by Petty et al. (1993) with eight primary melanomas. In bladder cancer, a putative tumor suppressor gene locus involved in bladder tumorigenesis was localized to a 10 cM region flanked by D9S 162 and D9S 171 (Cairns et al., 1994). Some investigators contend that the critical region on 9p is proximal to D9S171 while others believe the region to be telomeric to the IFN gene cluster.

The high frequency of homozygous or hemizygous deletions of this region of 9p in human tumors suggests an advantage to inactivate this locus in malignant cells. Each of the three genes identified thus far in this region appears to have some biological role in cancer. Therefore, their inclusion in the deleted region may be advantageous to the malignant cell. Alternatively, intrinsic fragility or recombinogenicity around this tumor suppressor locus may make the region a hot spot for illegitimate recombination during cell division. A fragile site has been mapped to this region of 9p. Under certain culture conditions, breaks and gaps occur at a high frequency at fragile sites because they are highly recombinogenic. Although the biological consequences of fragile site expression are not fully understood, several lines of evidence point to their involvement in carcinogenesis. Therefore, it is possible that these deletions are related to the previously mapped fragile site at 9p21.

It has been suggested that the preferred mechanism for gene inactivation in this locus is homozygous deletion rather than point mutations. That there may be more than one tumor suppressor gene in this region accounting for this phenomenon is possible. If the inactivation of more than one tumor suppressor gene is required to give the cells a growth advantage, then deletions will be favored over point mutations. If two tumor suppressor genes are closely linked in a particular chromosomal region, a deletion will frequently inactivate both at the same time, while point mutations can only inactivate one at a time, and will require two of these mutations to inactivate both genes. If the genes have a low mutation rate e.g., $10_{-8}$, then the likelihood of mutating both genes is $10^{-8} \times 10^{-8} = 10^{-16}$ which will be a rare event.

1.3 Deficiencies in the Prior Art

The problem of searching for additional genes on 9p21 in the face of as strong a candidate as CDKN2 seems daunting. However, the fact remains that there are still several unanswered questions regarding its role in tumor suppression. The mechanisms and genes involved in 9p deletions are complex and may not conform to the usual way of analyzing this problem. The characterization of tumor suppressor loci on 9p with regard to the genes included in the deletions would represent a major advancement in this area of tumor biology and cancer therapeutics. Determination of the mechanism(s) responsible for the propensity of this genomic region to undergo frequent deletions is critical in the development of tumor suppression therapies involving the 9p region. Likewise, DNA sequence analysis and elucidation of the amino acid sequence of MTAP would represent a major breakthrough in the development of novel gene therapies and medical diagnostics in the area of tumor suppression and cell proliferation disorder treatments.

2. SUMMARY OF THE INVENTION

The present invention overcomes one or more of these and other drawbacks inherent in the prior art by providing methods and compositions of tumor-associated genes and encoded gene products useful in tumor diagnosis. A defined region of 9p21 has been identified in which are located several putative tumor suppressor genes. Additionally, the entire MTAP gene has been sequenced thereby allowing development of tumor diagnostics and therapies designed to regulate such tumor-associated genes.

In certain aspects the invention includes methods of identifying various types of tumors. For example, tumors may be differentiated by comparing DNA patterns obtained from restriction analysis with several selected rare endonucleases. Thus patterns from normal tissue DNA and tumor tissue will differ as will DNA patterns from different types of tumors in a generally reproducible manner for defined conditions with the selected endonucleases.

In other aspects of the invention, methods of gene therapy are contemplated; particularly in the use of MTAP gene or fragments of MTAP gene or other tumor suppressor genes in the 9p21 region to inhibit expression of oncogenes.

Additionally, the polypeptide products of the MTAP gene and other tumor suppressor genes may be utilized to detect the presence of tumors. Assays may be conducted with antibody assays employing polyclonal or monoclonal antibodies.

It is hypothesized that the cytogenetically visible abnormalities of 9p on one chromosomal allele might unmask a mutant recessive allele of the tumor suppressor gene on the cytogenetically normal homologue. Southern blot analysis was used to determine the frequency and size of these 9p deletions using four markers generated from a 2.8 megabase YAC contig on 9p21. The results were confirmed by interphase FISH analysis. The cases with loss of one allele were analyzed by SSCP to detect point mutations of the remaining CDKN2 allele.

The invention may be employed to promote expression of a desired gene in bone cells or tissues and to impart a particular desired phenotype to the cells. This expression could be increased expression of a gene that is normally expressed (i.e., "over-expression"), or it could be used to express a gene that is not normally associated with a particular cell in its natural environment. Alternatively, the invention may be used to suppress the expression of a gene that is naturally expressed in such cells and tissues, and again, to change or alter the phenotype. Gene suppression may be a way of expressing a gene that encodes a protein that exerts a down-regulatory function, or it may utilize antisense technology.

The invention provides reliable diagnostic methods and kits to test for the presence of MTAP protein in vitro and in vivo. MTAP may serve as a marker for inactivation of the 9p21 locus in primary tumors.

Analysis of MTAP protein expression in human tumor cell lines using anti-MTAP antisera raised against peptides in the $NH_2$-terminal region of the protein has identified novel reagents which are useful in exploring selective chemotherapy in tumors with high incidence of MTAP deficiency such as pancreatic cancer, melanomas, lymphomas, leukemias, gliomas, as well as provide diagnostic tools for the identification of bladder, brain, breast, and lung cancers.

2.1 Tumor Suppressor Genes

As used herein, the term "tumor suppressor genes" is used to refer to a gene or DNA coding region that encodes a protein, polypeptide or peptide that is capable of suppressing, or assisting in the suppression of, tumor formation, or one that increases the rate of tumor suppression.

In general terms, a tumor suppressor gene may also be characterized as a gene capable of suppressing the growth rate, proliferation, or regeneration rate of a cancerous cell such as, e.g., a melanoma, tumor, glioma, carcinoma, and the like. Thus, in certain embodiments, the methods and compositions of the invention may be employed to suppress the growth or proliferation of a cancerous tissue or the cells of which it is composed.

To prepare a tumor suppressor gene segment or cDNA one may follow the teachings disclosed herein and also the teachings of any of patents or scientific documents specifically referenced herein. One may obtain a DNA segment using molecular biological techniques, such as polymerase chain reaction (PCR™) or screening a cDNA or genomic library, using primers or probes with sequences based on the corresponding nucleotide sequence. The practice of such techniques is a routine matter for those of skill in the art, as taught in various scientific articles, such as Sambrook et al. (1989), incorporated herein by reference. Certain documents further particularly describe suitable mammalian expression vectors, e.g., U.S. Pat. No. 5,168,050, incorporated herein by reference.

It is also contemplated that one may clone further genes or cDNAs that encode a tumor suppressor protein or polypeptide. The techniques for cloning DNA molecules, i.e., obtaining a specific coding sequence from a DNA library that is distinct from other portions of DNA, are well known in the art. This can be achieved by, for example, screening an appropriate DNA library. The screening procedure may be based on the hybridization of oligonucleotide probes, designed from a consideration of portions of the amino acid sequence of known DNA sequences encoding related tumor suppressor proteins. The operation of such screening protocols are well known to those of skill in the art and are described in detail in the scientific literature, for example, in Sambrook et al. (1989), incorporated herein by reference.

Tumor suppressor genes with sequences that vary from those described in the literature are also encompassed by the invention, so long as the altered or modified gene still encodes a protein that functions to suppress tumor cells in any direct or indirect manner. These sequences include those caused by point mutations, those due to the degeneracies of the genetic code or naturally occurring allelic variants, and further modifications that have been introduced by genetic engineering, i.e., by the hand of man.

Techniques for introducing changes in nucleotide sequences that are designed to alter the functional properties of the encoded proteins or polypeptides are well known in the art, e.g., U.S. Pat. No. 4,518,584, incorporated herein by reference, which techniques are also described in further detail herein. Such modifications include the deletion, insertion or substitution of bases, and thus, changes in the amino acid sequence. Changes may be made to increase the suppression activity of a protein, to increase its biological stability or half-life, to change its glycosylation pattern, and the like. All such modifications to the nucleotide sequences are encompassed by this invention.

It will, of course, be understood that one or more than one tumor suppressor gene may be used in the methods and compositions of the invention. The nucleic acid delivery methods may thus entail the administration of one, two, three, or more such genes. The maximum number of genes that may be applied is limited only by practical considerations, such as the effort involved in simultaneously preparing a large number of gene constructs or even the possibility of eliciting a significant adverse, cytotoxic effect. For example, particular combinations of genes may be used to produce the most desirable effects, e.g., the combination of two or more distinct tumor suppressor genes.

In using multiple genes, they may be combined on a single genetic construct under control of one or more promoters, or they may be prepared as separate constructs of the same or different types. Thus, an almost endless combination of different genes and genetic constructs may be employed. Certain gene combinations may be designed to, or their use may otherwise result in, achieving synergistic effects on tumor cell suppression, any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic acid segment or gene could be administered in combination with further agents, such as, e.g., proteins or polypeptides or various pharmaceutically active agents. So long as genetic material forms part of the composition, there is virtually no limit to other components which may also be included, given that the additional agents do not cause a significant adverse effect upon contact with the target cells or tissues. The nucleic acids may thus be delivered along with various other agents as necessary.

2.2 MTAP-Encoding DNA Segments

The present invention, in a general and overall sense, concerns the isolation and characterization of a novel gene, MTAP which encodes the methylthioadenosine phosphorylase, MTAP. A preferred embodiment of the present invention is a purified nucleic acid segment that encodes a protein having an amino acid sequence as shown in FIG. 3B, and in accordance with SEQ ID NO:2. Another embodiment of the present invention is a purified nucleic acid segment, further defined as including a nucleotide sequence in accordance with SEQ ID NO:1.

In a more preferred embodiment the purified nucleic acid segment consists essentially of the nucleotide sequence of SEQ ID NO:1. As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a MTAP coding sequence yet is isolated away from, or purified free from, total genomic DNA, for example, total cDNA or human genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified MTAP gene refers to a DNA segment including MTAP coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences or combinations thereof. "Isolated substantially away from other coding sequences" means that the gene of interest, in this case MTAP, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a MTAP gene, that includes within its amino acid sequence an amino acid sequence in accordance with SEQ ID NO:2. Moreover, in other particular embodiments, the invention concerns isolated DNA segments and recombinant vectors incorporating DNA sequences which encode a gene that includes within its amino acid sequence the amino acid sequence of a MTAP gene corresponding to human MTAP.

Another preferred embodiment of the present invention is a purified nucleic acid segment that encodes a protein in accordance with SEQ ID NO:2, further defined as a recombinant vector. As used herein the term, "recombinant vector", refers to a vector that has been modified to contain a nucleic acid segment that encodes a MTAP protein, or a fragment thereof. The recombinant vector may be further defined as an expression vector comprising a promoter operatively linked to the MTAP-encoding nucleic acid segment.

A further preferred embodiment of the present invention is a host cell, made recombinant with a recombinant vector comprising a MTAP gene. The recombinant host cell may be a prokaryotic cell. In a more preferred embodiment, the recombinant host cell is a eukaryotic cell. As used herein, the term "engineered" or "recombinant" cell is intended to refer to a cell into which a recombinant gene, such as a gene encoding MTAP, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, one cannot exclude the possibility of employing a genomic version of a particular gene where desired.

In certain embodiments, the invention concerns isolated DNA segments and recombinant vectors which encode a protein or peptide that includes within its amino acid sequence an amino acid sequence essentially as set forth in SEQ ID NO:2. Naturally, where the DNA segment or vector encodes a full length MTAP protein, or is intended for use in expressing the MTAP protein, the most preferred sequences are those which are essentially as set forth in SEQ ID NO:2.

The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein, as a gene having a sequence essentially as set forth in SEQ ID NO:2, and that is associated with a tumor suppressor gene. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:2 will be sequences which are "essentially as set forth in SEQ ID NO:2."

In certain other embodiments, the invention concerns isolated DNA segments and recombinant vectors that include within their sequence a nucleic acid sequence essentially as set forth in SEQ ID NO:1. The term "essentially as set forth in SEQ ID NO:1," is used in the same sense as described above and means that the nucleic acid sequence substantially corresponds to a portion of SEQ ID NO:1, and has relatively few codons which are not identical, or functionally equivalent, to the codons of SEQ ID NO:1. The term "functionally equivalent codon" is used herein to refer to codons that encode the same amino acid, such as the six codons for arginine or serine, as set forth in Table 1, and also refers to codons that encode biologically equivalent amino acids.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 70% and about 80%; or more preferably, between about 80% and about 90%; or even more preferably, between about 90% and about 99%; of nucleotides which are identical to the nucleotides of SEQ ID NO:1 will be sequences which are "essentially as set forth in SEQ ID NO:1". Sequences which are essentially the same as those set forth in SEQ ID NO:1 may also be functionally defined as sequences which are capable of hybridizing to a nucleic acid segment containing the complement of SEQ ID NO:1 under relatively stringent conditions. Suitable relatively stringent hybridization conditions will be well known to those of skill in the art and are clearly set forth herein, for example conditions for use with southern and northern blot analysis, and as described in Example 1.

Naturally, the present invention also encompasses DNA segments which are complementary, or essentially complementary, to the sequence set forth in SEQ ID NO:1. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1 under relatively stringent conditions such as those described herein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1, such as about 10 to 15 or 20, 30, or 40 or so nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

A preferred embodiment of the present invention is a nucleic acid segment which comprises at least a 14-nucleotide long stretch which corresponds to, or is complementary to, the nucleic acid sequence of SEQ ID NO:1. In a more preferred embodiment the nucleic acid is further defined as comprising at least a 20 nucleotide long stretch, a 30 nucleotide long stretch, 50 nucleotide long stretch, 100 nucleotide long stretch, a 200 nucleotide long stretch, a 500 nucleotide long stretch, a 1000 nucleotide long stretch, or at least an 1118 nucleotide long stretch which corresponds to, or is complementary to, the nucleic acid sequence of SEQ ID NO:1. The nucleic acid segment may be further defined as having the nucleic acid sequence of SEQ ID NO:1.

A related embodiment of the present invention is a nucleic acid segment which comprises at least a 14-nucleotide long stretch which corresponds to, or is complementary to, the nucleic acid sequence of SEQ ID NO:1, further defined as comprising a nucleic acid fragment of up to 10,000 bp in length. A more preferred embodiment if a nucleic acid fragment comprising from 14 nucleotides of SEQ ID NO:1 up to 5,000 bp in length, 3,000 bp in length, 1,000 bp in length, 500 bp in length, or 100 bp in length.

Naturally, it will also be understood that this invention is not limited to the particular nucleic acid and amino acid sequences of SEQ ID NO:1 and SEQ ID NO:2. Recombinant vectors and isolated DNA segments may therefore variously include the MTAP coding regions themselves, coding regions bearing selected alterations or modifications in the basic coding region, or they may encode larger polypeptides which nevertheless include MTAP-coding regions or may encode biologically functional equivalent proteins or peptides which have variant amino acids sequences.

The DNA segments of the present invention encompass biologically functional equivalent MTAP proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the MTAP protein or to test ATAP mutants in order to examine tumor suppressor activity or determine the presence of the MTAP peptide in various cells and tissues at the molecular level.

A preferred embodiment of the present invention is a purified composition comprising a polypeptide having an amino acid sequence in accordance with SEQ ID NO:2. The term "purified" as used herein, is intended to refer to a MTAP protein composition, wherein the MTAP protein is purified to any degree relative to its naturally-obtainable state, i.e., in this case, relative to its purity within a eukaryotic cell extract. MTAP protein may also be isolated from patient specimens, recombinant cells, tissues, isolated subpopulations of tissues, and the like, as will be known to those of skill in the art, in light of the present disclosure. A purified MTAP protein composition therefore also refers to a polypeptide having the amino acid sequence of SEQ ID NO:2, free from the environment in which it may naturally occur.

If desired, one may also prepare fusion proteins and peptides, e.g., where the MTAP coding regions are aligned within the same expression unit with other proteins or peptides having desired functions, such as for purification or immunodetection purposes (e.g., proteins which may be purified by affinity chromatography and enzyme label coding regions, respectively).

Turning to the expression of the MTAP gene whether from cDNA based or genomic DNA, one may proceed to prepare an expression system for the recombinant preparation of MTAP protein. The engineering of DNA segment(s) for expression in a prokaryotic or eukaryotic system may be performed by techniques generally known to those of skill in recombinant expression. For example, one may prepare a MTAP-GST (glutathione-S-transferase) fusion protein that is a convenient means of bacterial expression. However, it is believed that virtually any expression system may be employed in the expression of MTAP.

MTAP may be successfully expressed in eukaryotic expression systems, however, it is contemplated that bacterial expression systems can be used for the preparation of MTAP for all purposes. The cDNA containing MTAP may be separately expressed in bacterial systems, with the encoded proteins being expressed as fusions with β-galactosidase, avidin, ubiquitin, *Schistosoma japonicum* glutathione S-transferase, multiple histidines, epitope-tags and the like. It is believed that bacterial expression will ultimately have advantages over eukaryotic expression in terms of ease of use and quantity of materials obtained thereby.

It is proposed that transformation of host cells with DNA segments encoding MTAP will provide a convenient means for obtaining an MTAP protein. It is also proposed that cDNA, genomic sequences, and combinations thereof, are suitable for eukaryotic expression, as the host cell will, of course, process the genomic transcripts to yield fluctional mRNA for translation into protein.

Another embodiment is a method of preparing a protein composition comprising growing recombinant host cell comprising a vector that encodes a protein which includes an amino acid sequence in accordance with SEQ ID NO:2, under conditions permitting nucleic acid expression and protein production followed by recovering the protein so produced. The host cell, conditions permitting nucleic acid expression, protein production and recovery, will be known to those of skill in the art, in light of the present disclosure of the MTAP gene.

2.3 Gene Constructs and DNA Segments

As used herein, the terms "gene" and "DNA segment" are both used to refer to a DNA molecule that has been isolated free of total genomic DNA of a particular species. Therefore, a gene or DNA segment encoding a tumor suppressor gene refers to a DNA segment that contains sequences encoding a tumor suppressing protein, but is isolated away from, or purified free from, total genomic DNA of the species from which the DNA is obtained. Included within the term "DNA segment", are DNA segments and smaller fragments of such segments, and also recombinant vectors, including, for example, plasmids, cosmids, phage, retroviruses, adenoviruses, and the like.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest, in this case, a tumor suppressor gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, such as sequences encoding leader peptides or targeting sequences, later added to the segment by the hand of man.

This invention provides novel ways in which to utilize various known tumor suppressor DNA segments and recombinant vectors. As described above, many such vectors are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a tumor suppressor protein and does not include any coding or regulatory sequences that would have a significant adverse effect on suppression of tumor growth and/or cell proliferation. Therefore, it will also be understood that useful nucleic acid sequences may include additional residues, such as additional non-coding sequences flanking either of the 5' or 3' portions of the coding region or may include various internal sequences, i.e., introns, which are known to occur within genes.

After identifying an appropriate tumor suppressor gene or DNA molecule, it may be inserted into any one of the many vectors currently known in the art, so that it will direct the expression and production of the tumor suppressor protein when incorporated into a cell. In a recombinant expression vector, the coding portion of the DNA segment is positioned under the control of a promoter. The promoter may be in the form of the promoter which is naturally associated with a tumor suppressor gene, as may be obtained by isolating the 5' non-coding sequences located upstream of the coding segment or exon, for example, using recombinant cloning and/or PCR™ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a tumor suppressor gene in its natural environment. Such promoters may include those normally associated with other tumor suppressor genes, and/or promoters isolated from any other bacterial, viral, eukaryotic, or mammalian cell. Naturally, it will be important to employ a promoter that effectively directs the expression of the DNA segment in the cell in which the construct is to be introduced.

The use of recombinant promoters to achieve protein expression is generally known to those of skill in the art of molecular biology, for example, see Sambrook et al. (1989). The promoters employed may be constitutive, or inducible, and can be used under the appropriate conditions to direct high level or regulated expression of the introduced DNA segment. The currently preferred promoters are those such as CMV, RSV LTR, the SV40 promoter alone, and the SV40 promoter in combination with various enhancer elements.

Tumor suppressor genes and DNA segments may also be in the form of a DNA insert which is located within the genome of a recombinant virus, such as, for example a recombinant adenovirus, adeno-associated virus (AAV) or retrovirus. In such embodiments, to place the gene in contact with a tumor cell, one would prepare the recombinant viral particles, the genome of which includes the tumor suppressor gene insert, and simply contact the cells or tissues with the virus, whereby the virus infects the cells and transfers the genetic material.

3. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1. PFGE map of the 2.8-Mb YAC contig on 9p21. The individual YAC's are aligned to the long-range restriction map above each overlapping segment. Restriction sites are designated as shown. This map does not show every restriction site for the enzymes SalI, SacII, and SfiI because sites that are further away from the probes used were not detected. The IFNB1 and IFNA genes and pseudogenes and the MTAP, CDKN2, and CDKN2B genes are represented by solid vertical bars. Broad locations for the markers D9S736, D9S966, 1063.7, and cl.b are shown. REY and LEY designate the right and left YAC vector arms, respectively. YACs A73B12 and A88E10 were derived with IFN STS from the St. Louis YAC library (Porterfield et al., 1992). Cosmids and end-rescued plasmid clones are not shown. Distances are drawn to scale; marked distances are in megabases.

Figure 2A:
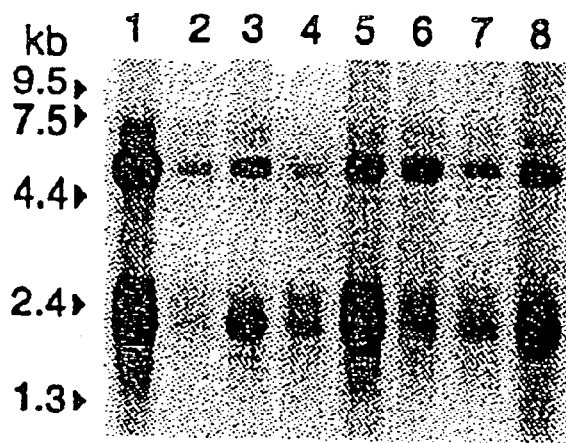

FIG. 2A. Northern blot of RNA from multiple human tissues hybridized with the 3' 1.4-kb fragment of the MTAP cDNA clone. Lanes: 1, heart: 2, brain; 3, placenta; 4, lung; 5, liver; 6, skeletal muscle; 7, kidney; 8, pancreas.

Figure 2B:
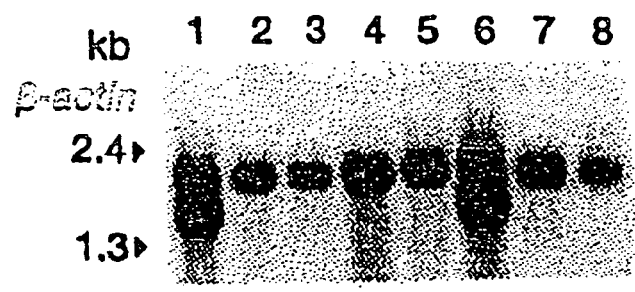

FIG. 2B. Northern analysis of the blot in FIG. 2A re-probed with β-actin cDNA. Lanes: 1, heart: 2, brain; 3, placenta; 4, lung; 5, liver; 6, skeletal muscle; 7, kidney; 8, pancreas.

FIG. 3A. Nucleotide sequence of the MTAP cDNA (SEQ ID NO:1).

FIG. 3B. Protein sequence of the MTAP gene product (SEQ ID NO:2).

Figure 4:
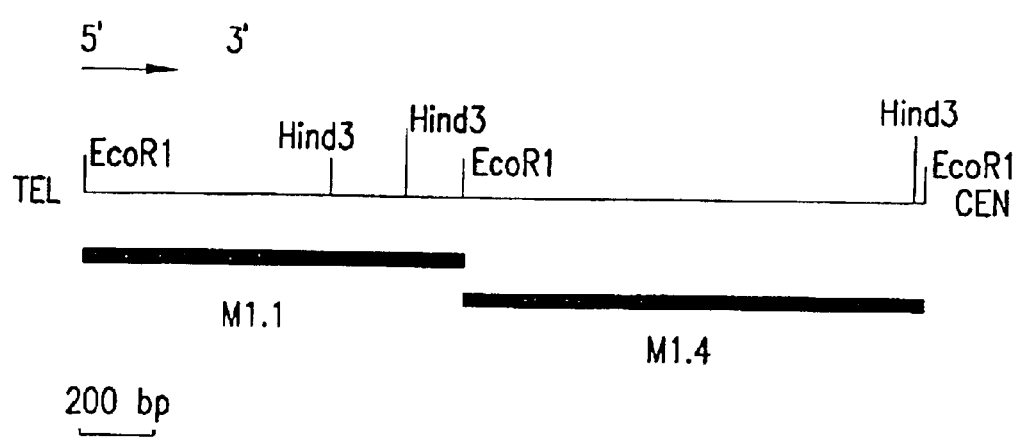

FIG. 4. Map of MTAP cDNA clone. Not all restriction sites are indicated.

Figure 5:
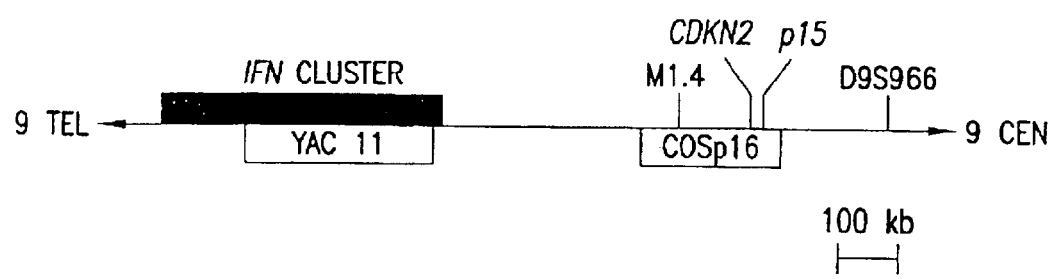

FIG. 5. Map of the DNA markers on 9p21. The positions of different FISH probes (YAC11 and COSp16) and molecular markers (M1.4, CDKN2, CDKN2B [p15], and D9S966) are shown.

Figure 6A:
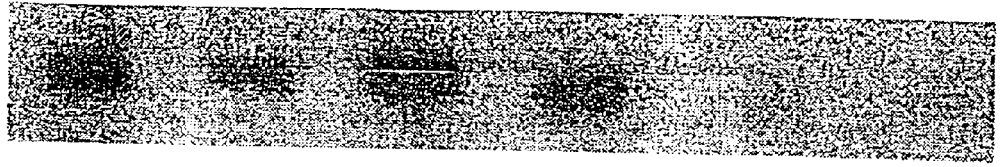

FIG. 6A. Southern blot analysis of 5 representative cases (lane 1, placental control; lane 2, patient no. 2; lane 3, patient no. 3; lane 4, patient no. 4; lane 5, patient no. 5; lane 6, patient npo. 11). The hybridization is shown with M1.4. Homozygous deletions can be detected in lanes, 3, 5, and 6. The intensity of the bands in lane 2 is significantly reduced. The case of lane 4 has a hemizygous 9p deletion detected by FISH.

Figure 6B:
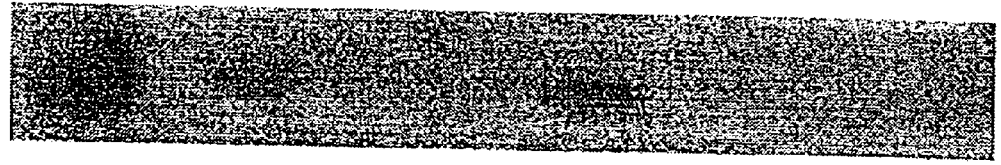

FIG. 6B. Southern blot analysis of 5 representative cases (lane 1, placental control; lane 2, patient no. 2; lane 3, patient no. 3; lane 4, patient no. 4, lane 5, patient no. 5; lane 6, patient no. 11). The hybridization is shown with CDKN2, exon 2. Homozygous deletions can be detected in lanes, 3, 5, and 6. The intensity of the bands in lane 2 is significantly reduced. The case of lane 4 has a hemizygous 9p deletion detected by FISH.

Figure 6C:
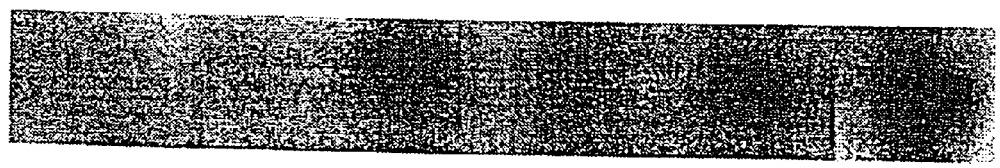

FIG. 6C. Southern blot analysis of 5 representative cases (lane 1, placental control; lane 2, patient no. 2; lane 3, patient no. 3; lane 4, patient no. 4, lane 5, patient no. 5; lane 6, patient no. 11). The hybridization is shown with CDKN2B, exon 1. Homozygous deletions can be detected in lanes, 3, 5, and 6. The intensity of the bands in lane 2 is significantly reduced. The case of lane 4 has a hemizygous 9p deletion detected by FISH.

Figure 6D:
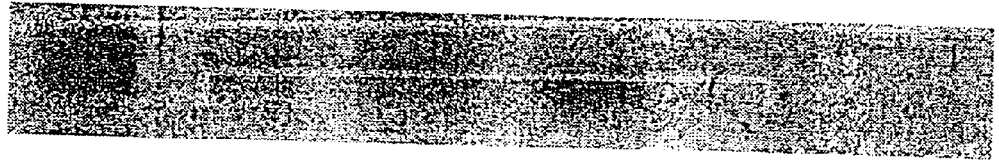

FIG. 6D. Southern blot analysis of 5 representative cases (lane 1, placental control; lane 2, patient no. 2; lane 3, patient no. 3; lane 4, patient no. 4, lane 5, patient no. 5; lane 6, patient no. 11). The hybridization is shown with D9S966. Homozygous deletions can be detected in lanes, 3, 5, and 6. The intensity of the bands in lane 2 is significantly reduced. The case of lane 4 has a hemizygous 9p deletion detected by FISH.

Figure 6E:

FIG. 6E. Southern blot analysis of 5 representative cases (lane 1, placental control; lane 2, patient no. 2; lane 3, patient no. 3; lane 4, patient no. 4, lane 5, patient no. 5; lane 6, patient no. 11). The hybridization is shown with the control probe transferrin receptor TFR(E). Homozygous deletions can be detected in lanes, 3, 5, and 6. The intensity of the bands in lane 2 is significantly reduced. The case of lane 4 has a hemizygous 9p deletion detected by FISH.

Figure 7A:
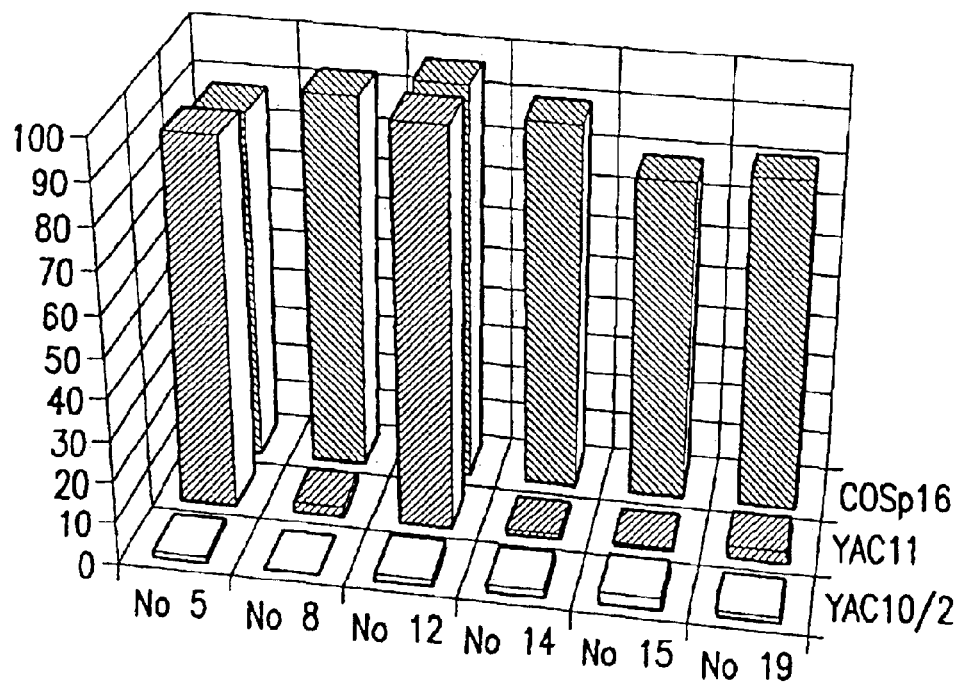

FIG. 7A. FISH analysis in 6 cases with the homozygous deletion of the CDKN2 region. The percentage of cells without hybridization signal. (YAC 10/2, YAC 11, and COSp16) is shown.

Figure 7B:
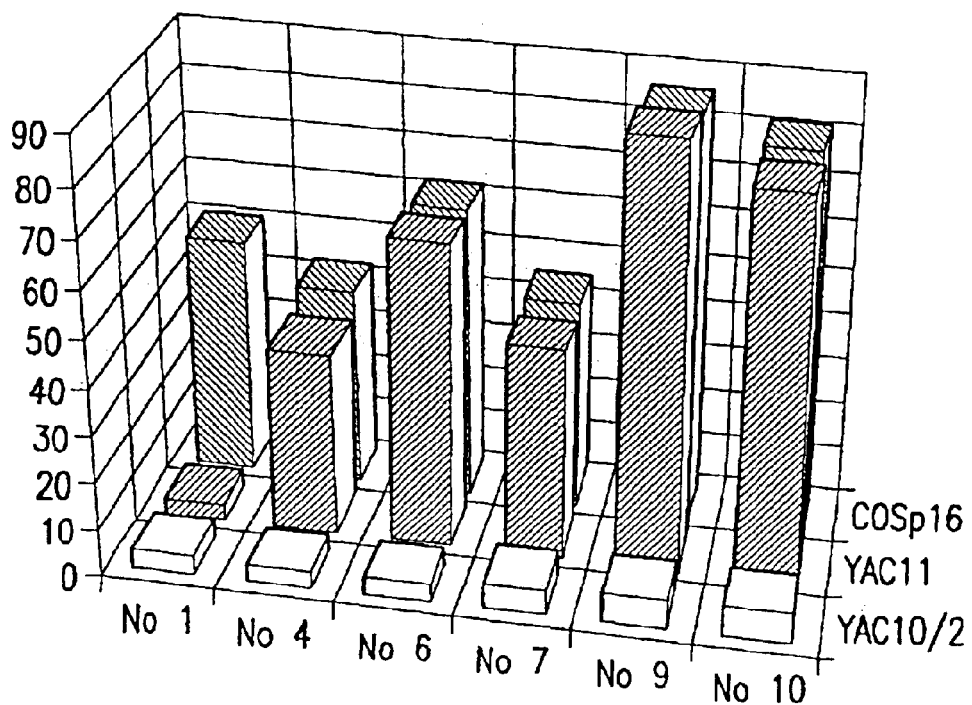

FIG. 7B. FISH analysis in 6 cases with the hemizygous deletions of the CDKN2 region. The percentage of cells with one hybridization signal. (YAC 10/2, YAC 11, and COSp16) is shown. Cases no. 8, 14, 15, and 19 have hemizygous deletions of YAC 11.

Figure 8:
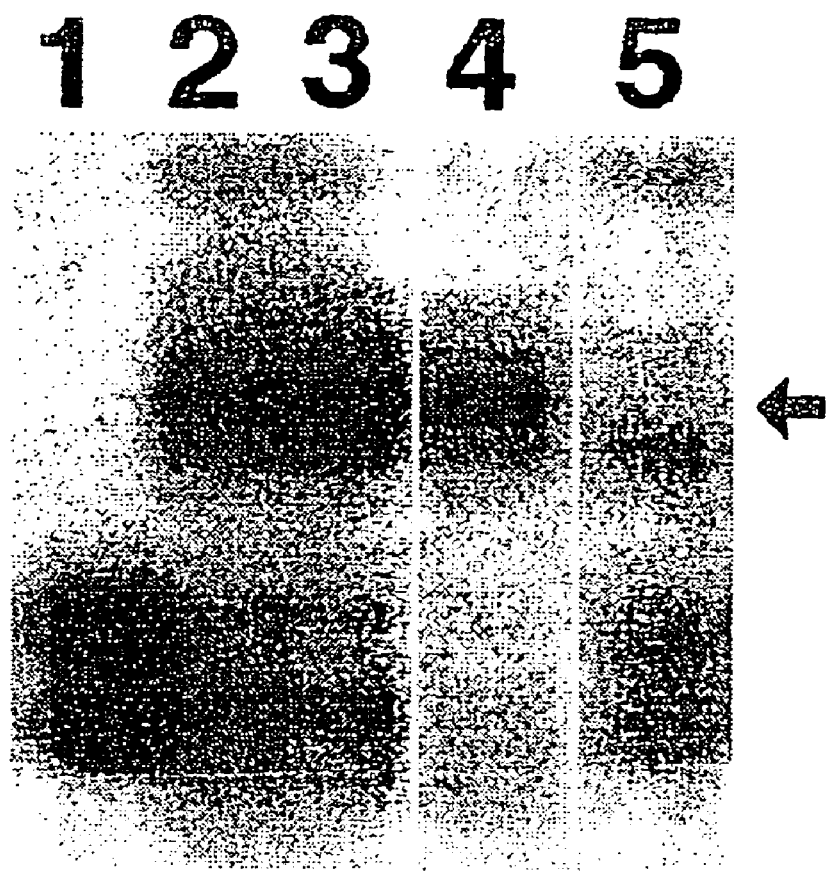

FIG. 8. SSCP analysis of CDKN2, exon 2 with control DNA (lane 1, non-denatured; lane 2, denatured), 2 cases with hemizygous CDKN2 deletion (lane 3, no. 1; lane 4, no. 16), and HL60 (lane 5), a cell line with known point mutation in exon 2. HL60 shows a changed mobility of bands. None of the patients samples differs from placental DNA.

Figure 9:
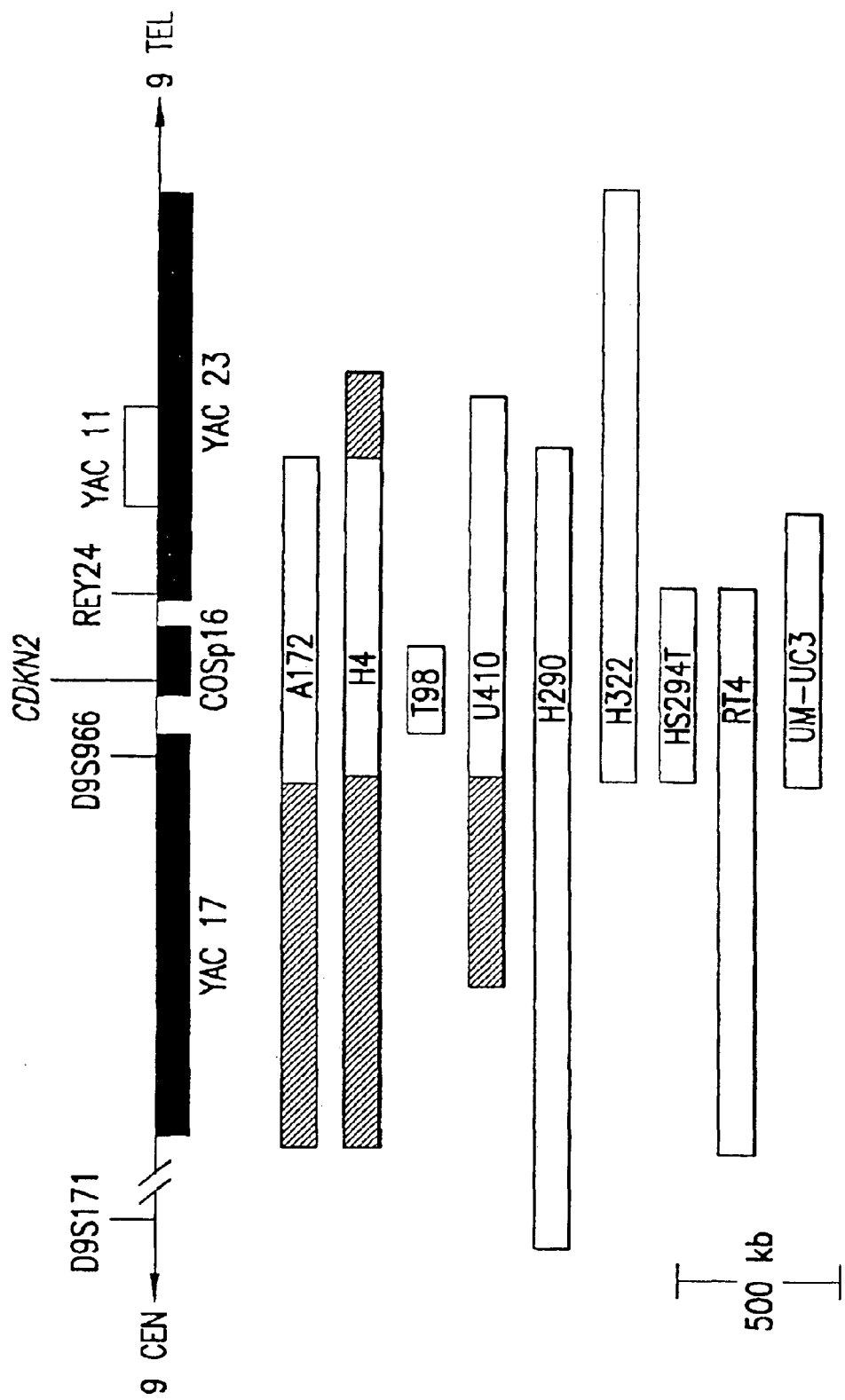

FIG. 9. 9p deletion map of the cell lines. The position of different FISH probes (YAC 11, YAC 23, YAC 17, COSp16) and molecular markers (REY24, CDKN2, D9S966, D9S171) are shown. R, homozygous deletions; diagonal lines, non-homozygous deletions, kb, kilobases.

Figure 10A:
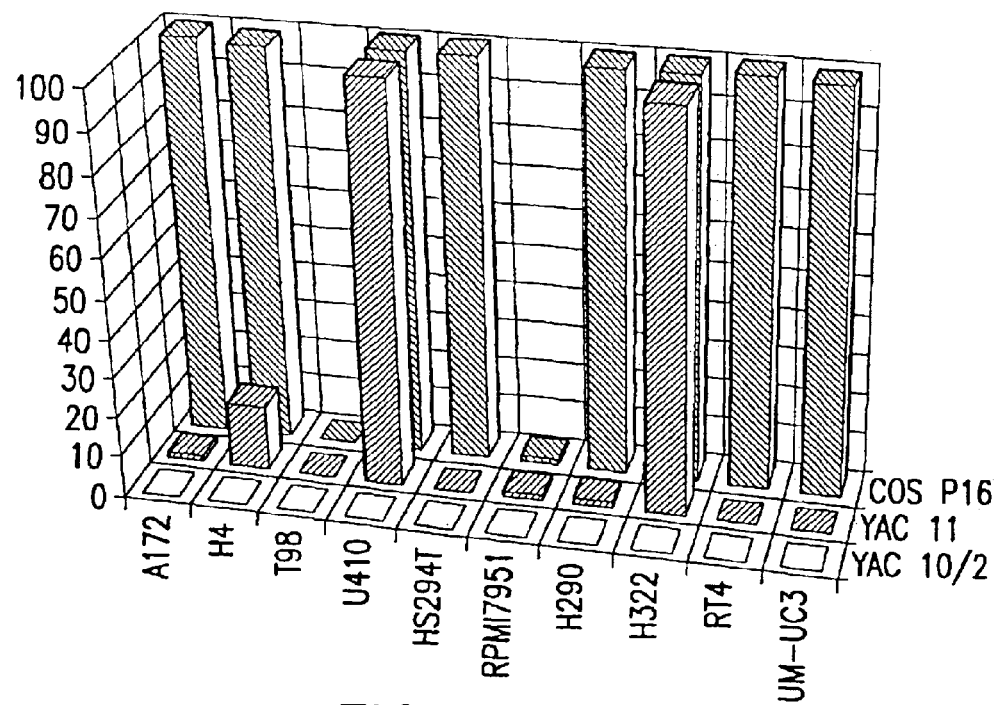

FIG. 10A. FISH analysis in 10 tumor cell lines. The percentage of cells without hybridization signal (YAC 10/2, YAC 11, COSp16) is shown.

Figure 10B:
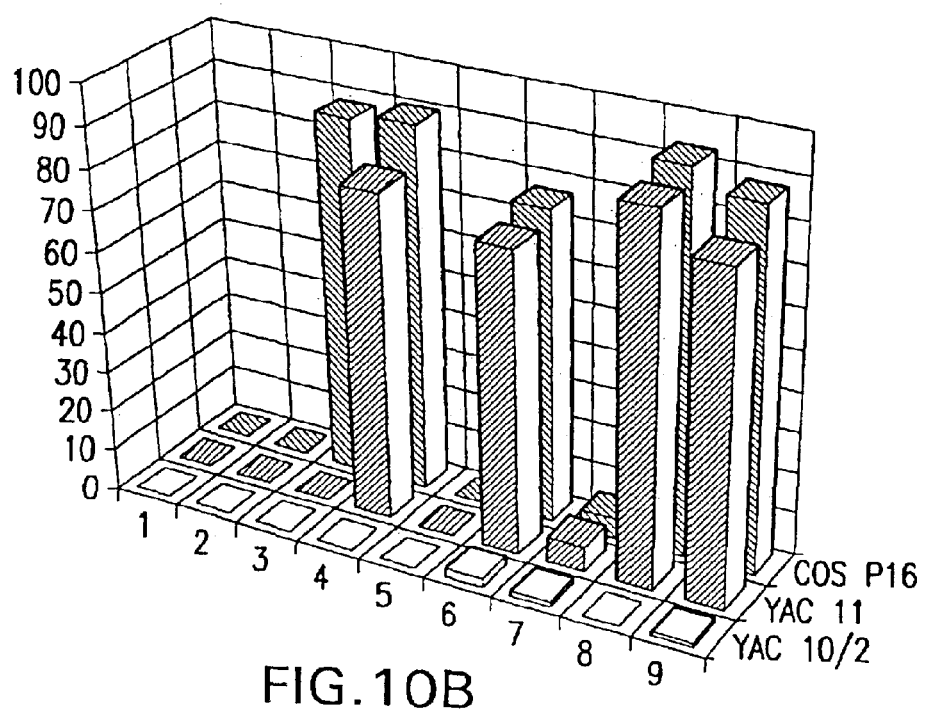

FIG. 10B. FISH analysis in 9 glioblastomas. The percentage of cells without hybridization signal (YAC 10/2, YAC 11, COSp16) is shown.

Figure 11:
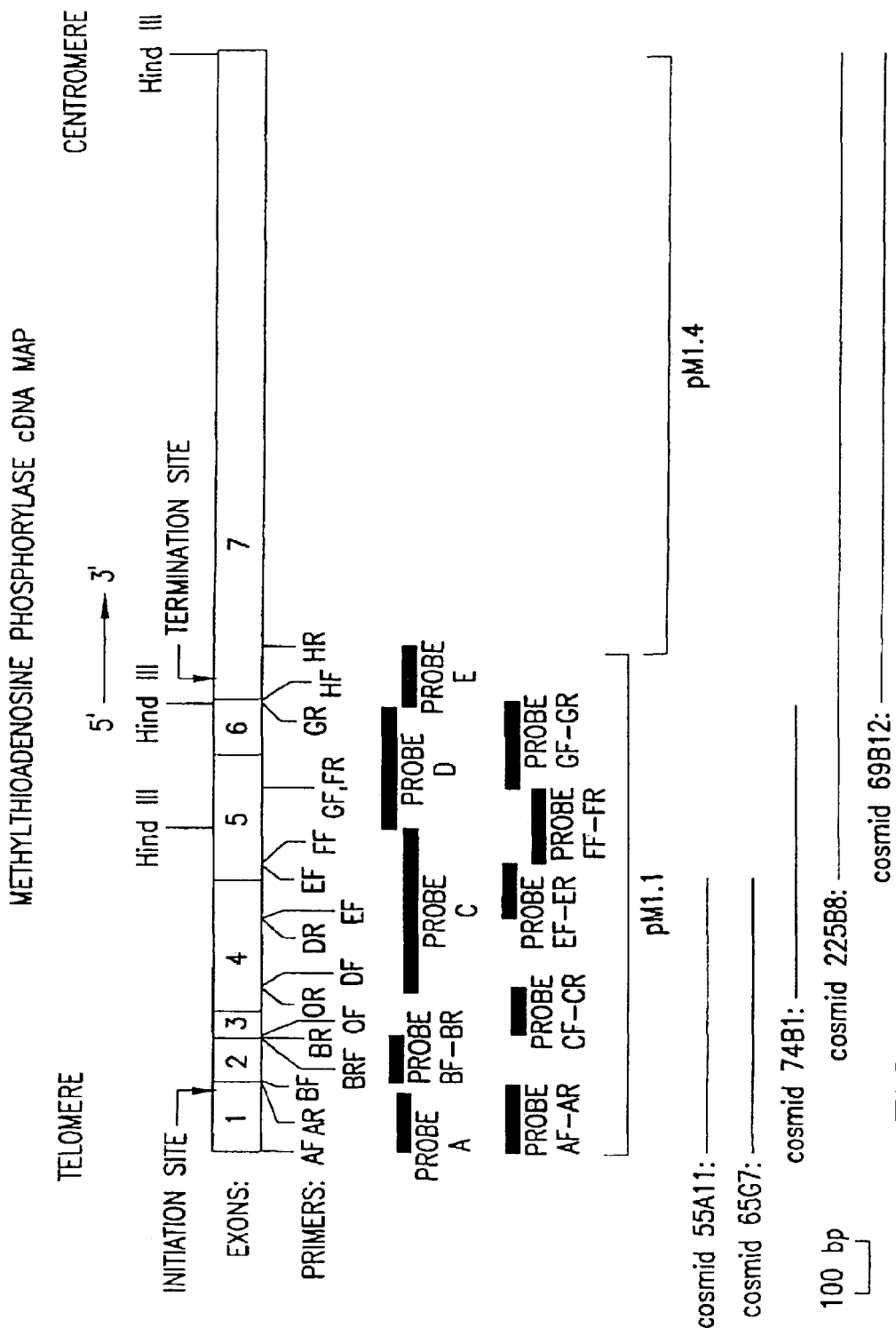

FIG. 11. cDNA map of the MTAP region.

Figure 12:
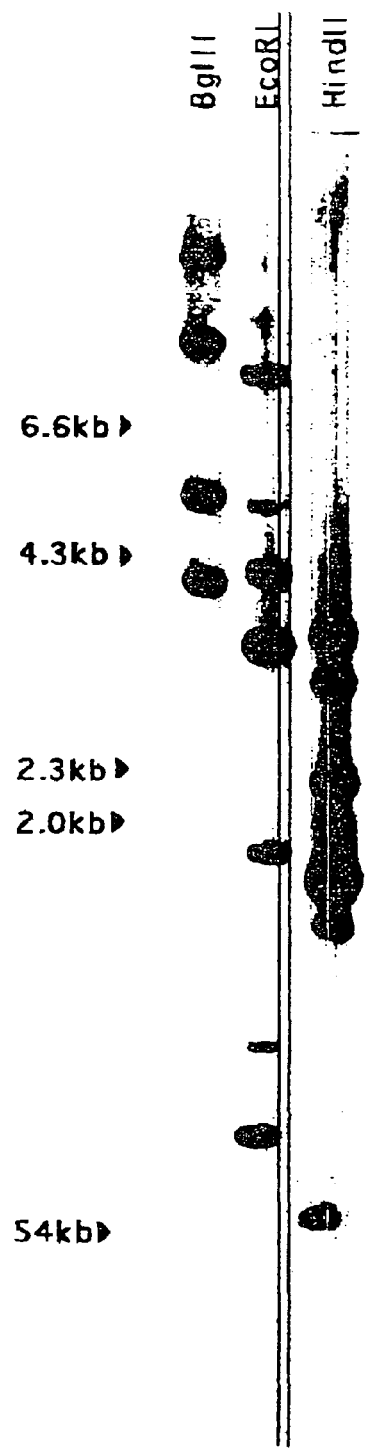

FIG. 12. Southern blot of genomic placental DNA probed with pM 1.1. The lanes are labeled with the corresponding restriction enzyme used.

Figures 13, 14:
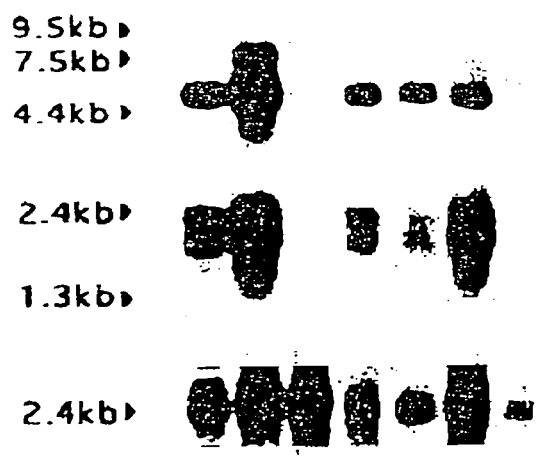

FIG. 13. Upper panel shows a northern blot of RNA from tumor cell lines hybridized with the 3' 1.4-kb fragment of the MTAP cDNA clone. The lower panel shows the same blot probed with a control cDNA. Lanes 1, HL60; lane 2, HeLa; lane 3, K562; lane 4, Molt 4; lane 5, RAJt; lane 6, SV40; lane 7, A549:7 G361.1.

FIG. 14. Shown is the 34-kDa translation product of the pM1.1 cDNA clone using the TNT T3-Coupled Reticulocyte lysate system from Promega Corp.

Figure 15:
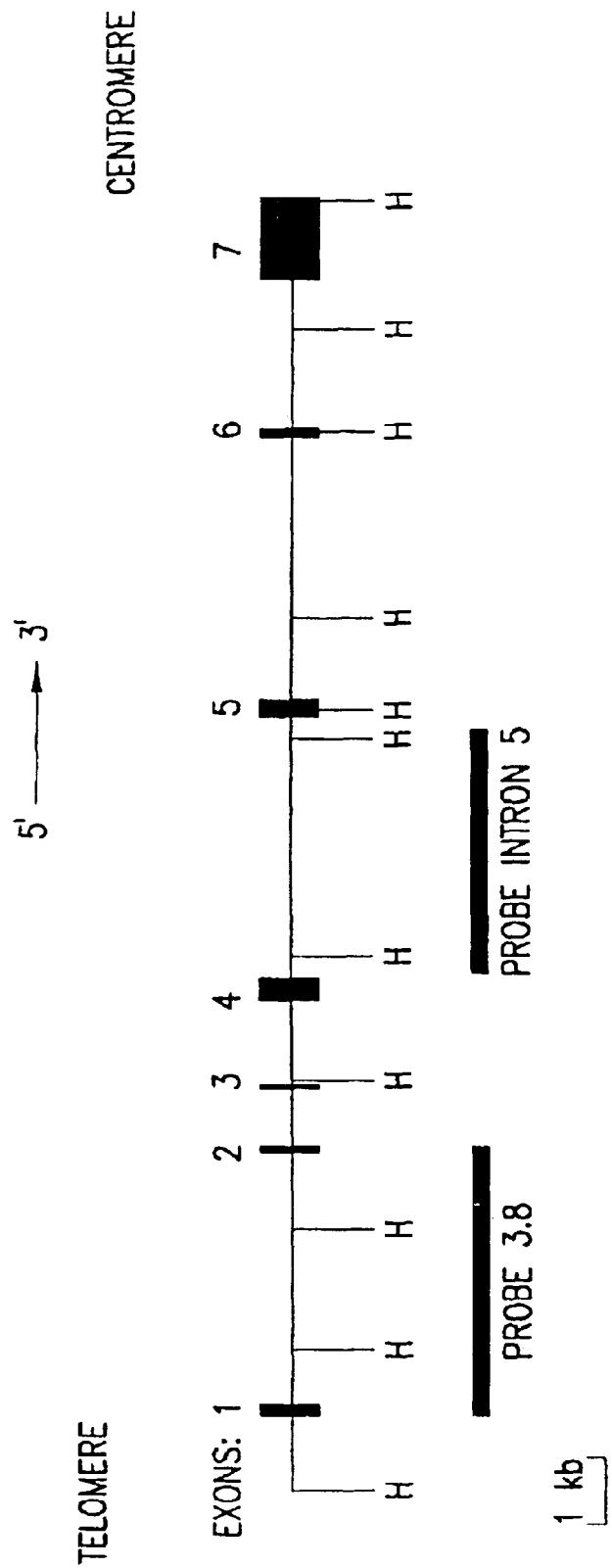
Figure 16A:
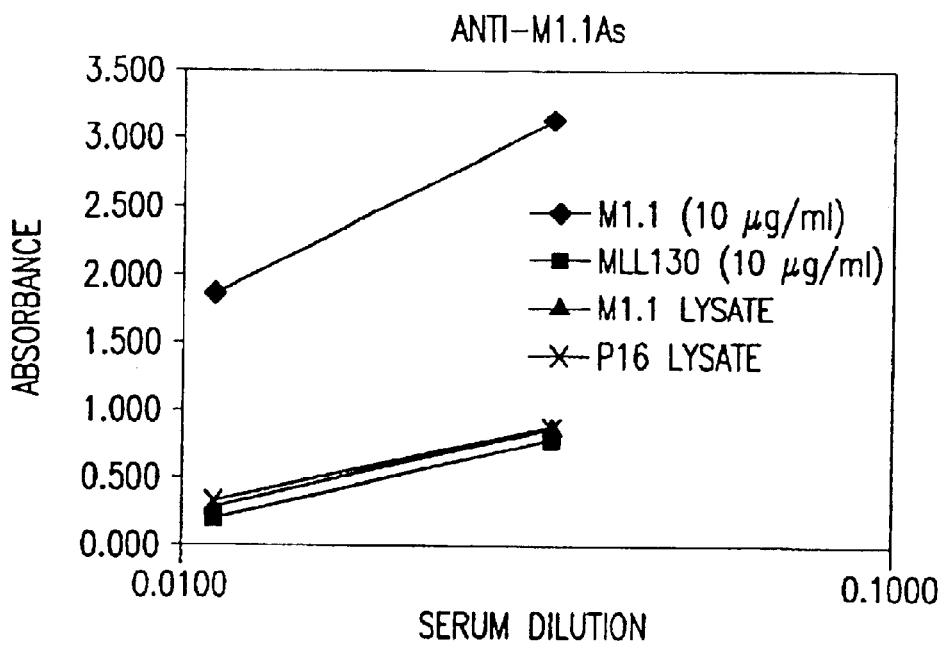
Figure 16B:
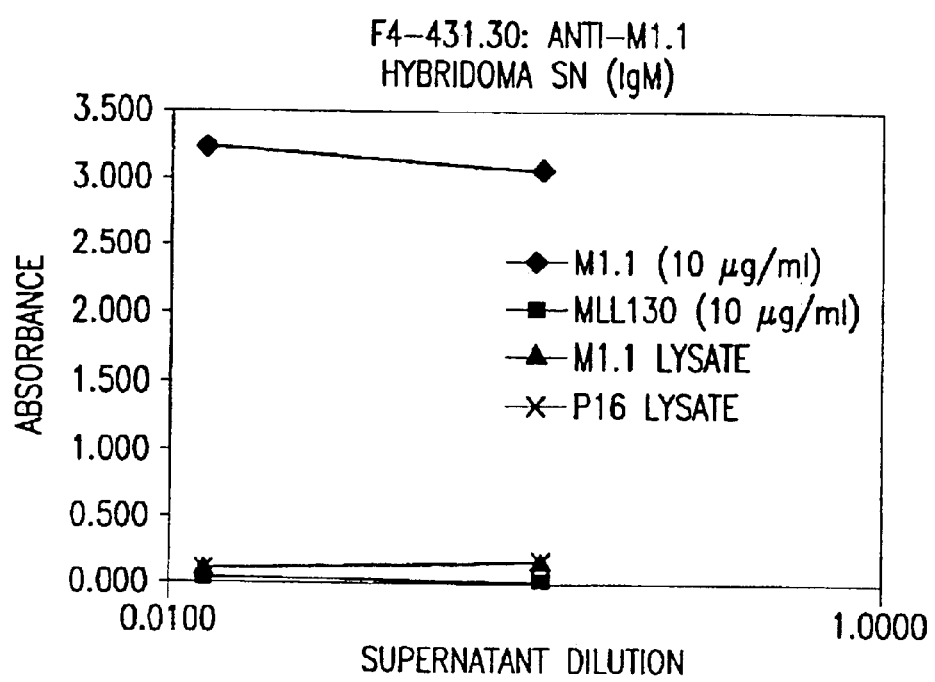
Figure 16C:
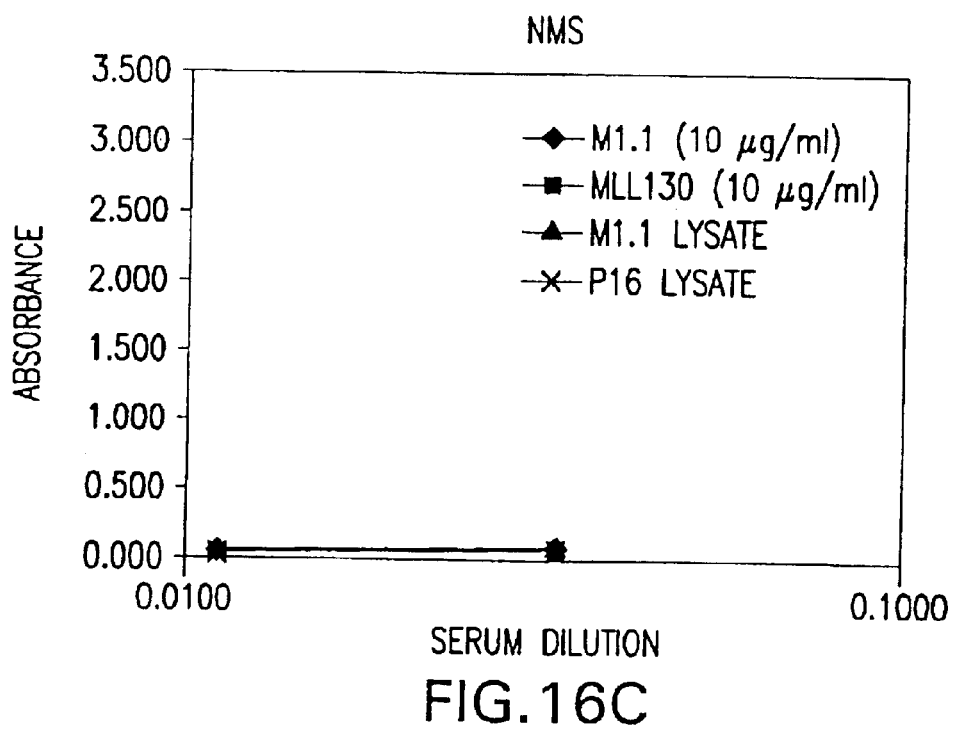
Figure 16D:
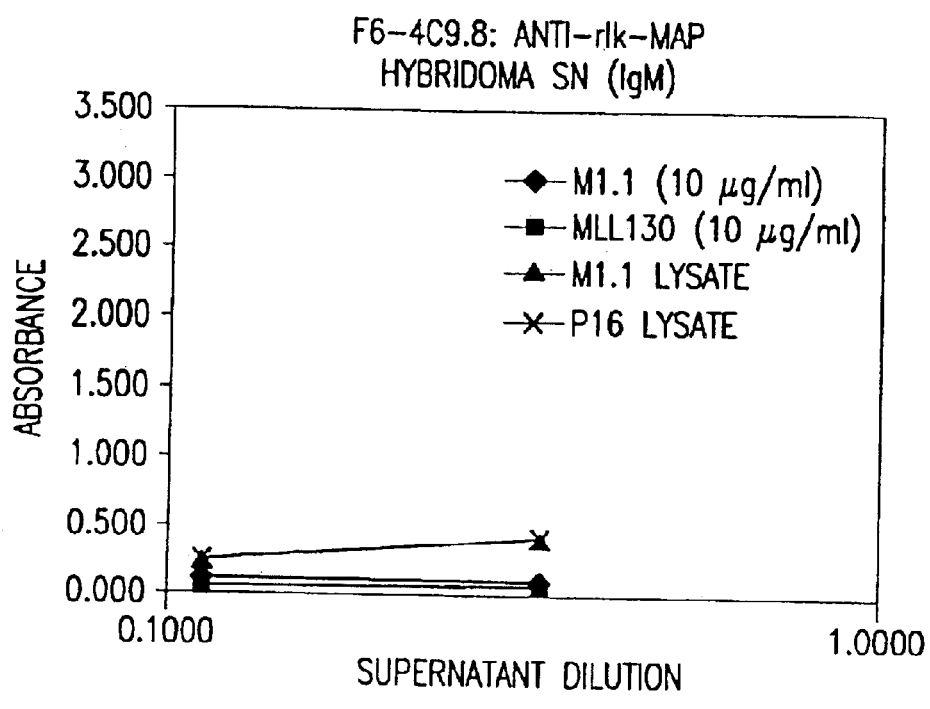

FIG. 15. Genomic organization of the MTAP gene.

FIG. 16. Titration of M1.1, MLL, and M1.1 and P16 lysates. Shown are absorbance vs. dilution plots.

Figure 17A:
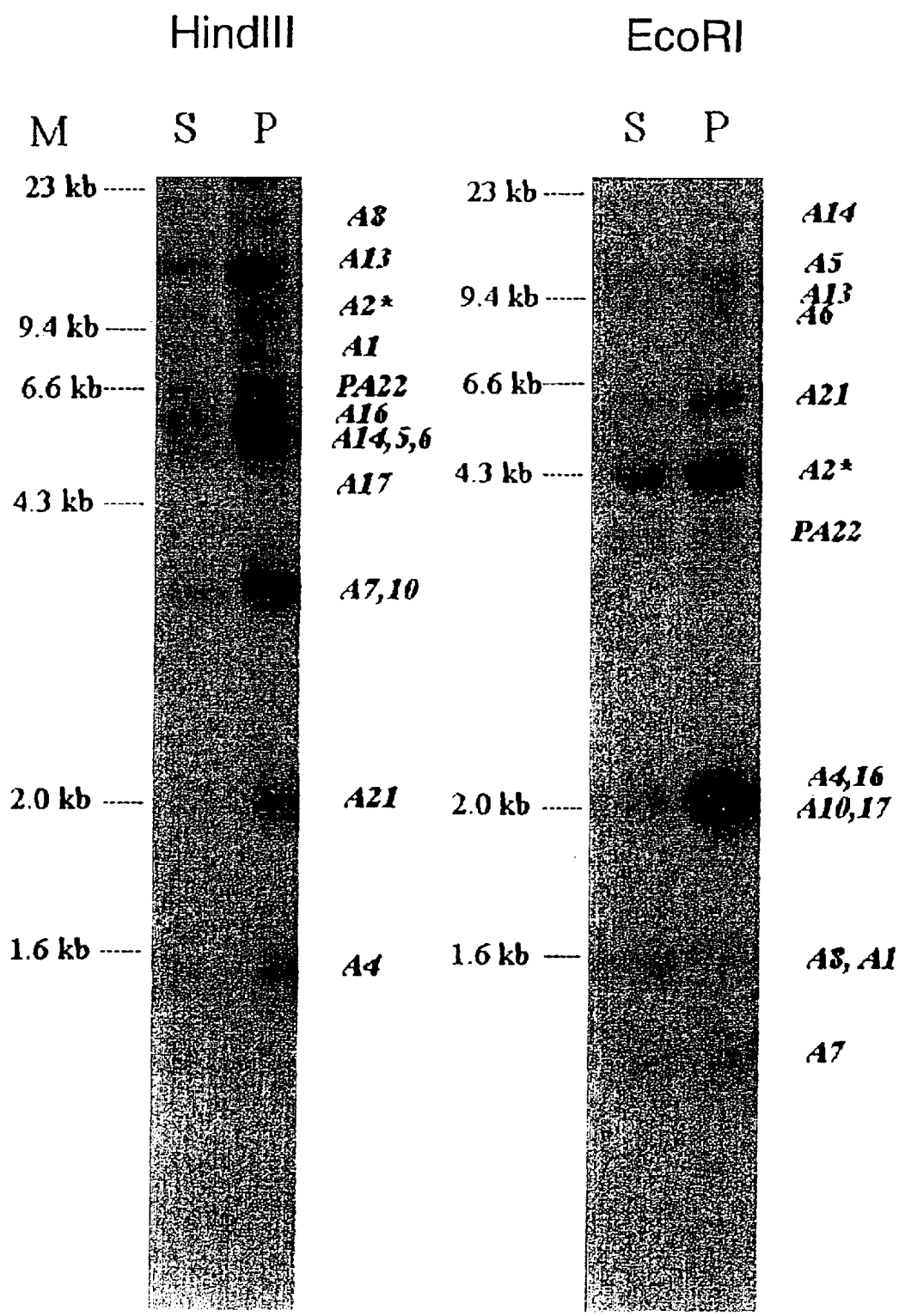

FIG. 17A. BV173 Southern Blot Results. From left to right the panels show results of the IFNA2 coding region hybridized to HindIII, and EcoRI supernatant and pellet fractions. Each IFNA fragment containing each gene member is identified to the right using the proper nomenclature. R values were measured and includes 12 different HindIII, and EcoRI DNA fragments as shown below. These examples were chosen to show supernatant, and pellet scaffold binding regions. M=λ phage HindIII markers. Examples from Southern blots where the coding regions coding plus immediate flanking regions showed 70% or greater supernatant enrichment (R=<30) are a 1.4 kb EcoRI fragment containing IFNAI (R=>5) (FIG. 17B), and both a 1.2 kb and 1.6 kb EcoRI fragments containing IFNA8 (R=15). Examples where most IFN gene family members mapped to DNA fragments which were enriched greater than 70% in the pellet (R=>70) and where it is mapped 5 SARs specifically to either the 5' or 3' flanking regions are: a 1-kb EcoRI fragment containing IFNA 7 and a 3' SAR, a 58-kb HindIII fragment and a 2-kb EcoRI fragment containing IFNA16 and 3' and 5' SARs respectively (R=75), a 2.0-kb EcoRI fragment (R=75), and a 4.4-kb HindIII fragment containing IFNA1 7 and 5' and 3' SARs respectively, an 8.4-kb EcoRI fragment containing IFNA13 and a 5' SAR, a 5.5-kb HindIII fragment containing IFNA14 and a 5' and 3' SARs. Examples where additional R values were measured for fragments which contained coding sequences plus 5' and 3' flanking regions and which were enriched >70% into the pellet fraction: (R=≦70) from the left panel (HindIII) to the right panel (EcoRI), IFNA8 9.4-kb HindIII (R=80), IFNA10 3.5-kb HindIII fragment (R=93). IFNA21 6.0 kb EcoRI (R=86), IFNA2 4.8-kb EcoRI (R=70), IFNA4, 10, 16, 2.0-kb EcoRI (R=75). These fragments were analyzed as containing two strong SARs mapping both 5' and 3' to the coding regions.

Figure 17B:
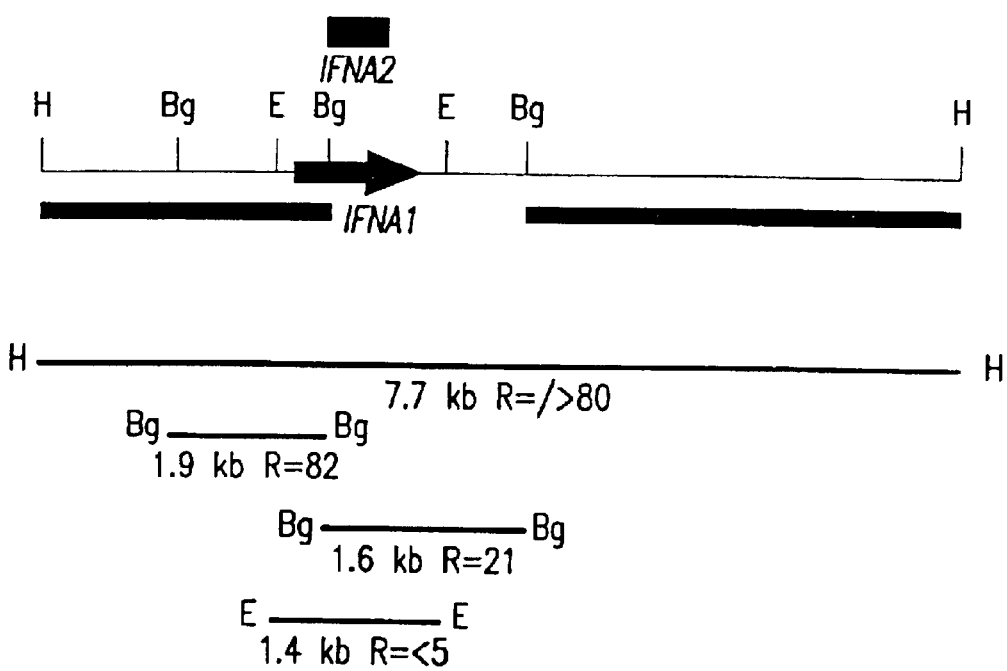

FIG. 17B. Strategy used to map SARs in the IFN gene cluster. Restriction enzyme map of INFA1 showing the location of SARs both 5' and 3' of the gene. See FIG. 17A for representative Southerns. H=HindIII, Bg=BglII, E=EcoRI, INFA1→, weak SAR=□, SAR=■, IFNA2 coding region probe=■ shown above INFA1. R values are represented below the map along with the particular restriction fragments. A 7.7-kb HindIII fragment (R=80) hybridizing with the IFNA2 coding region was enriched 80% into the pellet (FIG. 17A). The 1.4-kb EcoRI fragment (R=<5) contains the INFA1 coding region and was enriched in the supernatant. Two BglII fragments (each hybridizing to one half of IFNA1), a 1.6-kb fragment (R=21) was supernatant enriched, and a 1.3-kb fragment (R=62) distributed about equally into the supernatant and pellet fractions. For this region it is predicted that two high affinity SARs map outside the coding region past the EcoRI sites. The weak binding of the 1.3-kb BglII fragment contains part of the scaffold binding sites from the 5' high affinity SAR. The 3' SAR begins outside the EcoRI and BglII sites.

Figure 18:
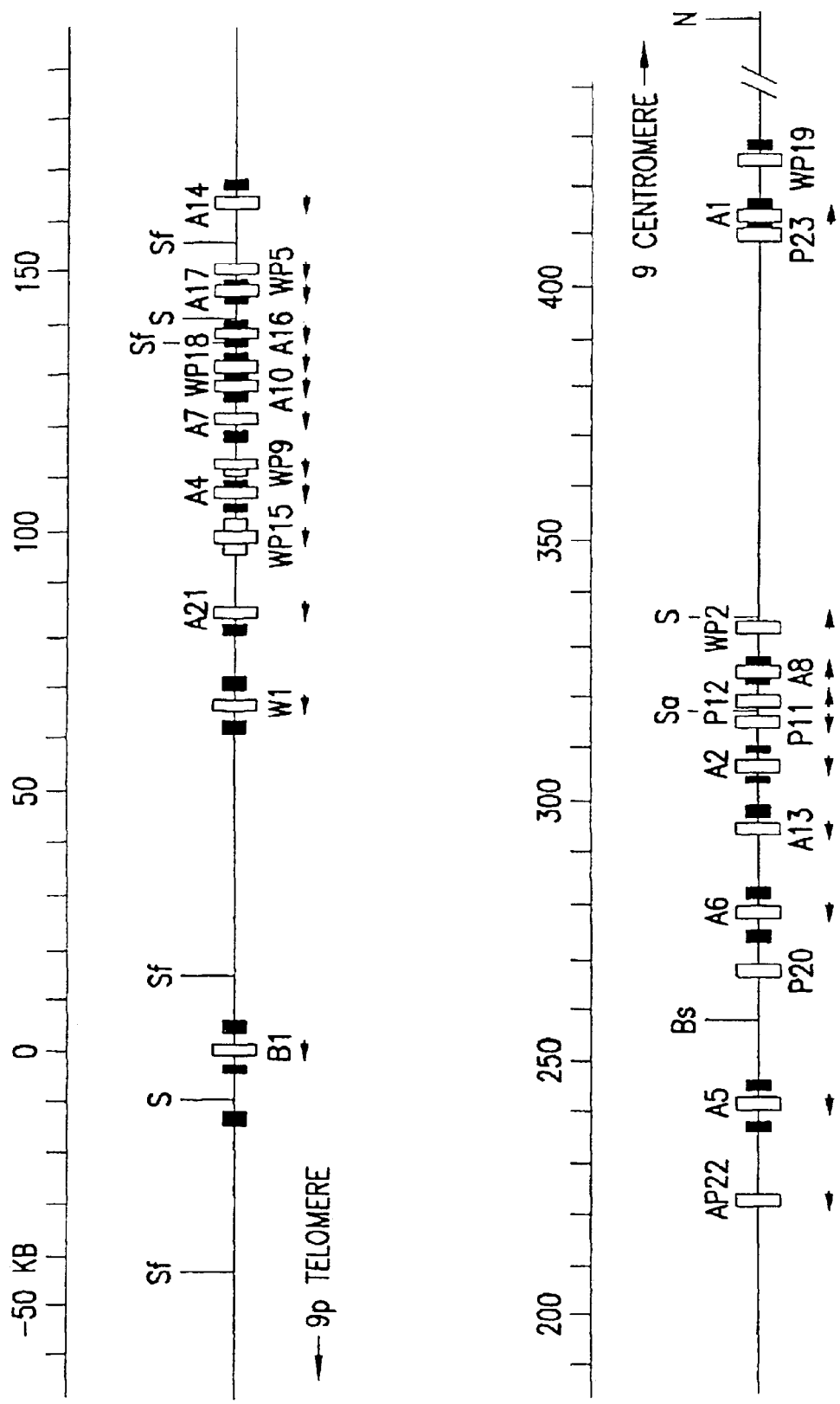

FIG. 18. Long-range restriction map of the IFNB1 and IFNA and IFNW gene families on Chromosome 9p and the location of SARs. Long-range restriction map showing approximately 500 kb of the 9p region containing the IFNBI, IFNA and IFNW genes. The sizes (in kb) are indicated above the restriction map. Restriction enzyme sites are the following: SF=SfiI, S=SalI, Bs=BstI, and n=NotI. All genes and pseudogenes are labeled with the standard IFN terminology. Long vertical open boxes along the map represent the IFNBI coding region the IFNA and IFNPA coding regions, the IFNW and IFNPW coding regions. Long vertical open boxes also represent the specific pseudogenes. Small black rectangular boxes represent strong SARs, small open boxes represent weak SARs. SAR locations were mapped from the hybridization of the IFNA2 and IFNW1 coding regions to SAR (pellet) and non-SAR (supernatant) DNA fractions.

FIG. 19. Restriction enzyme map of the IFNA2, IFNP11, IFNP12 and IFNA8 gene region showing the location of SARs 1, 2, 3, 4, 5, and 6. In the 3' flanking region of IFNA2 the single high affinity SAR1 begins close to the gene (approximately 0.5-kb) and then extends 3' for approximately 2.6 kb. The most proximal high affinity IFNA2 SAR2 begins approximately 1 kb upstream of the gene and extends 4.8-kb 5' of the gene. The third high affinity SAR3 starts approximately 9-kb upstream of IFNA2 and extends 2.5 kb. Weak SARs flank IFNP11 and IFNP12. The size of weak SAR4 is 1.4 kb, but the exact sizes of weak SAR5 and SAR6 are unknown. H=HindIII, Bg=BglII, B=BamHI, a-n= restriction DNA fragments used as probes. →=IFNA2, IFNA8, ⇒=TIFNP11, IFNP12, Weak SAR=□, Strong SAR= ■. Horizontal bars below the map represent DNA restriction fragments showing different R values. Human genomic λ clones are shown below map.

Figure 19A:
Figure 19B:
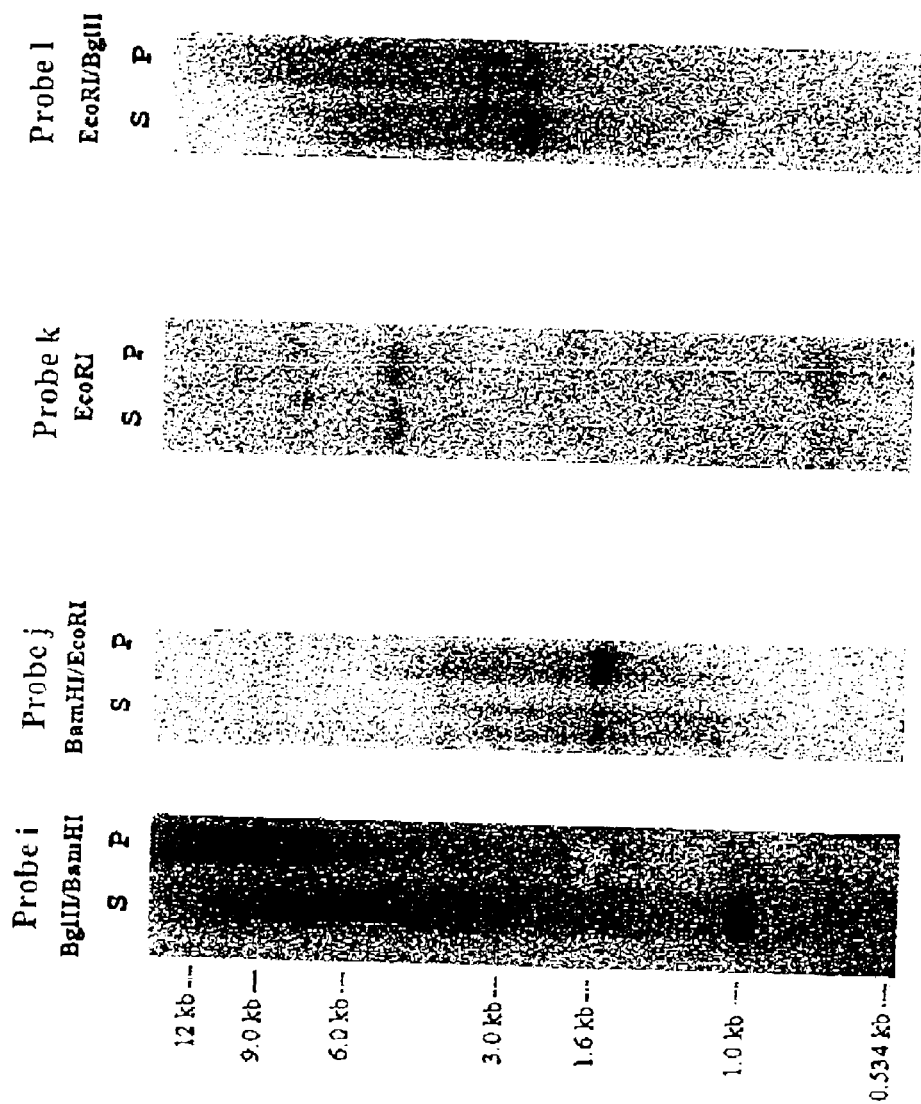

FIG. 19B. Southern blot results showing hybridization of probes i, j, k, and l to BglII/BamHI, BamHI/EcoRI, EcoRI and EcoRI/BglII digested scaffolds. λ HindIII marker lane is represented to the left of the Southern blot panels. Probe i represents a supernatant enriched DNA fragment whereas probes j, and k identify pellet enriched fragments of SAR3. Probe l identifies a weaker binding region just centromeric to SAR3. The 5.7-kb band seen hybridizing with probe k is most likely the partial EcoRI fragment which contains the 0.7-kb EcoRI fragment plus weak SARs 4 and 5. The 3.7-kb band observed in the EcoRI/BglII pellet fraction represents the 3.7-kb EcoRI/EcoRI fragment detecting the most proximal IFNA2 SAR. This result is due to co-purifying the 4.4-kb fragment or probes h, i, and j from the λ 1-3 phage. The 4.4-kb EcoRI fragment detects the strong SAR3. See FIG. 19A for representative R values.

Figure 20:
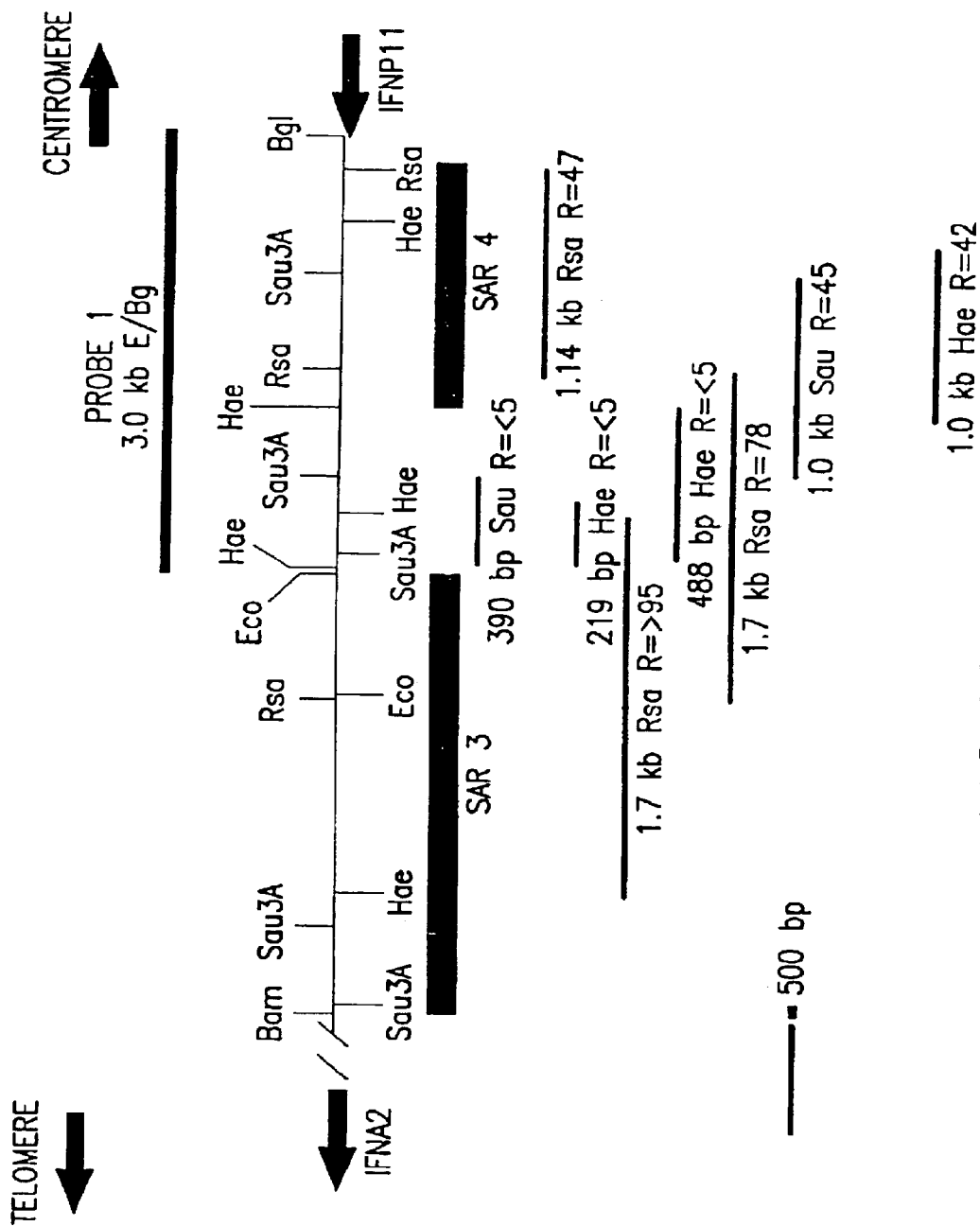

FIG. 20. Restriction enzyme map of SAR3 and SAR4 showing the location of pellet-enriched regions, weakly bound fragments, and supernatant-enriched regions. The 1.7-kb RsaI pellet-enriched fragment overlaps the previously identified pellet enriched 0.7-kb EcoRI fragment (probe k), thus confirming our earlier mapping of SAR3 (FIG. 19A and FIG. 19B). Supernatant enriched (219-bp HaeIII, 488-bp HaeIII, 390-bp Sau3A) and weaker binding fragments (1.0-kb Sau3AI, 1.0-kb HaeIII, and 1.14-kb RsaI) defined this region further into non-SAR fragments and the weak SAR4 respectively. Because the 488-bp HaeIII fragment (supernatant enriched) overlapped the telomeric end of the 1.0-kb Sau3A fragment by 300 bp, the remaining centromeric Sau3A. 700 bp should contain scaffold binding sites responsible for the weak binding pattern. In addition, the 1.14-kb RsaI fragment, and the 1.0-kb HaeIII appeared to bind weakly to scaffold proteins supporting the conclusion that weak binding sites map to the region of overlap between all three weak binding fragments (1.14 kb RsaI, 1.0 kb HaeIII, and 1.0 kb Sau3A. Bam=BamHI, Sau=Sau3A, Rsa=RsaI, Hae=HaeIII, BglII=BglII. Restriction fragments hybridized to probe 1 (3.0-kb EcoRI/BglII) are indicated in region below restriction map and SAR. R values are represented under the restriction fragments. Strong SAR=■ Weak SAR=□.

Figure 21:
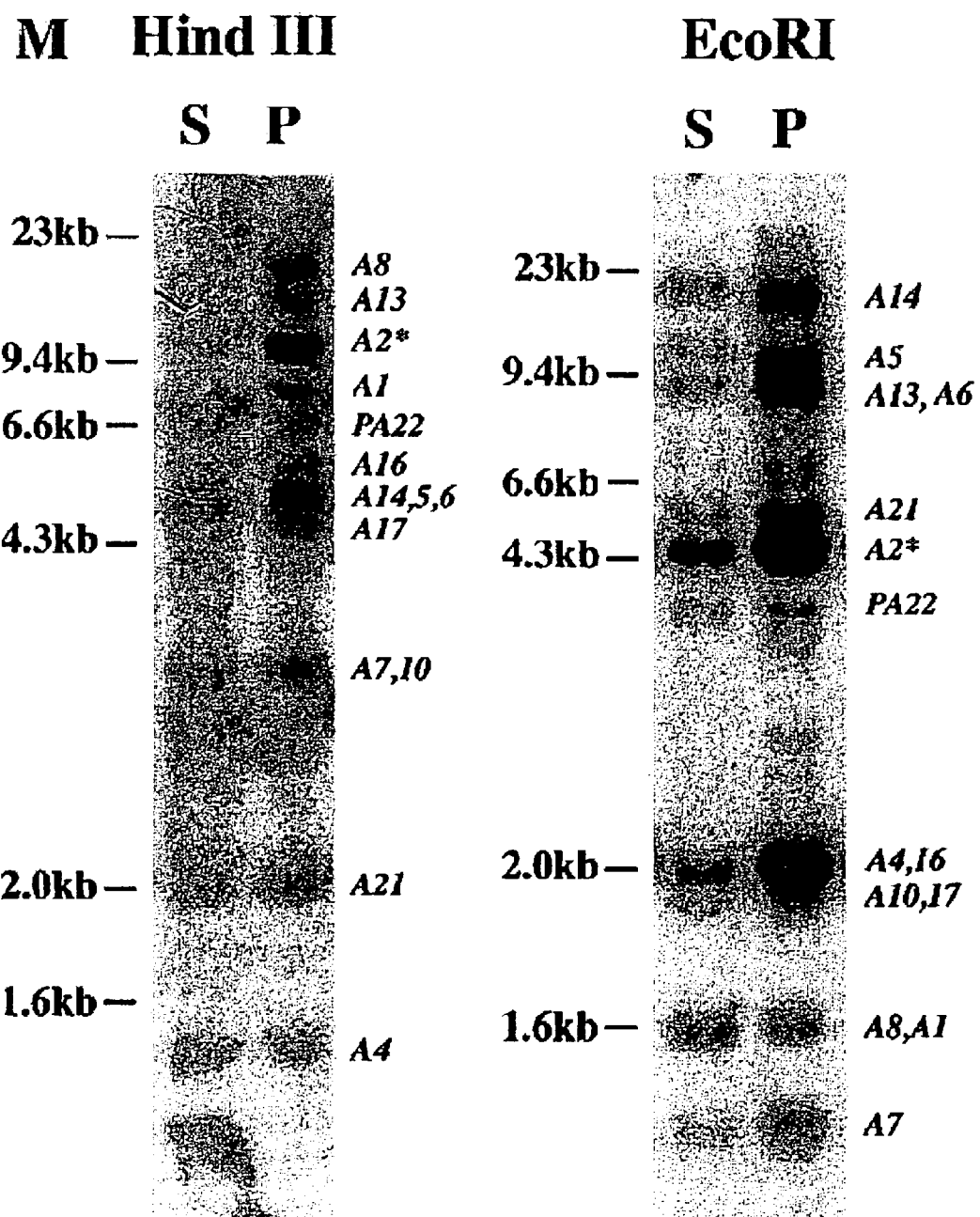

FIG. 21. U373 Southern blot results. From left to right the panels show results of the IFNA2 coding region hybridized to HindIII, and EcoRI supernatant and pellet fractions. Each IFNA fragment containing each gene member is identified to the right using the proper nomenclature. R values were measured and includes 16 different HindIII, EcoRI and BglII DNA fragments. These examples were chosen as representative examples showing supernatant, pellet and weak scaffold binding regions. M=λ phage HindIII markers. Some examples are the following: strong SARs on HindIII fragments (molecular weights are the same as in BV173), containing IFNA8 (R=71), IFNA4,6,10 (R=74); non-SARs with negligible binding containing IFNA1,8(R=23), and IFNA7(R=21).

4. DESCRIPTION OF ILLUSTRATIVE EMBODIMENTS

4.1 CDKN2

Even though there is great controversy regarding the role of CDKN2 in multiple cancers except melanoma, it is agreed that the 9p chromosome region harbors important gene(s) relevant to cancer because it is frequently deleted in cancer cells. The definition of the genetic lesions involved in oncogenesis has advanced through the identification of multiple dominant oncogenes and tumor suppressor genes. The present invention concerns in a general sense alterations in CDKN2, a gene involved in cell cycle control and any other 9p genes that may contribute to the malignant process in gliomas and other tumor types. In addition to improving the understanding of the basic mechanisms involved in gliomagenesis, the present invention also concerns improved strategies for prevention, diagnosis and treatment of this uniformly fatal cancer.

4.2 Human Gene Encoding MTAP

Many human malignant cells lack methylthioadenosine phosphorylase (MTAP) enzyme activity. The gene encoding this enzyme was previously mapped to the short arm of chromosome 9, band p21-$^2$2, a region that is frequently deleted in multiple tumor types. To clone candidate tumor suppressor genes (TSGs) from the deleted region on 9p21-22, a long range physical map of 2.8 megabases on 9p21 has been constructed using overlapping yeast artificial chromosome (YAC) and cosmid clones. This map includes the type I IFN gene cluster, the recently identified candidate TSGs, CDKN2 (p16$^{INK4A}$) and CDKN2B (p15$^{INK4B}$) as well as several CpG islands. In addition, other transcription units have been identified within the YAC contig.

Sequence analysis of a 2.5 kb cDNA clone isolated from a CpG island that maps between the IFN genes and CDKN2 reveals a predicted open reading frame of 283 amino acids followed by 1302 nucleotides of 3' untranslated sequence. This gene is evolutionarily conserved and shows significant amino acid homologies to mouse and human purine nucleoside phosphorylases as well as to a hypothetical 25.8 kDa protein in the pet genes (coding for cytochrome $bc_1$-complex) region of *Rhodospirillum rubrum*. The location, expression pattern and nucleotide sequence of this gene suggest that it codes for the MTAP enzyme.

4.3 Genetic Deletions in the 9p21 Region

Deletions of chromosomal band 9p21 have been detected in various tumor types as well as in more than 20% of acute lymphoblastic leukemia (ALL). These deletions frequently include the entire interferon (IFN) gene cluster as well as the methylthioadenosine phosphorylase (MTAP) gene. Recently, the CDKN2 gene (p16$^{INK4A}$, MTS I, CDK41) has been proposed as a candidate tumor suppressor gene on 9p21 because it is frequently deleted in cell lines derived from multiple tumor types. To determine if CDKN2 or another closely related gene on 9p is the target of 9p deletions in ALL and other hematological malignancies, 20 patient samples (13 ALL, 2 AML, 5 NHL) with 9p rearrangements were examined by Southern blot analysis, fluorescence in situ hybridization (FISH) and single-strand conformation polymorphism (SSCP) for alterations of CDKN2.

Homozygous deletions of the CDKN2 region were detected in 10 cases (50%): 6 ALL, 2 AML, 2 NHL. In one additional case the intensity of the Southern blot band was significantly reduced suggesting a CDKN2 deletion in a subpopulation of the malignant cells. The interferon (IFN) gene cluster was homozygously deleted in 2 of 15 (13%) analyzed cases, AITAP was deleted in 6 of 15 analyzed cases (40%). In addition, hemizygous deletions of the CDKN2 region were identified in 6 ALL cases by interphase FISH. No point mutation of the coding region of CDKN2 was detected by SSCP in the 6 cases with hemizygous deletions. It was concluded that CDKN2 is the most frequently homozygously deleted marker on 9p. The absence of point mutations in the coding region of CDKN2 in cases with hemizygous 9p deletions and the frequent co-deletion of MTAP and other yet unidentified neighboring genes suggest that the simultaneous deletion of these genes may be responsible for the selective growth advantage for the malignant cells.

4.4 Brain Tumors

Gliomas (a spectrum of tumors ranging from well differentiated low grade astrocytomas to high grade glioblastoma multiforme) constitute about 60% of all primary brain tumors. Brain tumors are the most common group of solid tumors of childhood, occurring in two age peaks; 3 yrs–12 yrs and 50 yrs–70 yrs (Díaz et al., 1990). Patients with low grade gliomas are usually curable while patients with glioblastoma multiforme have a median survival of less than 1 year even with the best conventional therapy of resection, followed by radiation therapy and chemotherapy. There is currently no uniform way of classifying these tumors or determining which tumors will progress rapidly. The lack of progress in diagnosing and treating this neoplasm is due in part to the lack of understanding of their basic biology. There is little understanding of the etiology, mechanisms responsible for tumor progression and response to therapy. Recent work on the molecular characterization of brain tumors highlight the importance of accumulation of genetic alterations in the progression of these tumors. Comparison of molecular, genetic and histopathologic analysis of glial tumors suggests specific associations between histologic types and genetic alterations. However, there is currently only a small database with which to evaluate such relationships. By studying these tumors at the molecular level, one may better understand their biology, which ultimately will lead to improved diagnosis and management of patients with gliomas and other cancers. Except for TP53 Cancer arises as a result of the accumulation of a series of genetic mutations which lead to progressive disorganization of the control mechanisms that normally limit cell growth and proliferation (National Center for Health Statistics, 1987).

Cytogenetic analysis of solid tumors has proven to be relatively difficult. Nonetheless, many of the genes cloned to date that are important in solid tumor progression have been isolated because their location was defined by recurring chromosome aberrations in the particular tumors or by linkage analysis in familial cases. Recent studies highlight the importance of tumor suppressor genes, including TP53, and RB1, in the development of solid tumors (Bigner et al., 1988; Kacker et al., 1990; Lukeis et al., 1990; Allegra, 1992; Cowan and Francke, 1992; Petty et al., 1993). Work has confirmed the view that carcinogenesis is a multistep process. In colon cancer, a number of the involved genes have now been cloned, including DCC, APC, MSH2, and MLHJ (Kacker et al., 1990; Lukeis el al., 1990).

There is paucity of information in the cytogenetic database on solid tumors but recent data indicate that unbalanced translocations or deletions of 9p with the shortest region of overlap (SRO) at 9p22 are recurring abnormalities in a gliomas as well as other tumor types such as melanoma, non-small cell lung cancer, head and neck cancer, mesothelioma, ovarian and breast cancers. By molecular analysis, homozygous deletions of DNA sequences on 9p or loss of heterozygosity has been described in a significant percentage of these tumors. The molecular studies in the different tumor types have demonstrated that these deletions involving 9p are sometimes submicroscopic and often include homozygous deletions of all or part of the interferon (IFN) gene cluster and the methylthioadenosine phosphorylase (ATAP) gene. Both the IFN gene cluster and MTAP gene have been mapped at 9p21-p22. The frequent occurrence of homozygous deletions in this chromosomal region strongly suggested the presence of a tumor suppressor gene (TSG), whose inactivation is involved in the diverse types of tumors. In addition, Cannon-Albright et al. reported on the linkage of a subset of familial melanoma to this locus on chromosome 9p (MLM), the same region that has been shown to be deleted in melanoma cell lines and primary tumors. It is proposed that this TSG(s) is likely to be important in the more general pathway of oncogenesis.

The introduction of a TSG (or a single normal chromosome carrying such a gene) into tumorigenic cells or the use of inter-specific and more recently, intra-specific human somatic cell hybrids provides a functional assay for the presence of TSGs (Diaz et al., 1990; Petty et al., 1993). Suggestion that there might be tumor suppressor activity on human chromosome 9 has been in the literature from as far back as 1975. Earlier work with somatic cell hybrids between mouse neoplastic cells and normal human fibroblasts, which segregate human chromosomes, showed that the human chromosome 9 is preferentially lost from tumorigenic hybrids, possibly indicating that hybrid cells which contain a normal human chromosome 9 can not form tumors in nude mice (Deville et al., 1991). A more recent report has also shown that after the introduction of human chromosomes 1, 6, 9, 11, and 19, only chromosomes 1, 6, and 9 were able to completely suppress tumorigenicity in a uterine endometrial adenocarcinoma cell line (Bieche et al., 1992). These studies support the hypothesis that tumor suppressor activity is present on human chromosome 9 and functions in a mouse background. The gene is also likely to function as a TSG in rat and mouse because tumor suppressor function have been previously mapped to rat chromosome 5 and mouse chromosome 4 in the region of synteny to human chromosome 9p, which maps around the IFN locus. The working hypothesis has been that the TSG(s) is closely linked to the IFN and ATAP genes on 9p (since retention of IFN genes and MATAP were sometimes observed despite deletion of DNA sequences on 9p) and that these genes are included in the deletions only as "innocent bystanders". One could not, however, completely exclude the IFN genes because of their negative role in growth regulation and suggested that they may play an accessory role in tumor suppression by this locus on 9p.

4.5 Regulation of Cell Proliferation

Regulation of cell proliferation appears to be a complex process involving the regulated expression and/or modification of discreet gene products, including that of inhibitory growth regulators such as secretory proteins like interferons and nuclear phosphoproteins like RB. Interferons inhibit cell proliferation and in many cases this inhibition is mediated by an autocrine pathway (Díaz et al., 1988). It has been proposed that IFN may participate in a feedback mechanism to regulate cell proliferation in adult tissues. Interferon induces RB expression in SW 480 (IFN transduced) colon cancer cell line but not in Daudi growth resistant and DU-145 RB(−) cell line. Interferons have also been shown to down-regulate MYC expression which is thought to be mediated by RB protein interaction with the MYC promoter in Daudi cells. Interferon has also been shown to down regulate SRC and RAS in RT4 bladder cancer cell line. Moreover, the interferon inducible proteins implicated in tumor suppression include the interferon regulatory factors, IRF-1 and IRF-2, a double stranded RNA-activatable protein kinase and RNase L, a latent endoribonuclease to mention a few. The deletion of IFN genes may therefore lead to the deregulation of cell proliferation, giving rise to clonal expansion of the mutated cell.

MTAP on the other hand is a gene that codes for an enzyme involved in the metabolism of polyamines and purines. This enzyme is present in all normal tissues and in cell lines derived from normnal cells but is deficient in cell lines established from leukemias, lymphomas, and solid tumors such as melanoma, breast cancer, squamous cell lung cancer and rectal adenocarcinoma. In mammalian cells, methylthioadenosine (MTA), the substrate for MTAP is produced during synthesis of polyamines from decarboxylated S-adenosylmethionine. MTA does not accumulate in normal tissues but is cleaved rapidly to adenine and 5'-methylthioribose 1-phosphate (MTR-1-P) by MTAP. The adenine is recycled to purine nucleotides via adenine phosphoribosyltransferase. MTAP deficiency, by decreasing adenine formation, would be expected to interfere with this salvage pathway by decreasing adenine formation. On the other hand, MTR-1-P is converted to methionine, which may also be synthesized from homocysteine by methionine synthase and betaine-homocysteine methyltransferase. In MTAP deficient cells, however, methionine is synthesized solely from homocysteine. Accordingly, MTAP deficient malignant cells might become more dependent than normal cells on an exogenous supply of methionine. Thus, MTAP deficiency in human malignancy may permit the development of enzyme-selective chemotherapy agents in which enzyme-negative cancer cells will be killed with drugs causing the depletion of purine nucleotides or methionine, under conditions in which enzyme-positive normal cells can be rescued by giving MTA as a source of purines or methionine. This major difference between normal and malignant cells might be used to design more effective chemotherapy approaches in gliomas and other solid tumors where there are currently no effective therapy.

4.6 Western Blots

The compositions of the present invention will find great use in immunoblot or western blot analysis. Anti-MTAP antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

4.7 Vaccines

The present invention contemplates vaccines for use in both active and passive immunization embodiments. Immunogenic compositions, proposed to be suitable for use as a vaccine, may be prepared most readily directly from immunogenic MTAP peptides prepared in a manner disclosed herein. Preferably the antigenic material is extensively dialyzed to remove undesired small molecular weight molecules and/or lyophilized for more ready formulation into a desired vehicle.

The preparation of vaccines which contain MTAP peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1 to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10 to about 95% of active ingredient, preferably about 25 to about 70%.

The MTAP and MTAP-derived peptides of the present invention may be formulated into the vaccine as neutral or salt forms. Pharmaceutically-acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable oil vehicles such as mannide monooleate (Aracel-A®) or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

4.8 DNA Segments

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a MTAP peptide in its natural environment. Such promoters may include promoters normally associated with other genes, and/or promoters isolated from any viral, prokaryotic (e.g., bacterial), eukaryotic (e.g., fungal, yeast, plant, or animal) cell, and particularly those of mammalian cells. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter/expression systems contemplated for use in high-level expression include, but are not limited to, the Pichia expression vector system (Pharmacia LKB Biotechnology), a baculovirus system for expression in insect cells, or any suitable yeast or bacterial expression system.

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of MTAP peptides or epitopic core regions, such as may be used to generate anti-MTAP antibodies, also falls within the scope of the invention. DNA segments that encode MTAP peptide antigens from about 10 to about 100 amino acids in length, or more preferably, from about 20 to about 80 amino acids in length, or even more preferably, from about 30 to about 70 amino acids in length are contemplated to be particularly useful.

In addition to their use in directing the expression of MTAP peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least an about 14-nucleotide long contiguous sequence that has the same sequence as, or is complementary to, an about 14-nucleotide long contiguous DNA segment of SEQ ID NO:1 will find particular utility. Longer contiguous identical or complementary sequences, e.g., those of about 20, 30, 40, 50, 100, 200, 300, 500, 1000, (including all intermediate lengths) and even those up to and including about 1118-bp (full-length) sequences will also be of use in certain embodiments.

The ability of such nucleic acid probes to specifically hybridize to MTAP-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 14, 15–20, 30, 40, 50, or even of about 100 to about 200 nucleotides or so, identical or complementary to the DNA sequence of SEQ ID NO:1, are particularly contemplated as hybridization probes for use in, e.g., Southern and Northern blotting. Smaller fragments will generally find use in hybridization embodiments, wherein the length of the contiguous complementary region may be varied, such as between about 10–14 and up to about 100 nucleotides, but larger contiguous complementarity stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 15 to about 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as PCR™, by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating MTAP-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Segal, 1976; Prokop, 1991; Kuby, 1994; and Maloy et al., 1994, are particularly relevant.

Of course, for some applications, for example, where one desires to prepare mutants employing a mutant primer strand hybridized to an underlying template or where one seeks to isolate MTAP-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/ biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

4.9 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the data shown in Table 1.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CCA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | USG | | | | |
| Tyrosine | Tyr | Y | UAC | UAU | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

4.10 Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

4.11 Monoclonal Antibodies

Means for preparing and characterizing antibodies are well known in the art (See, e.g., Harlow and Lane, 1988; incorporated herein by reference).

The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified MTAP or MTAP-related protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Campbell, 1984; Goding, 1986). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (vol/vol) PEG, by Gefter et al., (1977). The use of electrically induced fusion methods is also appropriate (Goding, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

4.12 Pharmaceutical Compositions

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus by additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The following examples are included to demonstrate preferred embodiments of the invention. It should be appreciated by those of skill in the art that the techniques disclosed in the examples which follow represent techniques and methods contemplated to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5. EXAMPLES

5.1 Example 1

Construction of a 2.8 Mb YAC Contig and Cloning of the Human MTAP Gene From the Tumor Suppressor Region on 9p21

This example describe the construction of a long range physical map around the IFN gene cluster which covers a distance of 2.8 Mb as determined by pulsed-field gel electrophoresis and also the isolation of the MTAP gene cDNA. All of the known genes were localized as well as several CpG islands on this map. Restriction sites and pulsed field fragment sizes are clearly delineated on the resultant map which extends further proximally than the one previously presented (Weaver-Feldhaus et al., 1994) In addition, several new markers are described and localized on this map. The approximate location of the shortest region of overlap of 9p deletions in gliomas, melanomas, lung cancer, leukemia, mesothelioma, head and neck cancer and bladder cancers in relation to this map is indicated.

5.1.1 Materials and Methods 5.1.1.1 Cell Lines

The clinical and cytogenetic characterization of the tumor cell lines used in this study have been previously published (Olopade et al., 1992; 1993). Cell lines were used for the deletion mapping because they provide an indefinite supply of DNA and because it had previously been shown that the deletions present in cell lines were similar to the deletions observed in primary leukemias and gliomas. (Díaz et al., 1988; 1990; Olopade et al., 1992).

5.1.1.2 Analysis of YAC Clones

YAC clones corresponding to IFNA1 (Kwiatkowski and Diaz, 1992; Díaz et al., 1994) and D9S966 (Bohlander et al., 1994) STSs were isolated from the CEPH MegaYAC library. High-molecular-weight YAC DNA was isolated digested, electrophoresed and blotted as previously described (Díaz et al., 1994). To detect the left and right YAC vector arms, a 346 bp HindIII-BamHI and a 276-bp BamHI-SalI restriction fragment from the plasmid pBR322 were used respectively. Other probes used are as described in FIG. 1. The DNA probes were labeled with [$\alpha$-$^{32}$P]dATP using the random primer labeling technique (Feinberg and Vogelstein, 1983). PCR™ of the STSs was performed with 50 ng of YAC or human genomic DNA as template using standard PCR™ conditions.

5.1.1.3 Fluorescence In Situ Hybridization (FISH) Analysis

YAC clones were purified by pulsed field gel electrophoresis and the DNA was amplified using a sequence-independent amplification technique (Bohlander et al., 1994). The amplification products were then labeled with biotin-11-dUTP, or directly labeled nucleotides (spectrum-orange™, VYSIS), and FISH was performed as previously described (Rowley et al., 1990).

5.1.1.4 Cloning YAC End-Specific Clones

To obtain YAC end specific probes, YAC end rescue was performed as described (Hermanson et al., 1991). Single copy fragments from the YAC end rescued inserts were used as probes for Southern hybridization to DNA of the different YACs as well as to a panel of tumor cell lines. Each end clone probe was also used to screen a copy of the Lawrence Livermore Laboratory chromosome 9 flow-sorted cosmid library. The overlap between YACs was identified by comparing Southern blots after hybridization to the IFNA2 gene probe which cross hybridizes to a large number of IFN genes, and after hybridization to the different end clone probes. YACs were also aligned by comparison of their long range restriction maps.

5.1.1.5 Screening for Expressed Sequences

The cosmids obtained using probes from this ordered YAC contig were used for several different strategies to detect expressed sequences including direct screening of cDNA libraries, exon trapping, and a cDNA selection protocol based on the capture of sequence independently amplified cosmid fragments by biotinylated cDNA (Buckler et al., 1991; Lovett et al., 1991). Exon trapping was performed according to the manufacturer's protocol using the Exon Trapping kit (Life Technologies, Inc., Gaithersburg, Md.). Each exon-trapped product or cDNA selected fragment from the cosmids was hybridized to a multiple tissue Northern blot (Clontech, Palo Alto, Calif.), a somatic cell hybrid panel (Oncor, Gaithersburg, Md.), "zoo blots" (Bios, New Haven, Conn.) and Southern blots of tumor cell lines. Products that detected transcripts on Northern analysis were used to screen cDNA libraries from human adult brain, fetal brain and fibroblast constructed in λgt10 or λgt11 (Clontech). In each case, approximately $7.5 \times 10^5$ plaques were screened. Positive clones were subcloned into the pBluescript vector (Stratagene, La Jolla, Calif.) for sequencing.

5.1.1.6 Nucleotide Sequencing and Generation of STSs

Sequencing was performed on an ABI model 373A DNA sequencing system with the PRISM Ready Reaction Dye-Deoxy Terminator Cycle sequencing kit (Applied Biosystems). cDNA clones were sequenced entirely on both strands using double stranded templates. The DNA sequence and the predicted open reading frame were compared with GenBank databases by using the BLASTN and BLASTP programs (Altschul et al., 1990).

5.1.2 Results 5.1.2.1 Construction of the Physical Map

Fifteen YAC clones were identified after screening the CEPH MegaYAC library with the IFNA and D9S966 STSs. Five clones (33%) were found to be non chimeric by FISH analysis and were further analyzed. Two YAC clones (YAC 802B11 and 886F9) contain the entire IFN gene cluster whereas the remaining three YAC clones (883G5, 942A3, and 807E4) contain D9S966. YACs A73B12 and A88E10 were obtained with consensus IFNSTS from the St Louis YAC Library (Díaz et al., 1994). The YACs were digested with the rare cutting restriction endonucleases NoiI, SacII, SalI, and SfiI. After pulsed-field gel electrophoresis, and Southern transfer, the blots were hybridized to a battery of probes including the IFNA, IFNBI, the left and right vector arm probes, D9S966, six end probes and the CDKN2 cDNA probe. The resulting map is shown in FIG. 1. The IFN genes contained within YACs 802B11 and 886F9 were identified and aligned with the previous map of the IFN gene cluster (Díaz et al., 1994). Except for YAC 886F9, none of the YACs demonstrated any unusual deletions or rearrangements as determined by STS content. The 886F9 YAC published previously (Weaver-Feldhaus et al., 1994) is larger and extends further centromeric than the clone isolated, suggesting that this YAC may have undergone an internal deletion. However, the STS content of the remaining human insert was consistent with the other IFN-derived YACs. To characterize the YAC clones further, single copy DNA fragments obtained from the YAC end clones were used as probes on Southern hybridization. The results are included in FIG. 1. Each end clone probe mapped back to the respective YACs and to chromosome 9 by FISH analysis. This map does not show every restriction site for the enzymes SalI, SacII, and SfiI because sites that are further away from the probes used were not detected. However, several CpG islands can readily be identified on this map.

5.1.2.2 Deletion Mapping Analysis

Each unique fragment from the end-clones and additional STSs were tested on a panel of cell lines to refine the deletion map. The results are summarized in Table 2. Homozygous deletion of at least one marker derived from this YAC contig was detected in 69% of glioma cell lines, 45% of melanoma cell lines, 50% of bladder cancer cell lines, 89% of leukemias, 100% of mesotheliomas, 38% of head and neck cancer and 34% of lung cancer cell lines. The majority of the cell lines had large homozygous deletions which overlapped around CDKN2/CDKN2B.

It had previously been shown that the deletion in Hs294T, a melanoma cell line could not be complemented by introducing a chromosome 9 derived from the T98G cell line by microcell chromosome transfer. However, introducing a normal short arm of chromosome 9 derived from a human fibroblast cell line induced senescence in Hs294T (Porterfield et al., 1992). The region deleted in Hs294T is flanked by D9S736 and D9S966. In T98G, the homozygous deletion is flanked by MTAP and CDKN2B. Therefore, a region of approximately 100 kb was defined by the overlapping homozygous deletions in these two cell lines. Thus, it was possible to define a shortest region of overlap (SRO) of these 9p deletions to the region between the 3' end of MTAP and CDKN2B. From Table 2, it is apparent that the pattern and percentage of 9p homozygous deletions differ in different tumor types. For example, in melanomas, mesotheliomas and head and neck cancers, the deletions rarely extend into the IFN gene cluster, whereas the IFN genes are included in 27–44% of the deletions in leukemias, bladder cancer and gliomas. Moreover, MTAP is homozygously deleted with the same frequency as CDKN2 in some tumor types.

TABLE 2

Homozygous Loss of 9p Markers in Tumor Cell Lines

| Cell type (n) | % cell lines test showing homozygous deletions | | | | | | |
|---|---|---|---|---|---|---|---|
| | IFNB1 | IFNA | D9S736 | M1.4 | CDKN2 | CDKN2B | D9S966 | D9S171 |
| Leukemia (18) | 39 | 44 | ND | 65 | 89 | 78 | 44 | 6 |
| Melanoma (18) | 0 | 0 | 0 | ND | 45 | 45 | 15 | 0 |
| Glioma (26) | 27 | 42 | 42 | 63 | 69 | 65 | 42 | 12 |
| Bladder (16) | 0 | 31 | ND | 50 | 50 | 50 | 44 | ND |
| Head and neck (8) | 0 | 0 | 0 | 0 | 38 | 25 | 0 | ND |
| Lung (58) | 6 | 8 | ND | 34 | 34 | 29 | 5 | 2 |
| Mesothelioma (5) | 0 | 0 | 0 | 100 | 100 | 100 | 40 | 20 |

Homozygous deletion of these markers were detected by Southern blot analysis or STS-PCR ™.
The location of the markers are shown in FIG. 1. ND, not done; M1.4, 1.4-kb fragment from the 3' untranslated portion of the MTAP gene.

The following markers were not present in the YAC contig: D9S3, D9S126, D9S171, D9S162, D9S962 (MDS10), D9S963 (MDS36), and an STS from the D9S171 YAC which maps at least 500 kb telomeric of D9S171. It was possible to localize D9S736 within YACs 802B11 and YAC 886F9 in a 170 kb SalI-SfiI fragment centromeric to the IFN gene cluster and close to the right end of YAC 886F9; 1063.7 was present in YAC 807E4 only and c1.b in YACs 942A3 and 807E4. (FIG. 1) (Kamb et al., 1994; Weaver-Feldhaus et al., 1994). Because the distance from the IFN gene cluster to the centromeric end of this YAC contig is 1.8 Mb, D9S171 should be a minimum distance of 2.3 Mb from the centromeric end of the IFN gene cluster; and D9S736 should be at least 2.0 Mb from D9S171. This is consistent with previous estimates. D9S736 has been estimated to be 2 cM from D9S171 (Weaver-Feldhaus et al., 1994), whereas D9S126 was estimated to be at a minimum distance of 1.0 Mb from the IFN gene cluster (Fountain et al, 1992).

5.1.2.3 Expressed Sequences Within and Around the SRO

An 85-bp exon trapped product obtained from a cosmid which maps in the CpG island at the right end of YAC 886F9 was used to screen a cDNA library. One of the clones, a 2.5-kb cDNA detects 2 major transcripts, of about 2.3 kb and 6.0 kb as shown in FIG. 2A and FIG. 2B. This gene is expressed to varying degrees in all tissue types and is conserved in all mammalian species as judged by zoo-blot hybridization. The nucleotide sequence (FIG. 3A) (SEQ ID NO:1) reveals an open reading frame (ORF) coding for 283 amino acids (FIG. 3B) (SEQ ID NO:2) which included the initiator methionine codon. The protein sequence shows homology to the human, mouse, and bacteria purine nucleoside phosphorylase gene (PNP), as well as to a hypothetical 25.8 kDa protein in the pet genes (coding for cytochrome $bc_1$-complex) region of *Rhodospirillum rubrum*, and also to a recently described ORF from *S. cerevisiae*. MTAP is a PNP but has different substrate specificity than the PNPs that have been cloned at present. The region of homology to the 25.8 kDa protein is distinct from the region of homology to the purine nucleoside phosphorylases with only a minor overlap.

The presence or absence of a 1.4 kb subclone of the cDNA (probe M1.4, FIG. 4) was correlated with the presence or absence of MTAP enzyme activity in previously characterized cell lines (Olopade et al., 1992; 1993). This 1.4-kb probe is deleted in every cell line which lack no MTAP enzyme activity and is present in all cell lines with MTAP enzyme activity. When the 1.1-kb, 5' fragment of the cDNA probe (M1.1, FIG. 4) was used for Southern blot analysis of PstI digested human genomic DNA, four bands were seen. One of these bands was always seen in cell lines with homozygous deletions of the 9p21 region. The M1.1 probe was then used on a somatic cell hybrid panel, and found to hybridize only to human chromosomes 9 and 3. Thus, it appears that another gene or pseudogene homologous to AITAP maps to human chromosome 3.

5.1.3 Discussion

The MTAP gene was previously localized using somatic cell hybrids (Carerra etal., 1984). The location was refined using information obtained by performing pulsed field gel electrophoresis in cell lines (Díaz et al., 1988; Olopade et al., 1992). Because there was no probe available for the AITAP gene, it was concluded that the putative TSG must lie between the IFN gene cluster and the MTAP gene. Using similar reasoning, Coleman et al. (1994) placed the SRO in melanomas centromeric to the AITAP gene and suggested that the SRO in melanoma was distinct from the SRO in gliomas, leukemias and lung cancers. Barring any complex rearrangements in both T98G (glioma) and Hs294T (melanoma), the position of the TSG should be within the region defined by the homozygous deletions in these two cell lines. This region maps centromeric to MTAP and the IFN gene cluster but distal to D9S966 and includes CDKN2 (FIG. 1). This region corresponds to the only critical region defined using primary samples from patients with gliomas and leukemias (Dreyling et al., 1995). The region overlaps the MLM locus because it maps in the 2 cM region between D9S736 and D9S171 (Cannon-Albright et al., 1984; Povey et al., 1994). These data are consistent with recent published results (Jen et al., 1994) in which a high frequency of homozygous deletions of CDKN2 and CDKN2B was found in primary glioma samples. No point mutations of either gene were observed in primary gliomas.

The long range map covers 2.8 megabases including the IFN gene locus but does not reach D9S126 or D9S171. There are now 2 reports of homozygous deletions on 9p that do not extend into the CDKN2 locus (Cheng et al., 1994; Lydiatt et al., 1994). In fact, these two reports suggest that one of the other 9p TSGs is telomeric to CDKN2. To date, all the data available so far in primary tumors and tumor cell lines, suggest that the preferred mechanism for gene inactivation on 9p is homozygous deletion rather than point mutations. No other chromosomal region is known with such a high frequency of homozygous deletions. It is rather intriguing that all of the genes (the IFN gene cluster, MTAP, CDKN2 and CDKN2B) identified thus far in this region could have some significant biological role in cancer. The most efficient way to inactivate all of these genes if they are biologically important would be by a large enough deletion. Alternately, these genes may have been deleted as "innocent bystanders" because intrinsic fragility or recombinogenicity around the TSG may make the region a hot spot for illegitimate recombination.

The inclusion of MTAP gene in these deletions may present an opportunity to use this phenomenon in drug development (Carerra et al., 1984; Della Ragione et al., 1992; Nobori et al., 1993). MTAP is involved in the purine salvage pathway in which methylthioadenosine is recycled to the purine nucleotide pool. MTAP deficiency interferes with this salvage pathway. MTAP deficiency in human malignancy may permit the development of chemotherapeutic approaches in which MTAP-negative cancer cells will be selectively killed with drugs causing the depletion of purine nucleotides. This major difference between normal and malignant cells may be used to design more effective chemotherapy approaches in gliomas, lung cancer and other solid tumors where there are currently no effective therapies.

5.2 Example 2

Mapping of Genomic Rearrangements Involving the Short Arm of Chromosome 9 in ALL and Other Hematologic Malignancies 5.2.1 Material and Methods 5.2.1.1 Patients The karyotypes of patients with hematological malignancies referred to the Cytogenetic Hematology/Oncology. Laboratory of the University of Chicago Medical Center between 1989 and 1994 were reviewed. Twenty cases with cytogenetic rearrangement of the short arm of chromosome 9 in at least 30% of the metaphase cells analyzed and for which material were available were selected. Cytogenetically, 7 cases had a rearrangement that involved no loss of band 9p21, 9 cases retained one copy and 4 cases had homozygous deletions of chromosomal band 9p21. Each case (13 ALL, 2 AML, 5 NHL) was classified according to the criteria of the French-American-British (FAB) classification for leukemias or the working formulation for the non-Hodgkin's lymphomas (Non Hodgkin's Lymphoma Pathologic Classification Project, 1982; Bennett et al., 1976). Table 3 shows the clinical characteristics of the study patients.

TABLE 3

Characterization of Patient Material

| Case No. | Sex/Age (yr) | DX | Stage | Chromosomal Abnormalities of 9p | Copies of 9p21* | % of Abnormal Clone | Sample |
|---|---|---|---|---|---|---|---|
| 1 | M/33 | B-ALL | DX | t(2;9)(p12;p23) | 2 | 83 | BM |
| 2 | M/28 | B-ALL | DX | dic(9;12)(p1?3;p1?2) | 1 | 15 | BM |
|   |      |       |    | dic(9;12)(p1?3;p1?2),del(9)9p13p22) | 0 | 36 |   |
| 3 | M/36 | B-ALL | RL | t(3;9)(q29;p13) | 2 | 100 | PB |
| 4 | F/66 | B-ALL | RL | der(9)t(8;9)(q11;p13) | 1 | 40 | BM |
| 5 | M/67 | B-ALL | DX | der(9)t(4;9)(p1?4;p2?1) | 1 | 100 | BM |
| 6 | F/14 | B-ALL | RL | der(9)t(9;?9)(p1?2;q22) | 1 | 82 | BM |
| 7 | M/26 | B-ALL | DX | der(9)t(9;17)(p13;q11) | 1 | 49 | BM |
| 8 | F/2 | T-ALL | DX | del(9)(p2?1p24) | 1 | 83 | BM |
| 9 | F/50 | B-ALL | DX | dic(9;19)(p11;p13) | 1 | 90 | BM |
| 10 | M/28 | B-ALL | RL | add(9)(p24) | 2 | 84 | BM |
| 11 | F/24 | B-ALL | DX | −9 | 1 | 40 | BM |
|   |   |   |   | −9,del(17)t(9;17)(p13;p11) | 2 | 51 |   |
| 12 | M/17 | B-ALL | DX | dic(7;9)(p1?3;p1?1), t(9;11)(p13;p11) | 1 | 100 | BM |
| 13 | F/17 | B-ALL | DX | del(9)(p13p23) | 1 | 63 | BM |
| 14 | F/85 | AML | DX | −9, add(9)(p13q34) | 0 | 100 | PB |
| 15 | M/69 | AML | DX | dic(5;9)(p15;p13), dic(9;?;16;?) (9qter→9p13::?::16p11→16q22::?), +del(9)t(9;19)(p11;q11) | 0 | 100 | BM |
| 16 | F/42 | NHL, dl | DX | −9, −9, dic(2;9)(p2?3;p2?4), der(9)(p11;q13)† | 1 | 73 | TU |
| 17 | M/64 | NHL, fl | DX | der(9)t(4;9)(q21;p22)del(4)(q31q33) | 2 | 80 | LN |
| 18 | M/59 | NHL, dl | DX | t(9;19)(p13;q13.3) | 2 | 30 | LN |
| 19 | M/69 | NHL, dl | DX | add(9)(p13or21), der(9)t(5;9)(q11;p12) | 0 | 85 | LN |
| 20 | M/48 | NHL, fl | DX | der(9)t(1;9)(q21;p23)×2† | 4 | 50 | LN |

Abbreviations: DX, diagnosis; RL, relapse; dl, diffuse large-cell subtype; fl, follicular large-cell subtype; BM, bone marrow; PB, peripheral blood; TU, tumor; LN, lymph node.
*Number of copies of chromosomal band 9p21 based on cytogenetic analysis.
† Near tetraploid karyotype.

5.2.1.2 Southern Blot Analysis

High molecular weight DNA was isolated as previously described (James et al., 1988). DNA was digested with the restriction enzyme HindIII, electrophoresed on a 1% agarose gel, and transferred to a nylon-based nitrocellulose membrane (Gene Screen plus, NEN, Boston, Mass.). DNA filters were hybridized with 32P-labeled probes from 9p21 and exposed to X-ray film. The chromosomal localization of the 9p probes is shown in FIG. 5. Probe M1.4 represents the 3' untranslated region of MTAP described in Example 1 which is located approx. 100 kb telomeric to CDKN2. D9S966 is 200 kb centromeric to CDKN2 (Bohlander et al., 1994). CDKN2 (cDNA) and CDKN2B (p15) (exon 1) are located within 20 kb of one another (Kamb et al., 1994). Equal DNA loading was verified by visual inspection of ethidium bromide-stained gels and by control hybridizations to a transferrin receptor probe located on chromosome 3 (Schneider etal., 1984).

5.2.1.3 FISH Analysis

Mononuclear cells of patients samples, normal bone marrow and peripheral blood cells had been grown in short term culture, harvested using standard cell culture techniques and stored in fixative for several years (Le Beau, 1994). YAC A88E10 (330 kb), later referred to as YAC 11, was obtained by screening the St. Louis library with IFN A1 primers (Henco et al., 1988). The contig of 8 cosmids encompassing a 250-kb region around CDKN2 (COSp16) was assembled by screening a flow-sorted human chromosome 9 library (Lawrence Livermore Laboratories) with probes from a YAC contig of the region. A similar cosmid contig probe identified all homozygous deletions in leukemia derived cell lines (Dreyling et al., 1994).

YAC 284D6 (320 kb), later referred to as YAC 10/2, from chromosomal band 8q22 was used as a control probe (Erickson et al., 1992). pHuR98, a variant satellite 3 sequence from the centromere of chromosome 9, was used to determine the copy number of this chromosome (Moyzis et al., 1987). FISH probes were prepared using sequence-independent amplification (SIA) as previously described (Bohlander et al., 1992; 1994). The copy number of chromosome 8 was determined by a centromeric FISH probe CEP 8 Spectrum Orange (Imagenetics, Framingham, Mass.). Two-color FISH with a YAC or cosmid probe and a centromeric probe was performed as previously described (Rowley et al., 1990). Briefly, the hybridization solution contained approx. 0.1 mg of each probe, 1 μg human Cot1-DNA (BRL), 0.6 μg human placental DNA and 3 pg salmon sperm DNA/slide in a 10 μl volume. The biotinylated probes were detected with fluorescein isothiocyanate (FITC)-conjugated avidin. The slides were counterstained with 4',6'-diamidino-2-phenylindole dihydrochloride, and were analyzed using epifluorescence and a single pass filter (Chroma Technology) to avoid superimposition of the centromeric and the cosmid signals.

For each case, 250 single, intact interphase cells were analyzed. Separate gray scale images of DAPI-stained cells and fluorescence signals were captured using a cooled charge-coupled device (CCD) camera (Photometrics, Tucson, Ariz.) and were merged using NIH Image (NIH, Bethesda, Md.) or Adobe Photoshop (Adobe Systems, Mountain View, Calif.).

5.2.1.4 SSCP Analysis

Cases with hemizygous deletions of the CDKN2 gene were analyzed by SSCP. HL60, a myeloid cell line with known point mutation in exon 2 (nucleotide 232: C→T), was included as a positive control (Nakarnake et al., 1994). CDKN2 exons 1 and 2 were radiolabeled with $^{32}$P-dCTP by PCR™ using primers 2F and 1108F or 42F and 551R as described previously (Kamb et al., 1994). The amplification product was digested with SacII and ApaLI, respectively, denatured and run on a 40% polyacrylamide gel under 3 different conditions (room temperature, with 10% Glycerol, and at 4° C.).

5.2.2 Results 5.2.2.1 Southern Blot Analysis

In 15 cases DNA was available for Southern blot analysis. Homozygous deletions on 9p were detected in 8 cases (5 ALL, 1 AML, 2 NHL). M1.4 was deleted in 6 cases (40%), CDKN2 and CDKN2B in 8 cases (53%), and D9S966 in 7 cases (47%) (Table 4, FIG. 6A, FIG. 6B, FIG. 6C, FIG. 6D, and FIG. 6E). Patient 3 had the smallest deletion which included CDKN2 and CDKN2B, but did not involve the flanking molecular markers. In comparison, cytogenetic analysis detected homozygous deletions of 9p21-22 in only two cases (Patent No. 15 and Patent No. 19), loss of one allele in five cases, and no loss of 9p21 in one of the 8 cases with homozygous 9p deletions detected by Southern blot. Thus, in the majority of cases the deletion was submicroscopic in one of the chromosome 9 homologues.

One case showed a significant reduction in the intensity of the Southern blot bands (Patient No. 2). Only 51% of the metaphase cells from the bone marrow had a clonal abnormality of 9p. Thus, the Southern blot data likely represents a homozygous CDKN2 deletion in a subpopulation of cells. However, the Southern blot data is also compatible with a hemizygous deletion in the vast majority of the malignant cells. Unfortunately, there was no material available for FISH analysis.

showed homozygous deletions on Southern blot analysis (Table 4). Two of the patients had material for FISH studies but not for molecular studies. Cytogenetic analysis detected homozygous deletions of 9p21-22 in three cases and loss of only one allele in three of the 6 cases with homozygous 9p deletions detected by FISH (Table 4). However, in all samples, the percentage of cells with 9p deletions detected by FISH correlated closely with the percentage of metaphase cells with 9p rearrangements detected by cytogenetic analysis. In the cases with homozygous 9p deletion, 87.7±7.3% of the cells showed no COSp16 signal, while 94.3±2.7% of the cells retained all copies of the control YAC on chromosome 8 (FIG. 7A). Interphase FISH with COSp16 identified all homozygous deletions detected by molecular analysis. However, four cases with homozygous deletion detected by Southern blot had no material available for FISH studies. Both copies of the IFN region (YAC 11) were deleted in 2 ALL cases.

Hemizygous deletions of the CDKN2/CDKN2B region were detected by interphase FISH in 6 ALL cases (FIG. 7B). Cytogenetic analysis had predicted a loss of one copy of chromosomal band 9p21 in 4 of these cases and no loss of 9p21 in 2 cases (Table 4). These hemizygous deletions could not be detected by Southern blot analysis, probably because only subpopulations of cells (43–86% of interphase cells) were involved. In addition, molecular analysis did not detect any homozygous deletion of other markers of the region (M1.4 or D9S966) in these cases.

TABLE 4

Southern Blot, FISH, and SSCP Analysis of Hematologic Malignancies

| {PRIVATE} Case No. | DX | Cytogenetic Analysis | M1.4 | CDKN2 | CDKN2B | D9S966 | YAC11 (FISH) | COSp16 (FISH) | SSCP CDKN2 |
|---|---|---|---|---|---|---|---|---|---|
| 1 | ALL | + | + | + | + | + | + | H | N |
| 2 | ALL | –† | +* | +* | +* | +* | ND | ND | ND |
| 3 | ALL | + | + | – | – | H | ND | ND | ND |
| 4 | ALL | H | + | + | + | + | H | H | N |
| 5 | ALL | H | – | – | – | – | – | – | ND |
| 6 | ALL | H | + | + | + | + | H | H | N |
| 7 | ALL | H | ND | ND | ND | ND | H | H | ND |
| 8 | ALL | H | ND | ND | ND | ND | H | – | ND |
| 9 | ALL | H | + | + | + | + | H | H | N |
| 10 | ALL | + | ND | ND | ND | ND | H | H | N |
| 11 | ALL | +† | – | – | – | – | ND | ND | ND |
| 12 | ALL | H | – | – | – | – | – | – | ND |
| 13 | ALL | H | + | – | – | – | ND | ND | ND |
| 14 | AML | — | ND | ND | ND | ND | H | — | ND |
| 15 | AML | – | – | – | – | – | H | – | ND |
| 16 | NHL | H | – | – | – | – | ND | ND | ND |
| 17 | NHL | + | + | + | + | + | + | + | ND |
| 18 | NHL | + | ND | ND | ND | ND | + | + | ND |
| 19 | NHL | – | – | – | – | – | H | – | ND |
| 20 | NHL | + | + | + | + | + | + | + | ND |

Abbreviations: Dx, diagnosis; +, no deletion; –, homozygous deletion; H, hemizygous deletion; +*, Southern blot bands of reduced intensity; N, normal (no point mutation); ND, not done.
† Analysis of largest subclone.

5.2.2.2 Interphase FISH Analysis

To determine the reliability of the FISH probes used in this study ten test hybridizations of peripheral blood cells and five hybridizations of bone marrow cells from normal individuals were performed with each probe. Both cosmid contig and YAC probes showed an almost identical distribution of signals/cell comparable to previously published results for centromeric probes. In 500 nuclei scored, 2 signals were detected in 94–97% of the cells.

Interphase FISH analysis was performed on 15 patient samples. Homozygous deletions of COSp16 were detected in 6 cases (3 ALL, 2 AML, 1 NHL), four of whom also Combined interphase FISH and Southern blot analysis detected CDKN2 deletions in all 13 ALL cases (100%; 7 homozygous, 6 hemizygous deletions), both cases of AML (100%; homozygous deletions) and in 2 of 5 NHL cases (40%; homozygous deletions). The two deletions in NHL were observed in lymphomas of the diffuse large cell subtype. Thus, 17 of 20 cases (85%) had genomic 9p aberrations which included CDKN2. This higher deletion rate when compared to the cytogenetic analysis (65%; 4 homozygous and 9 hemizygous deletions) reflects the detection of submicroscopic deletions by the combined techniques of interphase FISH and Southern blot analysis.

5.2.2.3 SSCP Analysis

Five of the 6 ALL cases with hemizygous CDKN2 deletions had DNA available for SSCP analysis. HL60, a myeloid cell line with a known point mutation in exon 2 (CDKN2) was used as control. No abnormal SSCP bands were detected in the 5 patient samples, suggesting the absence of point mutations in these samples (Table 4, FIG. 8).

5.2.3 Discussion

In the present study of 20 primary hematological malignancies with cytogenetically detected rearrangements of 9p, CDKN2 was included in genomic alterations in 85% of the cases. This confirms that the CDKN2 region is the likely target of 9p deletions in these hematological malignancies because 10 of 17 cases (59%) of deletions detected by molecular analysis affected an apparently cytogenetically normal band 9p21.

In addition to homozygous deletions, hemizygous deletions were detected in 6 patients or 30% of the samples. Southern blot analysis was not able to detect these hemizygous deletions because of contamination with normal cells. Previous studies had reported relatively small percentages of hemizygous deletions (Hebert et al., 1994; Ogawa et al., 1994; Quesnel et al., 1994).

By SSCP analysis, no alteration of the remaining CDKN2 allele could be detected in any of the five cases with hemizygous deletion examined. Because exons 1 and 2 represent 98% of he coding region of CDKN2, and since SSCP detects 70–90% of point mutations, the data make he possibility of point mutations in the coding region of CDKN2 in these cases very unlikely (Sheffield et al., 1993; Kamb et al., 1994). However, there is a possibility that mutations may be found in the promoter region or other important regulatory regions in the noncoding part of CDKN2. Alternatively, the loss of one allele with 50% reduction in the gene dosage may be sufficient for a growth advantage of the malignant cell. This hypothesis remains to be proven. However, neither scenario explains the predominance of large homozygous deletions in the series. The absence of point mutations of CDKN2 in the cases with hemizygous 9p deletions may suggest that CDKN2 is not the critical target of 9p deletions in these cases. In other primary tumors such as glioblastoma, point mutations of CDKN2 are also rare (Cairns et al., 1994; Giani and Finocchairo, 1994; Jen et al., 1994; Okamoto et al., 1994). The inactivation of either CDKN2B, which was included in all the 9p deletions, or other genes of the region may be important for the malignant phenotype as well. However, it was found that CDKN2B is not deleted in 4 leukemic cell lines with CDKN2 deletion (Dreyling et al., 1994). The smallest commonly deleted region that could be defined in leukemia derived cell lines and primary tumors is bounded on the telomeric side by the 3' end of MTAP and on the centromeric side by CDKN2B. This 120-kb region is included in COSp16; whether additional genes can be identified remains to be determined. Moreover, the frequent codeletion of MTAP, an enzyme involved in the salvage pathway of the purine metabolism could be of interest to clinicians.

5.3 Example 3

Detection of CDKN2 Deletions in Tumor Cell Lines and Primary Glioma by Interphase FISH This example demonstrates interphase FISH analysis on 10 tumor-derived cell lines (4 glioma, 2 melanoma, 2 non-small cell lung cancer, 2 bladder cancer) with rearrangement of the short arm of chromosome 9 detected by molecular or cytogenetic analysis and 9 primary glioblastoma, to determine the accuracy of different probes in detecting 9p deletions in tumor cell lines and primary tumor tissue. The example illustrates the utility of interphase FISH to detect deletions of the CDKN2 region in primary tumors.

5.3.1 Materials and Methods 5.3.1.1 Cell Lines 10 cell lines were used (4 glioma, 2 melanoma, 2 non-small cell lung carcinoma, and 2 bladder cancer) that had been well characterized by conventional cytogenetic analysis. The cell lines were obtained from the American Type Culture Collection or from the investigators who had established them. Cytogenetic deletions of the short arm of chromosome 9 were detected in 4 of 10 cell lines. The cell lines as well as phytohemagglutinin-stimulated normal peripheral blood cells were harvested using standard cell culture techniques. Metaphase chromosomes were prepared as described previously (Le Beau, 1994).

5.3.1.2 Patient Materials

Tumor specimens obtained from 9 patients undergoing biopsy or resection of brain tumors were frozen in liquid nitrogen and stored at −70° C. The tumors were graded as glioblastoma multiforme according to the WHO classification system. Touch preparations were made by touching a freshly cut and thawed tumor surface on a slide. The slides were fixed in methanol:glacial acetic acid (3:1), treated with 5 µg/ml proteinase K (Boehringer Mannheim, Mannheim, Germany), and postfixed in 0.5% paraformaldehyde (Sigma Chemical Co., St. Louis, Mo.).

5.3.1.3 FISH Probes

YAC A88E10 (330 kb), later referred to as YAC 1, and YAC 802B11 (1450 kb), later referred to as YAC 23, were obtained by screening the St. Louis and the CEPH YAC libraries with IFN A1 primers (Henco et al., 1988). YAC 883G5 (1100 kb), later referred to as YAC 17, were obtained from the CEPH Mega YAC library by screening with D9S966 primers (Bohlander et al., 1995). YAC 284D6 (320 kilobases), later referred to as YAC 10/2, from chromosomal band 8q22 was used as a control probe (Erickson et al., 1992). Eight cosmids encompassing a 250-kilobase region around CDKN2 were used. The osmid contig was assembled by screening a flow-sorted human chromosome 9 library Lawrence Livermore Laboratories) with probes from a YAC contig of the region. The exact localization of the FISH probes is shown in FIG. 9. FISH probes were prepared as described previously (Bohlander et al., 1994). YACs were purified on a pulsed-field gel. The DNA of the excised YAC bands as well as the cosmid DNA (20–100 pg) was amplified using a SIA (Bohlander et al., 1992). The amplification products were PCR™ labeled with biotin-11-dUTP (Enzo Diagnostics) and finally treated with DNase (DNase I, 200 pg/mi for 10–20 min: Boehringer Mannheim) to reduce the average fragment size to 150–450 bp. pHuR98, a variant satellite 3 sequence, which hybridizes specifically to the heterochromatic region of chromosome 9 (9qh), was used to determine the copy number of chromosome 9 (Moyzis et al., 1987). The plasmid with a 158-base pair insert was amplified by SIA, PCR™ labeled with Spectrum Orange-11-dUTP (Imagenetics, Framingham, Mass.), and treated with DNase as described. The copy number of chromosome 8 was determined by a centromeric FISH probe CEP 8 Spectrum Orange (Imagenetics).

5.3.1.4 FISH Procedure

Two color FISH with YAC or cosmid probes and a centromeric probe was performed as described previously (Rowley et al., 1990). The hybridization solution contained approximately 0.1 µg of each probe, 1 µg of human Cot1-

DNA (BRL), 0.6 μg of human placental DNA, and 3 pg of salmon sperm DNA/slide in a 10-μl volume. The biotinylated probes were detected with FITC-conjugated avidin. The slides were counterstained with 4', 6'-diamidino-2-phynylindole dihydrochloride and were analyzed using epifluorescence and a single-pass filter (Chroma Technology) to avoid superimposition of the centromeric and the. YAC signals. For interphase analysis of the cell lines, the FISH signals of a total of 500 single, intact cells were counted by 2 independent observers. In addition, 25 metaphase cells of each cell line were analyzed. In the tumor samples 100 single intact cells were analyzed. For FIG. 9, separate gray scale images of 4N,6N-diamidino-2-phenylindole-stained cells and fluorescence signals were captured using a cooled charge-coupled device camera (Photometrics, Tucson, Ariz.) and were pseudocolored and merged using NIH Image or Adobe Photoshop.

5.3.1.5 Molecular Analysis

Cell line DNA was extracted and treated with restriction enzyme (HindIII), electrophoresed on a 1% agarose gel, and transferred to a nylon-based nitrocellulose membrane (Gene Screen Plus; NEN, Boston). DNA filters were hybridized with $^{32}$P-labeled probes from 9p21 and exposed to X-ray film. The probes used were REY24, CDKN2 cDNA, D9S966, and D9S171 (Bohlander et al., 1995). The exact order of the molecular markers is shown in FIG. 9.

hybridization signals for YAC 11 was significantly reduced in 3 cell lines (H290, H4, A172). Previous detailed molecular analysis revealed that the distal deletion breakpoints of these cell lines lie within the YAC 11 region (Olopade et al., 1992; 1993). Therefore the intensity of the signal is reduced. However, it was still possible to detect signals for YAC 11 in one cell line [H4] even though 90% of the YAC region was deleted. YAC 17 was homozygously deleted in 2 cell lines (H290, RT4), the number of copies was reduced in 2 other cell lines (A172, H4), and 1 cell line showed a partial deletion of one allele (U410). The cosmid probe which covers the region of the CDKN2 was homozygously deleted in 8 of 10 cell lines. In one cell line (T98) the signal was significantly; reduced indicating a partial deletion of the region. Southern blot analysis showed a homozygous deletion of CDKN2 on this cell line, whereas another molecular marker of the region was retained. In 5 cell lines (H4, U410, HS294T, RT4, UM-UC3), both control probes, the chromosome 8 centromere probe and the YAC 10/2 probe, showed a similar distribution of signals/cell indicating the comparable hybridization efficiency of centromeric and YAC probes. However, in the 5 remaining cell lines (all with 4 or more copies of chromosome 8) the number of chromosome 8 centromere signals/cell differed from the number of YAC 10/2 signals/cell suggesting the presence of rearrangements affecting chromosome 8.

TABLE 5

Interphase Analysis of Normal Peripheral Blood

| FISH probe | Region/ marker | No. of hybridization signals/cell (%) | | | | | |
|---|---|---|---|---|---|---|---|
| | | 0 | 1 | 2 | 3 | 4 | >4 |
| pHuR | 9qh | 0.02 ± 0.06[a] | 3.22 ± 0.54 | 95.70 ± 0.50 | 0.78 ± 0.37 | 0.32 ± 0.32 | 0 |
| YAC 17 | D9S966 | 0.30 ± 0.27 | 3.90 ± 1.33 | 94.66 ± 1.63 | 0.74 ± 0.39 | 0.40 ± 0.27 | 0 |
| COS p16 | CDKN2 | 0.10 ± 0.19 | 2.68 ± 1.00 | 96.02 ± 1.46 | 0.82 ± 0.62 | 0.32 ± 0.23 | 0.04 ± 0.13 |
| YAC 11 | IFN A | 0.06 ± 0.10 | 2.12 ± 0.8 | 96.60 ± 1.10 | 0.80 ± 0.49 | 0.42 ± 0.32 | 0 |
| YAC 23 | IFN A | 0.04 ± 0.08 | 1.92 ± 0.33 | 97.08 ± 0.65 | 0.78 ± 0.69 | 0.12 ± 0.10 | 0 |
| YAC 10/2 | 8q22 | 0.16 ± 0.18 | 1.94 ± 0.65 | 97.04 ± 0.65 | 0.62 ± 0.30 | 0.24 ± 0.16 | 0 |

[a]Mean ± SD of hybridization signals/cell.
Dual color FISH was performed with normal peripheral blood cells of 10 probands.

5.3.2 Results 5.3.2.1 Interphase Analysis in Normal Peripheral Blood

To determine the reliability of the FISH probes in nonmalignant cells, ten test hybridizations of peripheral blood cells from normal individuals were performed with each probe (Table 5). Both centromeric and YAC probes showed an almost identical distribution of signals/cell comparable to previously published results for centromeric probes. In 500 nuclei scored, 2 signals were detected in 94–97% of the cells.

5.3.2.2 Interphase Analysis in Tumor Cell Lines 9p deletions were determined by molecular analysis in 9 of 10 cell lines (Table 6). All deletions were detected as well by Interphase FISH with the COSp16 probe. The results of the FISH analysis are summarized as a deletion map (FIG. 9). YAC 23 was homozygously deleted in one cell line (H322). YAC 11 which covers the proximal IFN gene cluster was absent in 2 cell lines (U410, H322); only one copy was retained in one cell line (H4). Moreover, the intensity of the Subpopulations of cells showed an aberrant number of centromere 8 and 9 signals reflecting the heterogeneity of the cell lines. Metaphase analysis confirmed these subpopulations of cells with a loss or gain of a chromosome homologue in 5 of 10 cell lines. However, the heterogeneity of the cell lines did not affect the analysis of 9p deletions, because all subpopulations of a cell line uniformly had either deleted or retained the tumor suppressor region on 9p. In the latter group the number of signals/cell was highly comparable to the centromere 9 data. In contrast, in the cell lines with homozygous deletions 99.5±0.4% (SD) of the cells showed no hybridization signal (FIG. 10A). Nonhomozygous deletions could be detected with a similar accuracy. Thus, there was good concordance between the molecular results and the FISH data. All the homozygous deletions determined by molecular analysis were detected by Interphase FISH (Table 6). In addition, cell lines with a partial loss of the IFN gene cluster had a reduced intensity of the hybridization signal of YAC 11.

TABLE 6

Molecular and Cytogenetic Features of Human Tumor Cell Lines

| Cell line | Tumor type | Cytogenetic alterations of chromosome 9 | Ploidy | No. Chrom 9 (FISH) | IFNA | REY24 | CDKN2 | D9S996 | D9S171 |
|---|---|---|---|---|---|---|---|---|---|
| A172 | Glioma | 9p on marker, 16 marker chromosomes | Near triploid | 4 | $-p^a$ | − | − | − | + |
| H4 | Glioma | del(9p) 3X | Hypertriploid | 3 | $-p^a$ | − | − | − | + |
| T98 | Glioma | 14–16 marker chromosomes | Hyperpentaploid | >4 | + | + | − | + | + |
| U410 | Glioma | ND | Near diploid | 2 | − | − | − | − | + |
| HS294T | Melanoma | Normal | Near triploid | 3 | + | − | − | + | + |
| RPMI7951 | Melanoma | ND | Heteroploid (>2X66X) | >4 | + | + | + | + | + |
| H290 | NSCLC | del(9)t(6;9)(p11;p11), del(9)(p11), del(9)(p22) | Near tetraploid | 4 | $-p^a$ | − | − | − | − |
| H322 | NSCLC | del(9)(p13),25 marker chromosomes | Near tetraploid | 4 | − | − | − | − | + |
| RT4 | Bladder carcinoma | −9, del(9)(p21p22) 3X | Hypotetraploid | 3 | $-p^a$ | − | − | − | + |
| UM-UC3 | Bladder carcinoma | +9, del(9)(q12 or q34), add(9)(q12) | Hypertriploid | 4 | + | − | − | − | + |

$^a$+, autoradiographic signal comparable to the control; −, no signal; p, partial deletion of the IFNA gene cluster (only some of the multiple bands are present); ND, not done; NSCLC, non-small cell lung carcinoma.
The number of chromosome 9 copies were determined by FISH analysis of the centromere 9 probe (pHuR 98). The presence of the interferon A cluster (IFN A) and of the molecular markers REY24, CDKN2, D9S966, and D9S171 were determined by Southern blots.

5.3.2.3 Interphase Analysis in Tumor Specimens

To determine 9p deletions in primary tumors, 9 brain tumors, pathologically classified as glioblastoma multiforme, were analyzed using the FISH probes YAC 11, COSp16, and YAC 10/2 for detection of the deletion of the proximal IFN gene cluster (YAC 11), the CDKN2 region (COSp16), and a control probe (YAC 10/2). Of 9 tumors, 4 tumors (44%) had a deletion of the proximal IFN gene cluster [YAC 11 (FIG. 10B)]. No cosmid signal for CDKN2 was detectable in 5 tumors. In tumor sample 1 (FIG. 10B), the intensity of the hybridization signals of the cosmid contig was significantly reduced in comparison to the control YACs, indicating a partial deletion of the cosmid contig.

In tumor sample 7 (FIG. 10B), 7% of the cells did not show any YAC 11 signal. This tumor had only one copy of chromosome 9. Therefore, the number of cells without hybridization efficiency. In aneuploid tumors (6 cases, determined by interphase FISH) a subpopulation of cells (13.4±4.8%) had 2 copies of chromosome 9. This cell population was not identified in cell lines and probably represents the contamination with normal cells (stromal cells, lymphocytes, etc.).

5.3.3 Discussion

Interphase FISH analysis is a well established method to determine chromosomal aberrations in hematological malignancies and solid tumors. Using the appropriate probes, interphase analysis is able to detect chromosomal aberrations in clinical tumor specimens contaminated with normal cells and is also able to detect these changes in small subpopulations of cells. In this study, the analysis of 10 cell lines derived from gliomas, melanomas, non-small lung cancer, and bladder cancer and 9 primary gliomas is described using interphase FISH analysis. For these studies, FISH probes were generated from YACs and a cosmid contig by a SIA technique described previously (Bohlander et al., 1994). This procedure yields consistent and strong FISH signals for interphase analysis. In contrast, single cosmids of the 9p region had a hybridization signal of only moderate intensity due to the small insert size. At present, FISH probes of YACs or similar vectors have been generated previously by Alu-PCR™ (Nelson et al., 1989). This amplification technique is limited by the number of Alu sequences per clone which varies considerably. Hybridization of YAC probes generated by Alu-PCR™ to extended chromatin preparations showed incomplete representation of the YAC insert (Tocharoentanaphol et al., 1994). Therefore, Alu-PCR™ generated probes may not accurately detect partial deletions of the hybridization region.

In these studies, the cosmid contig probe identified all homozygous deletions of the CDKN2 region in 9 of 10 cell lines. Only 3 of these cell lines had cytogenetically visible deletions of the short arm of chromosome 9. The deletions were confirmed by molecular analysis of the cell lines. The remaining melanoma cell lines (RPM17951) had a rather complex cytogenetic rearrangement of the short arm of chromosome 9 but did not show any deletion of the CDKN2 region. Sequencing data of this cell line did not detect any mutation within the second exon of CDKN2. The majority of previously described point mutations of CDKN2 were located in this region (Cairns et al., 1994; Giani and Finocchiaro, 1994; Jen et al., 1994).

The proximal IFN gene cluster was deleted in 4 of the 9 primary tumors. Although the small number of tumors does not allow an estimation of the overall frequency of 9p deletions in glioblastoma, these results are consistent with previous studies (Olopade et al., 1992). Another study detected IFN gene deletions in 50% of the high grade glioma (James et al., 1991). The authors proposed a tumor suppressor activity of the proximal IFN gene cluster in glioblastoma (James et al., 1993). However, the data exclude the IFN genes from the critical region of deletion inasmuch as they were deleted in only 4 of 6 tumors with 9p deletions. The CDKN2 region was deleted in 6 of 9 tumors (67%). Other studies showed CDKN2 deletions in 17–69% of the tumors (He et al., 1994; Jen et al., 1994; Schmidt et al., 1994). In a series of primary gliomas, Southern blot analysis showed homozygous deletions of CDKN2 in 45% of the tumors. However, Southern blot analysis may miss some of the 9p deletions because of contamination with normal cells. In addition, it is well known that some tumors are heterogeneous, and 9p deletions may be present in only a subpopulation of cells. These data suggest that the 250-kb region covered by the cosmid contig includes the target gene of the 9p deletions in primary glioma. CDKN2 is located in the smallest region of deletion on 9p. However, the frequency of point mutations detected in primary tumors is rather low (Giani and Finocchiaro, 1994; Jen et al., 1994). Therefore, the simultaneous deletion of the neighboring genes may be responsible for the selective growth advantage for the malignant cells. Hannon and Beach (1994) proposed that p15 (ATS2, CDKN2$^b$), a transforming growth factor β-regulated member of the p16 family, also plays an important role in carcinogenesis. p15 maps approximately 20 kilobases centromeric to CDKN2 and is included in the cosmid contig (Kamb et al., 1994). It may well be that the predominant mechanism of 9p rearrangements in primary tumors is the deletion of a large genomic region which would inactivate both genes in one step. In fact, in cell lines as well as in primary glioblastoma, the vast majority of deletions include both genes (Jen et al., 1994; Kamb et al., 1994; Nobori et al., 1994). Therefore, it appears that homozygous deletions are the predominant mechanism for inactivating this region. Because further mapping data are crucial to determine the clinical significance of these rather large deletions in primary tumors, FISH will play an important role in characterizing the deletion.

Recently, the over-expression of CDK4, the target molecule of p16, was proposed as an additional mechanism of functional p16 inactivation (He et al., 1994; Schmidt et al, 1994). Both events would result in a dis-inhibition of the cell cycle. However, in a number of cell lines and primary gliomas the homozygous deletion of CDKN2 was the much more frequent event (He et al., 1994; Schmidt et al., 1994).

5.4 Example 4

Identification of Tumor Suppressor Genes Involved in Leukemia

A tumor suppressor gene (TSG) involved in acute lymphoblastic leukemia, gliomas and lung cancers is present on 9p, and is likely to be involved in the more general pathway of oncogenesis since CDKN2 (p16$^{INK4}$) is a candidate TSG at this locus. The CDKN2 gene is an attractive candidate for a tumor suppressor gene because loss of its normal function as an inhibitor of CDK4 could lead to uncontrolled cell growth. Inactivation of CDKN2 by homozygous deletion or point mutation has been reported in a large proportion of cultured cell lines from multiple tumor types. It is mutated to a lesser degree in primary tumors. In addition, germline point mutations has recently been described in familial melanoma. Definitive proof that CDKN2 is the 9p tumor suppressor gene depends on its ability to suppress tumorigenicity when introduced into cell lines with deletions. However, there is mounting evidence that CDKN2 may not be the only biologically relevant gene in this locus.

This example relates to methods of reintroducing identified candidate genes into mouse and human cell lines with deletions by minigene or YAC transfection, methods of identifying transcription units in the critical region and testing for alterations of such transcripts in glioma cell lines and primary tumors, methods for obtaining full-length clones of relevant transcripts from cDNA libraries and characterizing the DNA sequence, structural features, and predicted protein characteristics, methods for examining additional breakpoint junctions in glioma cell lines to search for possible clues as to the mechanism of the deletions, methods for determining the clinical significance of 9p loss in gliomas.

5.4.1 Deletion Mapping

Initial observation of deletions or rearrangements of IFNA and IFNBI genes in solid tumors have been extended to other cell types, specifically in glioma derived cell lines, primary glioma samples, and lung cancer cell lines. A number of the cell lines also lack MTAP enzyme activity (Borrensen et al., 1990). In a few cases, the deletions that include both the IFN gene cluster and the MTAP gene are submicroscopic and interstitial in nature which suggests that these genes or a gene very closely linked to them are the relevant genes. It was possible to determine the order of the genes on 9p: telomere-IFNBI-IFNA/IFNW-MTAP-D9S126-D9S3-centromere. An SRO was defined for the deletions to be between the IFN gene cluster and MTAP. In addition, a long range map of the IFN gene cluster was constructed which identified the 26 IFN genes and pseudogenes on this map. Scaffold attachment regions (SARs) were also localized in relation to the IFN genes on this map. Several cell lines have been identified with telomeric deletion breakpoints within the IFN gene cluster. Several of these breakpoints were mapped precisely on this genetic map which permitted the cloning of the breakpoint junction in two glioma cell lines A172 and A1235. The deletion in the glioma cell line A1235 is part of a complex rearrangement that also involves an inversion while the deletion in the glioma cell line A172 seems to be a simple interstitial deletion. The breakpoint analyzed in A1235 represented the distal junction of this inversion-deletion. That an involvement of "AT" rich sequences including SARs and LINE elements was found in the deletion breakpoints in both cell lines was noteworthy.

5.4.2 Construction of a Long-Range Physical Map

Using the CEPH Mega YAC library, screening was performed with two STSs: One for the INFA1 gene and the other for the microdissection marker MDS59 (D9S966). The IFNA1 STS flanked the previously defined SRO of deletions for the 9p TSG on the telomeric side and the MDS59 STSs flanked the SRO on the centromeric side. Several YACs were found for each of the two STSs. However, none of these YACs contained both STSs. FISH probes were prepared for each of the positive YACs (about 15 YACs) so that they could be tested for chimerism. Interphase FISH studies suggested that the two groups of YACs were very close if not overlapping. Some of the non-chimeric YACs from each group were chosen to use for a YAC end rescue protocol. The ends of several YACs were successfully cloned and a physical map of 2.8 Mb was constructed (see Example 1).

After establishing that the Mega YAC groups from the IFN gene cluster and the microdissection clone MDS59 (D9S966) overlapped, the YAC contig was converted into a cosmid contig. Hybridization probes were prepared from selected YACs and screened a gridded flow sorted chromosome 9 cosmid library (Lawrence Livermore Lab; gridded at Oncor) directly with these probes. Identified were several hundred cosmid clones that were detected by the YAC probes. After using an IFN consensus probe and one of the MDS59 YACs for a negative selection screen, 128 cosmids were identified that were mainly located between the IFN type I gene cluster and MDS59 thus covering the region of the TSG. These 128 cosmids were transferred to microtiter well plates and replica filters were prepared with all of the 128 in a 12×11 array. These filters were probed with all of the overlapping YACs from the region. More detailed ordering of the cosmids was performed for the region of the TSG.

This was accomplished by using groups of cosmids that were positive for a YAC end probe as hybridization probes to put back on the cosmid array. In this way cosmids that overlapped with the cosmids from the group could be detected. This approach was very successful and allowed the construction of a cosmid contig of the TSG region.

The cosmids from this ordered contig were then used for several different strategies to detect expressed sequences: direct screening of cDNA libraries, exon trapping, and a cDNA selection protocol based on the capture of sequence independently amplified cosmid fragments by biotinylated cDNA.

5.4.3 Characterization of Microcell Hybrids

A system has been described which forces stable, non-random retention of human chromosome 9 in somatic cell hybrids and microcell hybrids grown in the medium (Broeker et al., 1993). MTA accumulates in all proliferating cells and, after its breakdown by MTAP, is recycled to the purine salvage pathway, and to the synthesis of methionine (one of the precursors of the polyamine biosynthetic pathway). The breakdown of MTA provides the main source of purines for the salvage pathway (Hall et al., 1990). Therefore cells that lack MTAP die in the presence of inhibitors of de novo purine synthesis (Borrensen et al., 1990). However, cells deficient in MTAP can be rescued from purine starvation by the introduction of a normal human chromosome 9 after cell hybridization or microcell fusion. This allows the design of a cell culture system that selects for the retention of a normal human chromosome 9 in somatic cell hybrids.

It has been shown that Mouse L cells and a number of human tumor cells lack MTAP activity and can be killed by adding azaserine (an inhibitor of de novo purine synthesis) to the growth medium (Deville et al., 1991). MTAP competent cells will stop proliferating in the presence of azaserine but can be rescued by the addition of MTA to the growth medium. To investigate the hypothesis that a tumor suppressor gene is deleted in Hs294T (a melanoma cell line that has no deletion of the IFN genes but lacks MTAP activity), a normal copy of human chromosome 9 was introduced into the cells by microcell mediated chromosome transfer (Tompson et al., 1992). In a complimentary study two different copies of chromosome 9, which contained small deletions on the short arm (9p21-p22) that do not include AITAP were also introduced into Hs294T cells.

Several colonies of microcell hybrids that contained a normal chromosome 9 formed within 4 weeks and attained colony sizes with the equivalent of 5–6 population doublings. The (+9) hybrids remained viable on the plates for an indefinite period of time after cessation of proliferation. The phenotype of these hybrids is characteristic of the senescence of diploid human fibroblast. In contrast, the microcell hybrids that contained a chromosome 9 with a small deletion at 9p21-p22 continued to grow for many population doublings and did not senesce. Similar studies were performed with U87MG, a glioma cell line with a large deletion including the IFN genes. The (+9) hybrids continued proliferating for several months in 10% horse serum and did not senesce. However, when expanded the U87 (+9) hybrids did not produce tumors when injected into nude mice. These results suggest that a gene present on 9p21-p22 functions in a pathway that leads to senescence in the melanoma cell line and suppresses tumorigenicity in the glioma cell line. Thus, deletion of DNA sequences in this region would inactivate the locus for senescence, leading to immortalization of the cell.

This provides the cell with a growth advantage that may contribute to neoplastic transformation in vivo and in vitro.

Genomic fragments have been obtained from within this SRO which detects the overlapping homozygous deletions in Hs294T, U87MG and the T98G donor chromosome. This region contains CDKN2. It is possible that the reintroduction of CDKN2 on the normal chromosome 9p into the Hs294T and U87MG is responsible for both the cell cycle arrest, and the loss of tumorigenicity. Concordant with this hypothesis, the CDKN2 gene is present in the donor hybrids containing a normal chromosome 9p but is absent from the T98G donor cell line and from the recipient cell lines. It remains to be proved if these effects are mediated by the CDKN2 gene or a closely linked gene or genes.

TABLE 7

Tumorigenicity of Microcell Hybrids Containing a Normal or Deleted Human Chromosome 9

| Cell Lines | Type of donor chromosome 9 | # of cells/ injection | # tumors/ # sites | % Tumors |
|---|---|---|---|---|
| K562 (leuk) | none | $5 \times 10^6$ | 9/9 | 100 |
| KTm3 | T98G | $5 \times 10^6$ | 8/8 | 100 |
| KFm1 | ALL patient | $5 \times 10^6$ | 6/6 | 100 |
| CEM (leuk) | none | $10 \times 10^6$ | 10/10 | 100 |
| CJm3 | fibroblast | $10 \times 10^6$ | 0/8 | 0 |
| CJm4 | fibroblast | $10 \times 10^6$ | 0/8 | 0 |
| U87MG (gli) | none | $2.5 \times 10^6$ | 10/10 | 100 |
| UNm20a | fibroblast | $2.5 \times 10^6$ | 0/8 | 0 |
| UTm10b | T98G | $2.5 \times 10^6$ | 8/8 | 100 |
| UFm4c | ALL patient | $2.5 \times 10^6$ | 4/4 | 100 |
| UFm5a | ALL patient | $2.5 \times 10^6$ | 8/8 | 100 |
| Hs294T(mel) | none | $2.5 \times 10^6$ | 10/10 | 100 |

Defining the commonly deleted region in the cell lines used has permitted obtaining expressed sequences from within this region because proof that a TSG9 is indeed present on 9p depends upon introducing the gene into deficient cell lines. Because one could not exclude the possible involvement of the IFN genes in tumor suppression, U87MG glioma cell line has been transfected with IFNA gene. Results suggest that constitutive expression of the IFNA gene in this cell line did not prevent tumor formation in nude mice, though the cells had a slower proliferation rate.

TABLE 8

Tumorigenicity of Human Tumor Cell Lines and Derived Transduced Cells Containing the Human IFNA1 Gene

| Cell Line | # tumors/# sites | % tumorigenicity |
|---|---|---|
| K562 (leukemia) | 7/8 | 87.5 |
| K562pA317a$_{9-4}$ | 0/8 | 0 |
| K562pA317a$_{9-6}$ | 0/8 | 0 |
| U87MG (glioma) | 10/10 | 100 |
| U87MGpBK89D | 8/8 | 100 |
| U87MGpBK89pool | 8/8 | 100 |
| U87MGpSV2Neo | 4/4 | 100 |

5.4.4 Identifying expressed sequences in the SRO

The region involved in gliomas has been narrowed to only a few hundred kilobases (about 400 kb) and a cosmid contig has been assembled. Therefore, any gene found in this region is likely to be a candidate TSG9. Two un-methylated CpG islands have been identified in this region which are known to be frequently located close to the 5' end of housekeeping genes. Unique DNA sequences have been isolated from within the cosmids and analyzed them for interspecies conservation, by hybridization to zoo-blots.

By adaptation of a technique that selects coding regions from large genomic segments such as YACs and cosmids (Call et al., 1990), cDNA inserts have been amplified by the polymerase chain reaction (PCR™) containing a biotinylated nucleotide at the 5' end. The cDNA is attached to strepavidin magnetic beads which bind the biotin molecule with a disassociation constant of 10–15. The genomic YAC or cosmid DNA is prepared by undergoing sequence-independent amplification (SIA) to attach specific primers to the DNA. The SIA fragments are hybridized to the cDNA, washed, then bound fragments are eluted and amplified by PCR™. After amplification, the mixture is enriched for those sequences which are homologous to coding regions from the cDNA.

One group of cosmids that were used for the selection are located at the telomeric end of YAC 942A3, spanning approximately 80 kb. Two of the selected fragments were used to identify homologous cDNA clones in a brain cDNA library. Both the selected fragments and the corresponding cDNAs were analyzed by Southern blot. One cDNA (Le19-1) was represented once in 30,000 clones, while the second cDNA (LE19-2) was represented only once in 600,000 clones, both in an adult brain cDNA library. Both clones were mapped by FISH and/or Southern blot to the region on 9p22. Sequence information yielded no significant homology of either cDNA to any other gene in Genbank. Both cDNAs are located 40–60 kb from CDKN2, and either one or both are included in almost every deletion where CDKN2 was deleted in cell lines. This indicated that there are other candidate tumor suppressor genes in the region based on the deletion mapping.

A second group of cosmids used in the selection are located between the centromeric end of Yac 886F9 and the telomeric end of Yac 19 (942A3), which encompasses approximately 150 kb. Twenty-five selected fragments, most of which are unique representatives in the selection, have been analyzed. One of the fragments has been used to isolate cDNAs from a foreskin fibroblast cDNA library. The selected fragment has been sequenced, and shows significant homology to an anonymous, expressed sequence in fetal brain, and to a gene located in the MXI region of chromosome 21. The fragment maps within the 150-kb region between Yac 886F9 and Yac 942A3.

5.4.5 Experimental Methods

The introduction of TSG9 into glioma cells after YAC transfection or gene transfection may be documented by FISH analysis, as well as RFLP analysis for additional DNA, using polymorphic probes from 9p22. Several features of the malignant phenotype are assessed in the transfectants. The morphology of parental cells and the "TSG9" transfectants and transfectant with "irrelevant YAC" or vector alone is examined in great detail to determine if there are any differences in their morphology. In vitro growth properties such as serum independence, contact inhibition, saturation density, population doubling time, as well as ability to form colonies in soft agar may be studied. Breast cancer cell lines and the YAC transfectants may be examined for growth in athymic nude mice by injecting cells ($5 \times 10^6 \times 10^7$) subcutaneously into these mice. For U87MG transfectants, the mice must be supplemented with estrogen since the cells are estrogen dependent. Tumors may be initially suppressed in the mice injected with "TSG9" transfectants, but may later grow due to loss of the transferred YAC. These revertants may be examined by resecting the tumors that form, placing the cells back in culture and exposing them to the selective medium. If the introduced YAC had been lost, the cultures will revert to sensitivity.

To clone additional genes, each of the exons trapped and each unique DNA fragment is examined. Initial screening is done by hybridizing the fragment to a panel of deletion cell lines and a multiple tissue Northern blot. Exons that are non-repetitive and deleted in the cell lines are sequenced in order to generate STSs that can be useful for further screening. Where transcripts are identified, a cDNA library from the tissue with a high level of expression is screened. Because of the ubiquitous expression of such genes, adult and fetal brain as well as fibroblast oligo-dT primed and random primed cDNA libraries have been utilized.

Additional cDNA libraries may be prepared using the RNase H method of Gubler and Hoffman with priming with oligo d(T) or random oligonucleotide hexamers. cDNA libraries are prepared from mRNA which has been completely denatured by methylmercuric hydroxide to release secondary structures. After second strand synthesis, low molecular weight (less than 400 bp) cDNAs are removed and the remaining cDNAs are selected and cloned into lambda phage vectors. Resulting recombinant molecules are packaged using commercially available extracts (Stratagene) and the resulting particles plated using E. coli of an appropriate strain. The pre-made libraries come with full protocol handbook and appropriate methods will be used for bacterial culture plating, library plating and tittering and making filter replicas.

5.5 Example 5

Inactivation of CDKN2 (p16$^{INK4A}$) Tumor Suppressor Gene Contributes to Tumor Progression in Low-Grade Lymphoid Malignancies The natural history of low-grade non-Hodgkin's lymphoma (NHL) is characterized by a prolonged indolent phase which is followed by progression to intermediate- or high grade lymphoma with a dismal prognosis. This clinical progression is often associated with detectable histologic changes but the genetic alterations involved in the transformation have not been well characterized. The tumor suppressor locus on the short arm of chromosome 9, CDKN2, encodes a 16 kDa protein (p16$^{INK4A}$) which acts as a negative regulator of the cell cycle through its interactions with RB and CDK4/CDK6 proteins. To determine whether CDKN2 is involved in the transformation to diffuse large cell lymphoma (DLCL), 11 cases of de novo DLCL; 5 cases of DLCL which evolved from low grade NHL (transformed DLCL); and 9 low grade NHL which had subpopulations of large cells with diffuse growth pattern (7 follicular NHL, 1 CLL, 1 mycosis fungoides) were examined. Interphase FISH was performed on these samples using a 250-kb cosmid contig (COSp16) encompassing CDKN2. One of 11 cases of de novo DLCL (9%) and 1 of 9 low grade NHL (11%) had homozygous deletions of COSp16. In contrast, all five transformed DLCL (100%) has COSp16 deletions. Two cases had homozygous COSp16 deletions, two cases had hemizygous deletions, and one case had a partial homozygous deletion of the cosmid contig. Thus, CDKN2 is frequently deleted in transformed DLCL in contrast to de novo DLCL ($p<0.01$, Fisher's exact test) or low grade NHL ($p<0.03$). In addition to its critical role in ALL, these results suggest that CDKN2 deletion is a genetic marker for the histologic transformation from low grade to diffuse large cell lymphoma.

5.6 Example 6
Genomic Cloning and Characterization of the MTAP Gene

This example describes the nucleotide sequence, expression and genomic organization of the human MTAP gene.

5.6.1 Materials and Methods

5.6.1.1 Screening of cDNA and Genomic Libraries

To obtain YAC end-specific probes, YAC end-rescue reactions were carried out as described by Hermanson et al., 1991. A YAC end rescued inserts from YAC 24 was used as probe to screen the Lawrence Livermore chromosome 9 specific cosmid library. In addition, a cosmid contig of the critical region on 9p21 was assembled as described. These cosmids were used in exon-trapping studies using the Exon Trapping System (Gibco, BRL). Exon 18-11 trapped from cosmid 18 was used to screen a λgt11 human foreskin fibroblast 5' stretch cDNA library from Clontech. A 2.5-kb cDNA was obtained and subcloned into pBluescript SK+ (Stratagene) producing the two clones, pM1.1 and pM1.4. The cosmid contig subarray was rescreened with probes M1.1 and M1.4 to identify cosmid clones corresponding to the entire MTAP cDNA.

5.6.1.2 Determination of Exon/Intron Boundaries

The genomic organization was determined by restriction enzyme digestion and southern blot analysis. Mini-DNA preparations from individual bacterial colonies containing recombinant cosmids were performed using standard procedures. The cosmids shown in FIG. 11 were used for mapping and sequencing reactions. A Southern blot from each cosmid clone digested with HindIII was hybridized with probes containing various parts of the cDNA as shown in FIG. 12. The probes were generated by PCR™ amplification of the MTAP cDNA clone using primers designed from the region. The Southern blots were washed with at high stringency in 0.1×SSC and 1% SDS at 65° C. for 45 min. Exon-intron boundaries were sequenced directly from cosmid DNA using either the Sanger dideoxy chain termination method using a Sequenase™ kit (United States Biochemical) or by cycle sequencing using the ABI PRISM Cycle Sequencing Kit on a 9600 Perkin Elmer thermocycler using appropriate oligonucleotides as primers.

The genomic sequences were compared to the cDNA sequence to establish the exon-intron boundaries. Sequence analysis was performed using MacVector 4.15KSB1, Pustal Sequence Analysis software (IBI), and the GenBank database using the BLASTN and BLASTP programs. These nucleotide sequences have been submitted to GenBank.

5.6.1.3 Long Range PCR®

Long range PCR™ was performed to determine the length of introns using Elongase as previously described. PCR™ reactions were carried out in a volume of 50 μl containing 100 ng of genomic cosmid or placental DNA, 1X Elongase buffer (60 mM Tris-$SO_4$, pH 9.1) at 25° C., 18 mM $(NH_4)_2SO_4$ and 1.7 mM $MgSO_4$; 200 mM of dNTP; 200 zm each of forward and reverse primers, and 1 U of Elongase. A 30 sec, 94° C. elongation step was performed followed by 30 cycles of denaturation (94° C. for 30 sec), annealing (58° C. for 30 sec) and extension (68° C. for 5 min).

5.6.1.4 Localization of MTAP Transcription Start Site

The technique of 5'-RACE amplification by PCR™ was performed to determine the MTAP mRNA transcription start site. A human placental 5'-RACE-ready cDNA kit from Clontech was used. The resulting PCR™ products were gel purified and submitted to double-stranded DNA sequencing as described above.

Because human multiple tissue northerns (Clontech) probed with pM1.1 and pM1.4 showed two major transcripts in all tissue types, 3'-RACE was also performed to determine if a longer cDNA or an alternate polyadenylation signal could be obtained.

5.6.2 Results

5.6.2.1 Homology Analysis of the HMTAP Gene

The MTAP gene has been highly conserved through evolution as shown after hybridization of the cDNA to an evolutionary blot shown in FIG. 13 at low stringency. The nucleotide sequence of the 2.5-kb cDNA revealed a continuous open reading frame of 345 amino acids extending from nucleotide number 10 including the initiator methionine codon. The DNA sequence revealed no homology and protein sequence comparison with the highest scoring protein sequences showed only a 47% (54 of 114 amino acids) homology to a hypothetical 25.8-kDa protein in the petC region of *Rhodospirillum rubrum*. The homology detected with other purine nucleoside phosphorylase (PNP) was lower but extended over a slightly larger region in eukaryotic proteins, human, mouse and *S. cerevisiae* PNPs. It is known that MTAP is the counterpart of PNP but both work on different substrates.

5.6.2.2 Exon/Intron Structure

After screening the cosmid array with MTAP cDNA, 5 cosmids (cosmids 18, 28, 29, 31, and 81) were identified using the MTAP cDNA probe. A HinduII restriction enzyme map was constructed for the MTAP genomic region using multiple approaches. The MacVector program was used to perform a HindIII restriction enzyme analysis of the pM1.1 and pM1.4 cDNA sequences. The sizes of the introns were determined after performing long range PCR™ on cloned genomic cosmid DNA.

Intronic sequences were obtained by direct sequencing from the cosmids using reverse and forward primers from the 5' and 3' ends from different parts of the cDNA. This permitted the definition of many exon-intron boundaries. MTAP was found to be composed of 7 exons within 22 kb of DNA (FIG. 11). All the HindIII sites identified are shown in FIG. 13.

A HindIII was found within exon 5 at base pair 658 and within exon 6 at base pair 856 of the pM1.1 cDNA clone. A third HindIII site was found eight base pairs 5' of the poly(A) tail in pM1.4. Using sequencing primers CF and EF (Table 10) on cosmid 31 DNA enabled the location of HindIII sites thirteen base pairs into intron 3 and three hundred and ten base pairs into intron 4.

Southern blot hybridization of HindIII-digested placenta and genomic cosmid DNA using probes generated from the pM1.1 and pM1.4 cDNA clones revealed multiple bands as shown in (map 1 and 2). The sizes of each fragment and the probes used are seen in FIG. 12 and Table 9.

TABLE 9

Methylthioadenosine phosphorylase
Exon-Intron Organization

| Exon No. | Exon Size (bp) | Sequence at Exon-Intron Junction | | Intron Size (bp) | Preceding or Interrupted Amino Acid |
|---|---|---|---|---|---|
| | | 5' Splice Donor | 3' Splice Acceptor | | |
| 1 | 145 | GCCGTGAAGgtgaga (SEQ ID NO: 3) | tcttagATTGGAATA (SEQ ID NO: 4) | ~3600 | Lys |
| 2 | 87 | TTTGGCAAGgttaat (SEQ ID NO: 5) | atgcagCCATCTGAT (SEQ ID NO: 6) | ~1100 | Lys |
| 3 | 59 | CTTGCAAGgtatgg (SEQ ID NO: 7) | ccatagGCATGGA (SEQ ID NO: 8) | ~1200 | Arg |
| 4 | 271 | ACGAGAGAGgtgtgt (SEQ ID NO: 9) | ttctagGTTCTTATA (SEQ ID NO: 10) | ~4000 | Glu |
| 5 | 240 | GAGGAAGCAgtaagt (SEQ ID NO: 11) | actctagGTTTCGGTG (SEQ ID NO: 12) | ~4000 | Ala |
| 6 | 123 | AACCTGAAGgtaagt (SEQ ID NO: 13) | atccagAATATGGCC (SEQ ID NO: 14) | ~2400 | Lys |
| 7 | 1269 | TTGCTTTTTtaactc | (SEQ ID NO: 15) | (cleavage site for polyadenylation) | |

113 bp = 5' untranslated region
1230 bp = 3' untranslated region

TABLE 10

| Probe Hybridized | Portion of Exon Cont. in Probe | Portion of Intron Cont. in Probe | Size (kb) of Hind III Bands Detected with Probe | Source of DNA that Hybridized to Probe |
|---|---|---|---|---|
| Probe A | 1 | | 2.1 | cosmid 55A11 |
| probe AF-AR | 1 | | 2.3, 2.1, 18 | placental |
| probe 1.2 | 2 | | 2.1 | cosmids 55A11 and 65G7 |
| probe 3.8 | 1, 2 | 1 | 1.7, 2.3 | cosmids 55A11 and 28 65G7 |
| probe BF-BR | 2 | | 2.3, 2.1, 1.8 | placental |
| probe CF-CR | 3, 4 | | 2.3, 1.8 | cosmids 55A11 and 65G7 |
| Probe C | 4, 5 | | 1.8 | cosmids 55A11 and 65G7 |
| Probe C | 4, 5 | | .4 | cosmid 225B8 |
| probe EF-ER | 5 | | 3.0, 1.8, .4 | placental |
| probe EF-ER | 5 | | .4 | cosmid 225B8 |
| probe EF-ER | 5 | | | cosmids 55A11 and 65G7 |
| probe EF-ER | 5 | | .4, 3.0 | cosmid 74B1 |
| probe FF-FR | 5 | | .4, 1.4 | cosmid 225B8 |
| probe GF-GR | 5, 6 | | 1.4, 2.8 | cosmids 74B1 and 225B8 |
| Probe D | 5, 6 | | 1.4, 2.8 | cosmids 74B1 and 225B8 |
| Probe E | 6, 7 | | 1.7, 2.0 | cosmid 225B8 |
| Probe E | 6, 7 | | 2.0 | cosmid 69B12 |
| probe M1.4 | 7 | | 2.0 | placental |

To confirm the positions and to rule out additional HindIII sites within the introns, long range PCR™ amplification using Elongase (Life Technologies) was performed and the resulting amplified genomic fragments were digested with HindIII and analyzed by gel electrophoresis. Some of the amplified products were hybridized back to HindIII digested genomic cosmid and placenta DNA to confirm the specificity of the amplification. Cosmid 28 was used as a template for introns 1,2, and 3 and cosmid 81 was used as a template for introns 4, 5 and 6. Primers AF-BXR generated a 3.8-kb band containing 145 bps from exon 1, ~3.6 kb from intron 1, and 87 bps from exon 2. When digested with HindIII, ~1.7 kb, ~1.2 kb , and ~0.9 kb bands were produced. Probe A hybridized to the 0.9 kb fragment and probe BF-BR hybridized to the 1.2-kb fragment.

The 1.7 kb band was not seen with hybridization when using the pml 0.1 cDNA probe however it is seen on cosmid 18 DNA with hybridization of the p3.8 kb probe. The 1.7-kb fragment is a single HindIII fragment made up entirely of intronic DNA. The 0.9-kb fragment hybridizes to the ~2.1-kb HindIII band of exon 1 and the 1.2-kb fragment hybridizes to the 2.3-kb HindIII band of exon 2. Intron 2 showed no digestion with HindIII. For intron 3 there was no noticeable digestion of the fragments because the primers used were very close to the HindIII restriction sites. Primer pair EF-ER produced a ~2.8-kb fragment that was reduced to ~2.1-kb, ~0.5-kb and ~0.25-kb bands when digested with HindIII. When hybridized back to cosmid DNA the ~2.8-kb fragment identified an ~1.8-kb, 2.1 -kb, and ~0.4-kb HindIII bands.

Thus, an 2.1-kb HindIII fragment lies within intron 4. The ~4.2-kb fragment (83 bp from exon 5, ~4.0-kb from intron 5, and 69 bp from exon 6) generated by primer pair GF,GR was reduced to ~1.35-kb and ~2.8-kb fragments. The ~2.6-kb fragment generated by primer pair HF,HR (53 bp from exon 6, ~2.4-kb from intron 6, and 98-bp from exon 7 and 3' untranslated region) was reduced to an ~1.7-kb and ~0.9-kb fragments These results confirmed the presence of only one HindIII site within each of introns 5 and 6. A genomic map displaying the size of the introns and the relative position of HindIII sites is shown in FIG. 15.

5.7 Example 7

Lack of p16$^{INK4A}$ and/or pRB in Resected NSCLC Correlates with Locally Advanced Disease The tumor suppressor gene CDKN2/p16$^{INK4}$, located on 9p21 is frequently inactivated in diverse human tumors by homozygous deletions or de novo methylation of the 5'CpG island. A reciprocal relationship has been demonstrated between pRB inactivation and a lack of p16 protein expression in human lung cancer cell lines and primary tumors. The expression of p16 and pRB in 39 resected primary NSCLC tumors was examined by western blot analysis. The results were correlated with clinico-pathologic features such as histology, tumor size, nodal metastases and pleural invasion. Ten tumors (26%) were p16(−)/pRB(+); 12 (31%) were p16(+)/pRB(−); 5 (13%) were p16(−)/pRB(−); 12 (31%)

were p16(+)/pRB(+). Thus, 27 (69%) tumors were p16(−) and/or pRB(−). Tumors lacking p16 and/or pRB were significantly larger than p16(+)/pRB(+) tumors (median size 4 vs. 2.75 cm; p=0.02). However, p16 expression alone did not correlate with any clinico-pathologic features. These studies suggest that the absence of p16 and/or pRB is the most common abnormality in NSCLC and support a common growth-regulatory mechanism that is disrupted in the majority of lung cancers (FIG. 16).

5.8 Example 8

Mapping the Chromatin Structure of the Type I Interferon Gene Cluster on the Short Arm of Human Chromosome 9

This example describes the construction of a long-range restriction map of the type I human interferon (IFN) gene cluster which maps to a 450-kb region on chromosome 9, band p21. The gene family consists of 1 beta gene (IFNBI), 13 alpha (INFA) genes, 1 alpha pseudogene (IFNAP), 1 omega (IFNW) gene, 6 IFNW pseudogenes, and 4 unclassified pseudogenes (IFNP). The chromatin structure has been determined for the type I IFN gene family in a human hematopoetic cell line, using the Li 2'3'-diiodosalicylate (LIS) scaffold attachment region (SAR) mapping assay. Six separate IFNA or IFNW coding sequences were devoid of attachment sites. By hybridization of the IFNA2 and IFNW1 coding regions to non-SAR and SAR DNA fractions, 22 strong SARs were mapped to the flanking regions of the 13 IFNA true genes, 3 strong SARs to the flanking regions of 2 IFNW true gene members, and 2 strong SARs flanked 1 IFNW pseudogene. Three weak SARs were mapped in the flanking region of two IFNW pseudogenes and one weak SAR mapped to the flanking region of an IFNA true gene. Likewise, one 3' strong SARs and 2 5' strong SARs flanking IFNA2 were identified, whereas both IFNP11 and IFNP12 were flanked by weaker SARs. A similar pattern of SAR distribution throughout the type I IFN gene family was observed in a human glioma cell lines, suggesting that the structural organization in which SARs define this region into a series of small DNA loop domains is conserved in different tissue types.

5.8.1 Materials and Methods 5.8.1.1 Cell Lines

For isolation of the DNA scaffold fraction, the chronic myelogenous leukemia (CML) cell line BV173, and the glioma cell line, U373, were used. BV173 cells are lymphoblastoid precursor B-cells derived from a CML patient in blast crisis. The primary clone in this cell line contains one normal chromosome 22 and three copies of the rearranged order. In BV173 the IFN gene cluster on 9p is in a normal germline configuration. U373 cells were derived from a human glioblastoma multiforme tumor. U373 demonstrates functional and biological heterogeneity in vitro and in tumors passed in vivo in nude mice. Molecular analysis show no rearrangement at the IFN locus on chromosome 9.

5.8.1.2 Cell Cultures

BV173 cells were maintained in RPMI medium supplemented with 10% fetal calf serum, 1% hepes, sodium bicarbonate (amount adjusted per lot), 1% penicillin, and streptomycin. A fraction of the cells were strained with Trypan Blue to estimate cell viability, and were counted every four days. To maintain the line, the cells were plated at $0.5\times10^6$ density and divided 1:4 every 4 days. U373 cells are adherent cells and were maintained in DMEM and 10% FCS in 175 cm tissue culture flasks.

5.8.1.3 Nuclei and Nuclear Scaffold Isolation—In Vivo SAR Mapping

Methods for isolation of BV173 and U373 cell nuclei and scaffolds have been described elsewhere (Stirssel et al., 1995). For these studies, approximately $1\times10^6$ cells/ml with 90–100% viability were extracted per study. U373 cells were grown to log phase at 80=9% confluency (approximately $5-50\times10^6$), placed on ice and washed two times in phosphate buffered saline, then the cells were removed gently from the flask using a rubber policeman.

5.8.1.4 Pellet (Scaffold) and Supernatant (Loop) DNA Purification

To obtain purified pellet and supernatant DNA, each fraction was treated after isolation in a standard solution of Tris buffer containing SDS and proteinase K. Scaffold proteins were then extracted with phenol, phenol/chloroform/isoamyl alcohol, and chloroform/isoamyl alcohol. DNA was ethanol-precipitated and resuspended in sterile water.

5.8.1.5 DNA Clones

The IFNA2 gene was previously mapped and cloned within two overlapping human genomic clones (λ1-1, a 10 kb HindIII fragment, λ1-2, a 12 kb BamHI fragment). The 10 kb HindIII clone extended further 3' from the gene than the 12.0 kb BamHI clone. A third λ clone (1-3, a HindIII 11.6 kb clone, which overlapped the 5' end of the BamHI fragment and included the IFNP11 gene was also isolated. A fourth 20 kb HindIII % clone 1-4 included IFNP12 and IFNA8 genes. For IFNA5, a 19 kb BamHI λ clone was mapped, and fragments containing the coding region and the 3' gene region were isolated and used as probes.

5.8.1.6 Probes and Isolation of Inserts

The technique of Vaux was used to isolate DNA fragments from agarose gels for use as probes on Southern blots. Restriction fragments from λ clones containing the IFNA5, IFNA2, IFNP11, IFNP12 coding regions, and their 5' and 3' flanking regions, were recovered and used as probes in this study. The IFNW1 coding region was recovered from agarose and used as a probe. Additional cloned coding regions isolated from plasmids and used for hybridization to supernatant and pellet Southern blots were the IFNWI, IFNBI, the 0.73 kb BamHI exons 5,6,7,9,10 MLL cDNA, the 0.4 kb PstI MLL exons 4,5, and the BCR PstI cDNA 3' fragment provided by Owen Witte. Additional DNA fragments used as probes on supernatant and pellet genomic fractions were the IFNBI 1.5 kb EcoRI/PstI 5' SAR fragment, and the ph10, ph15 DNA fragments from the BCR gene 1st 90 kb intron.

5.8.1.7 Southern Blot, DNA Hybridization, and Autoradiography

For SAR analysis 4 pg (determined by optical density readings) of the supernatant and pellet fractions per study were used for Southern blot analysis. All prehybridizations and hybridizations followed standard methodology. Autoradiographs of Southern blots were scanned (HP Scanjet II cx) and the label of specific bands was quantitated by MOCHA (Jandel, San Rafael, Calif.) as the mean intensity of the negative image multiplied by the band area (number of pixels). The relative strength (R) of a specific DNA segment to partition in the pellet fraction was estimated as the band intensity in the pellet divided by the sum of intensities of pellet plus supernatant (R=IP P+IS). Various gene fragments were used as positive and negative control fragments to set standards for binding affinity and were the following: 1) positive control gene fragments showing >70% (R=70) enrichment into the pellet were the IFNBI 5' SAR detected with the 1.5 kb EcoRI/PstI probe, and the MLL breakpoint cluster region telomeric SAR detected with the 0.73 kb BamHI cDNA probe; 2) negative control fragments showing negligible binding with <30% (R=<30) enrichment into the pellet were the IFNBI coding region, the MLL breakpoint cluster region non-SAR fragments detected with the 0.73 kb BamHI cDNA probe, and several non-SAR fragments from the BCR 3' gene region detected with the BCR PstI 3' probe; 3) weaker binding control fragments demonstrating 40–60% enrichment into the pellet (R=40–60) were IFNBI 3' weak SAR detected with the IFNBI coding sequences, the MLL weak centromeric SAR detected with the 0.4 kb PstI cDNA probe, and the BCR weak intronic SARs mapping within the 1st intron detected with probesPh 10, 15. For a particular DNA fragment detected in the supernatant or pellet, these values equal the total amount of this DNA fragment in each genomic fraction. Thus, this value represents the total pellet or supernatant enrichment for this DNA fragment in the whole genome.

5.8.2 Results 5.8.2.1 SARs and the IFNA and IFNW Genes in BV173 Hematopoetic Cells IFNA genes, cut with HindIII and EcoRI were mapped for SARs (FIG. 17A). BglII supernatant and pellet fragments were also analyzed. In addition, HindIII, EcoRI and BglII supernatant and pellet fragments containing IFNW1 coding regions were mapped for SARs. These probes hybridized only to genes within their own family as previously described. Using detailed restriction maps and evaluating the enrichment patterns for all these gene fragments, SAR localization was obtained (FIG. 17A, FIG. 17B, Table 11).

TABLE 11

| | Gene SAR Location | |
|---|---|---|
| Non-SAR IFN fragments R = ≦30 | coding regions | |
| IFNA1 | " | |
| IFNA2 | " | |
| IFNA8 | " | |
| IFNA9 | " | |
| IFNA15 | " | |
| IFNA18 | " | |
| Strong Specific IFN SARs | 5' SAR | 3' SAR |
| IFN21 | — | 3' SAR |
| IFNA7 | — | 3' SAR |
| IFNA16 | 5' SAR | 3' SAR |
| IFNA17 | 5' SAR | 3' SAR |
| IFNA14 | 5' SAR | — |
| IFNA5 | 5' SAR | 3' SAR |
| IFNA13 | 5' SAR | — |
| IFNW19 | — | 3' SAR |
| Total = 11 SARs | IFNA 5' SARs = 5 | IFNA 3' SARs = 5 IFNW 3' SARs = 1 |
| Strong SARs Mapping both 5' and 3' | | |
| IFNW1 | | |
| IFNA4 | | |
| IFNA10 | | |
| IFNA6 | | |
| IFNA1 | | |
| IFNA8 | | |
| IFNA2 | | |
| IFNPW18 | | |
| Total = 16 strong SARs | | |
| weak SARs | 5' SAR | 3' SAR |
| IFNA21 | 5' SAR | |
| IFNPW15 | 5' SAR | 3' SAR |
| IFNPW9 | | 3' SAR |
| total = 4 weak SARs | | |

In Table 11, non-SAR and SAR mapping results are illustrated using the IFNA and IFNW coding regions as probes to supernatant and pellet DNA fractions. Top set of columns show non-SAR DNA fragments detected with the IFNA2 and IFNW1 coding regions. Middle set of columns demonstrate 8 IFN genes and the number and location of specific SARs to the 5' and 3' flanking gene regions. Note, that the 3' SAR of IFNA5 (underlined) was mapped using cloned DNA fragments. All these IFN SARs mapped to DNA fragments containing coding sequences plus 3' flanking DNA. Bottom set of columns (left) identify strong SARs mapping to both the 5' and 3' flanking regions of the IFN genes. The bottom (right) column represents the location of weak SARs to the 5' and/or 3' flanking regions of one IFNA true gene and two IFNPW genes.

Several supernatant enriched fragments (R≦30) were observed containing only the coding regions or coding regions plus short flanking DNA stretches for 3 IFNA and 3 IFNW genes (Table 11). These results demonstrated that 6 IFN coding regions are scaffold free regions. Thus it is likely that all the IFN coding regions do not represent SARs. Three different groups of fragments were also observed which were enriched in the pellet fraction (R≧70) (Table 10). The first group of fragments, contained coding sequences plus 5' flanking DNA, the second group contained sequences with only 3' flanking DNA. These fragments allowed the mapping of SAR locations very specifically to either the 5' or 3' flanking regions. Five strong SARs were mapped to the 3' flanking region, and five strong SARs to the 5' flanking regions of 7 IFNA genes. The 3' SAR of IFNA5 was mapped using specific DNA fragments from a lambda clone. One strong SAR mapped, to the 3' flanking region of one IFNW gene. The third group of pellet enriched DNA fragments contained coding regions and approximately equal amounts of both 5' and 3' flanking DNA partitioning into the pellet fraction (R≧70). It appeared that high affinity SARs flanked these gene coding sequences. First, six IFN coding regions were devoid of SARs. Second, in studies where strong SARs could be specifically mapped to the 5' or 3' flanking gene regions, three genes contained strong SARs in both flanking regions (Table 11). Finally, one fragment which extended equally both 5' and 3' of IFNA2, SARs were specifically mapped to the flanking regions using cloned DNA fragments. Two strong SARs were identified in the third group of pellet enriched DNA fragments: one in the 5' and one in the 3' gene regions. Results demonstrated 12 strong SARs to 6 IFNA gene flanking regions, and four strong SARs to 2 IFNW flanking regions.

Two final groups of DNA fragments were analyzed which contained IFN genes demonstrating a more equal distribution between the pellet and supernatant fractions (R=40–60). The first group of DNA fragments overlapped sections of previously identified strong SARs, indicating these regions probably contained fragments of strong SAR binding sites. The second group of weaker binding DNA fragments contained separate weak SARs. Weak SARs were mapped to the 5' flanking region of an IFNA true gene (I SAR), to the 3' flanking region of an IFNWP gene (1 SAR), and to the 3' and 5' flanking region of an IFNWP gene (2 SARs).

5.8.2.2 IFNA2 Telomeric and Centromeric SARs in BV173 Cells

Initially observed was a 5.0 kb EcoRI pellet enriched fragment after hybridizing the IFNA2 coding region to supernatant and pellet fractions. This fragment contained the IFNA2 coding region plus both 5' and 3' flanking sequences (FIG. 17A). To see if SARs mapped to the gene flanking regions, specific DNA fragments representing the flanking regions of IFNA2 were hybridized to supernatant and pellet fractions. Hybridization of proves a, d (IFNA2 coding region) h, and i to supernatant and pellet fractions, showed a 1.2-kb HindIII/EcoRI, a 0.4-kb BglII, a 1.6-kb EcoRI/BglII and a 1.0-kb BglII/BamHI fragment, all of which enriched to the supernatant fraction and thus defined the location of non-SARs (FIG. 17A, FIG. 19A, and FIG. 19B). Hybridization of probes b, c, f, and g, to various single and double digests showed pellet enrichment for a 4.6-kb EcoRI, a 2.65-kb EcoRI/BglII, a 3.1-kb EcoRI, and a 1.1-kb EcoRI fragment, thus identifying two strong affinity SARs, one 3' (SAR1) and one 5' (SAR2) of the IFNA2 gene (FIG. 19A). Hybridization of probes j and k (FIG. 19B) identified an 0.7-kb EcoRI fragment (SAR3) and a 1.8-kb BamHI/EcoRI fragment (SAR3) almost exclusively in the pellet fraction. Probe l identified a 3.0-kb EcoRI/BglII fragment which distributed approximately equally between both fractions (FIG. 19A and FIG. 19B).

The region containing the IFNA2 SAR3 and the adjacent weaker binding region, were further defined with restriction enzymes which cut more frequently (4-bp recognition sites) to map the scaffold binding sites. Hybridizing probe l to Sau3AI, HaeIII, and EsaI supernatant and pellet fractions, several small supernatant, weak, and pellet enriched DNA fragments were identified (FIG. 20). The SAR3 was separated by 707 bp of non-scaffold DNA from a weak affinity SAR (SAR4) (FIG. 20). One additional weak SAR mapped between IFNPJL and IFNP12 (SAR5) (FIG. 19A), and one mapped just 3' to IFNP12 (SAR6) (FIG. 19A).

5.8.2.3 SARs and the IFNA gene cluster in U373 glioma cells

To determine if these SARs are conserved in different tissue types, the IFNA SARs were analyzed in U373 glioma cells. As shown in FIG. 20, HindIII and EcoRI supernatant and pellet fragments were analyzed for SARs using the IFNA2 probe. BglII supernatant and pellet fractions were also analyzed for SARS. A pattern of hybridization similar to that seen with BV173 cells was observed. These results indicate that SARs are conserved between two different cell types (hematopoetic and glioma cells), in the IFNA2 region. In addition, it was possible to demonstrate that SAR3 and the IFNBI 5' SAR also showed pellet enrichment similar to that in BV173 cells.

5.8.2.4 Type 1 IFN SARs

The 450-kb region containing the IFNA and the IFNW genes as shown by detailed analysis and the 20-kb region containing IFNA2, IFNP11 and IFNP12 is a scaffold rich region (FIG. 16, FIG. 18, and FIG. 19A). The relative scaffold binding affinity was calculated for 17 different IFNA gene fragments in both BV173 and U373 cells. Enrichment patterns were similar for both cell lines. Twenty DNA fragments from the IFNA2, IFNP11 and IFNP12 cloned region were measured (FIG. 17A, FIG. 17B, FIG. 18, FIG. 19A, FIG. 19B, and FIG. 21). The strength of scaffold binding between the IFN gene fragments and the different positive and negative control fragments compared well. For example, all IFNA pellet enriched fragments with $R \leq 30$ demonstrating negligible binding compared well with the IFNBI coding region (R=3), and non-SAR fragments from the MLL breakpoint cluster region (R=7) and BCR 3' gene regions (R=13). None of these fragments (IFNA, IFNW or controls) were observed partitioning into the pellet non-specifically because of their high molecular weight in multiple studies. Thus, the results demonstrate specific scaffold binding for these gene regions.

In BV173 and U373 cells it was not possible to assign SARs to a few regions because the restriction sites were not mapped and specific DNA probes were not available. These gene regions included the 3' region of IFNA14 and the 5' region of IFNWP5 (FIG. 18). Additional regions not mapped were the 5' region of IFNP23, and 5' and 3' regions of IFNAP22, and three 50 kb regions containing no known coding sequences: 1) the region between the IFNBI gene and the first group of IFNW and IFNA genes 2) the region between the first and second group of IFNW, IFNA genes, and 3) the region between the last group of IFNA and IFNW genes and the IFNA1, IFNP23 and IFNWP19 genes (FIG. 18).

5.8.3 Discussion

35 SARs have been mapped within the IFNA and IFNW gene cluster in BV173 cells. 23 IFNA SARs have also been shown to map to the same locations in U373 cells. The chromatin organization of the IFN genes has revealed several important features including coding regions flanked by SARs, large high affinity SARs demonstrating cooperative interactions and the association of weak SARs with some of the pseudogenes. It is probable that the IFN gene family arose from one primordial gene followed by gene duplication and divergence. The IFNA and IFNW genes have clearly arisen through gene duplication and gene conversion events plus an inversion.

At least some pseudogenes are associated with weak SARs. The IFNPW9 gene is probably associated with a 3' weak SAR and the IFNPW15 is also flanked by 5' and 3' weak SARs. However, the IFNWP 18 gene was flanked by strong SARs. Since only the IFNPW9 and IFNPW15 pseudogenes were able to be mapped using the IFNW1 coding region as a probe, it was not possible to confirm if these weak SARs represent portions of high affinity SARs.

The example demonstrates that IFNA gene family SARs map to the same locations in U373 glioma cells as those found in BV173 hematopoetic cells. The same pattern of SARs in two different cell types suggest an importance to conserve the chromatin structure of the family. Both hematopoetic and glial cells are derived from the same precursor pluripotent stem cells during development. Early in development blood macrophages migrate to brain tissue, where they differentiate into glial cells.

The model for the higher order structure of the IFN gene family proposes a series of loop domains ($\leq 10$ kb) flanked by SARs. Some small loops contain an IFN gene with its promoter and regulatory sequences flanked by SARs. Other small loops contain pseudogenes also flanked by SARs that, at least in some cases, showed weaker scaffold binding. Since most, if not all, 22 members of the IFN gene family are flanked by SARs, it is apparent that the duplication of IFN sequences that appear to have generated this complex locus in evolution has also involved duplication of flanking scaffold attachment sites.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

6. REFERENCES

The following literature citations as well as those cited above are incorporated in pertinent part by reference herein for the reasons cited in the above text:

U.S. Pat. No. 4,608,251
U.S. Pat. No. 4,601,903
U.S. Pat. No. 4,599,231
U.S. Pat. No. 4,599,230
U.S. Pat. No. 4,596,792
U.S. Pat. No. 4,596,770
U.S. Pat. No. 3,791,932
U.S. Pat. No. 4,174,384
U.S. Pat. No. 3,949,064

Ahuja et al., "Abnormalities of the retinoblastoma gene in the pathogenesis of acute leukemia," Blood, 78:3259, 1991.

Allegra et al., "Cytogenetic alterations in laryngeal carcinomas," Arch Otolaryngol Head Neck Surg., 118:1320–2, 1992.

Altschul et al., J. Mol. Biol., 215:403–410, 1990.

Andersen et al., "Genetic alterations of the tumor suppressor gene regions on 3p, 11p, 13q 17p and 17q in human breast carcinomas," Genes Chromosome and Cancer, 4:113–121, 1992.

Arap et al., "Replacement of the p16/CDKN2 gene suppresses human glioma cell growth," Cancer Res., 55:1351–1354, 1995.

Bennett et al., "Proposals for the classification of the acute leukemias," Br. J. Haematol, 33:451, 1976.

Bieche et al., "Loss of heterozygosity on chromosome 7q and aggressive primary breast cancer," Lancet 339:139–143, 1992.

Bigner et al., "Specific chromosomal abnormalities in malignant human gliomas," Cancer Res. 58:405–411, 1988.

Bohlander et al., "A method for the rapid sequence-independent amplification of microdissected chromosomal material," Genomics, 13:1322–1324. 1992.

Bohlander et al., "Mapping of a putative tumor suppressor gene on chromosome 9 band p21-22 with microdissection probes," Genomics, 24:211, 1994.

Bohlander et al., "Sequence-independent amplification and labeling of yeast artificial chromosomes for fluorescence in situ hybridization," Cytogenet. Cell Genet., 65:108–110, 1994.

Borrensen et al., "Amplification and protein expression of the neulHer-2/c-erbB-2 protooncogene in human breast carcinomas: relationship to loss of sequences on chromosome 17, family history and prognosis," Br. J. Cancer, 60:585–590, 1990.

Buckler et al., "Exon amplification: a strategy to isolate mammalian genes based on RNA splicing," Proc. Nail. Acad. Sci. USA, 88:4005–4009, 1991.

Cairns et al., "Rates of p16 (MTSI) mutations in primary tumors with 9p loss," Science, 265:415–416, 1994.

Caldas et al., "Frequent somatic mutations and homozygote deletions of the p16 (MTSI) gene in pancreatic adenocarcinoma," Nature Genet., 8:27–31, 1994.

Call et al., "Isolation and characterization of a zinc finger polypeptide gene at the human chromosome 11 Wilms'tumor locus," Cell, 60:509–520, 1990.

Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Cannon-Albright et al., "Assignment of a locus for familial melanoma, MLM, to chromosome 9p13-p22, Science, 258:1148–1152, 1992.

Carerra et al., Proc. Natl. Acad. Sci. USA, 81:2665–2668, 1984.

Chen et al., "P16 deletions in malignant mesotheliomas," Cancer Res., 54:5547–5551, 1994.

Cheng et al., "Homozygous deletions within 9p21-p22 identify a small critical region of chromosomal loss in Human Malignant Mesotheliomas," Cancer Res., 53:4761–4763, 1993.

Cheng et al., Cancer Res., 54:5547–5551, 1994.

Chilcote et al., "Lymphoblastic leukemia with lymphomatous features associated with abnormalities of the short arm of chromosome 9," N. Engl. J. Med., 313:286, 1985.

Coleman et al., Cancer Res., 54:344–348, 1994.

Cowan and Francke, "Cytogenetic analysis in melanoma and nevi," Cancer Treat. Res., 54:3–16, 1991.

Cropp et al., "Loss of heterozygosity on chromosome 17 and 18 in breast carcinoma: two additional regions identified," Proc. Natl. Acad Sci. USA, 87:7737–7741, 1990.

Della et al., Biochem. J., 281:533–538, 1992.

Devilee et al., "Allelotype of human breast carcinoma: a second major site foe loss of heterozygosity is on chromosome 6q," Oncogene, 6:1705–1711, 1991.

Díaz et al., "Structure of the human type-I interferon gene cluster determined from a YAC clone contig," Genomics, 22:540–552, 1994.

Díaz et al., "Deletion of interferon genes in acute lymphoblastic leukemia," New Eng. J. Med, 322:77–82, 1990.

Díaz et al., "Homozygous deletion of the alpha and beta-1 interferon genes in human leukemia and derived cell lines," Proc. Natl. Acad Sci., USA, 85:5259–5263, 1988.

Dreyling et al., "A method for screening arrayed cosmid libraries with mega insert yeast artificial chromosomes," Nucl. Acids Res., 23:1085–1086, 1995.

Dreyling et al., "Detection of CDKN2 deletions in tumor cell lines and primary glioma by Interphase Fluorescence in situ Hybridization," Cancer Research, 55:984–988, 1995.

Dreyling et al., "Detection of p16 gene deletions in leukemia derived cell lines by interphase in situ hybridization," Haematol. Blood Transfs., In press.

Dreyling et al., "Detection of the tumor suppressor region on 9p2l in acute leukemia by fluorescence in situ hybridization to interphase nuclei," Blood, 84:298, 1994.

Dreyling et al., Blood, 86:1931–1938, 1995.

Duyk et al., "Exon trapping: a genetic screen to identify candidate transcribed sequences in cloned mammalian genomic DNA," Proc. Natl. Acad Sci. USA, 87:8995–8999, 1990.

El-Deiry et al., "WAF1, a potential mediator of p53 tumor suppression," Cell, 75:817–825, 1993.

Erickson et al., "Identification of breakpoints in t(8;21) acute myelogenous leukemia and isolation of a fusion transcript AMLI/ETO, with similarity to drosophila segmentation gene, runt," Blood, 80:1825–1831, 1992.

Fearon et al., "Identification of a chromosome 18q gene that is altered in colorectal cancers," Science, (Washington DC), 247:49–56, 1990.

Feinberg and Vogelstein, Ann Biochem, 132:6–13, 1983.

Felgner et al., "Lipofection: a highly efficient, lipid-mediated DNA transfection procedure," Proc. Natl. Acad. Sci. USA, 84:7413–7417, 1987.

Fenaux et al., "Mutations of the p53 gene in B-cell lymphoblastic acute leukemia," Leukemia, 6:42, 1992.

Fountain et al., "Homozygous deletions within human chromosome band 9p21 in melanoma," Proc. Natl. Acad. Sci. USA, 89(21):10557–61, 1992.

Friend et al., "A human DNA segment with properties of the gene that predisposes to retinoblastoma," Nature (London), 323:643–646, 1986.

Garrard, "Chromosomal loop organization in the eukaryotic genome. In: Eckstein, Lilley, DMJ, (Eds.) Nucleic Acids

*and Molecular Biology,* Springer-Verlag Berlin, Heidelberg, 4:163–175, 1990.

Gefter et al., *Somatic Cell Genet.*, 3:231–236, 1977.

Giani et al., "Mutation rate of the CDKN2 gene in malignant gliomas," *Cancer Res.*, 54:6338–6339, 1994.

Goding, "Monoclonal Antibodies: Principles and Practice," pp. 60–74. 2nd Edition, Academic Press, Orlando, Fla., 1986.

Gombart et al., "Alterations of the CDK4/MTSI (cyclin-dependent kinase 4 inhibitor/multiple tumor suppressor 1) gene in uncultured and cultured B-cell lymphoma, *Blood*, 84:445, 1994.

Guan et al., "Growth suppression by p18, a p16INK4/MTS1- and p14INK4B/MTS2-related CDK6 inhibitor, correlates with wild-type pRb function," *Genes and Dev.*, 8:2939–2952, 1994.

Hall et al., "Linkage of early onset familial breast cancer to chromosome 17q21," *Science*, 250:1684–1689, 1990.

Hannon and Beach, "p15$^{INK4B}$ is a potential effector of TGF-β-induced cell cycle arrest," *Nature*, 371:257–261, 1994.

Harlow and Lane, "Antibodies: a laboratory manual," Cold Spring Harbor Laboratory, Cold Spring Harbor, N.Y. 1988.

He et al., "CDK4 amplification is an alternative mechanism to p16 homozygous deletion in glioma cell lines," *Cancer Res.*, 54:5804–5807, 1994.

Hebert et al. "Candidate tumor-suppressor genes MTSI (p16 $^{INK4A}$) and MTS2(p15 $^{INK4B}$) display frequent homozygous deletions in primary cells from T- but not from B-cell lineage acute lymphoblastic leukemia," *Blood, 84:4038, 1994.*

Henco et al., "Structural relationship of human interferon ax genes and pseudogenes," *J. Med. Biol.*, 185:227–260, 1988.

Hermanson et al., "Rescue of end fragments of yeast artificial chromosomes by homologous recombination in yeast," *Nucl. Acids Res.*, 19:4943–4948, 1991.

Hussussian et al., "Germline mutations in familial melanoma," *Nat. Genet.*, 8:15–21, 1994.

Islam et al., "A gene for the suppression of anchorage independence is located in rat chromosome 5 bands q22-23, and the rat ax-interferon locus maps at the same region," *J. Cell Sci.*, 92:147–162, 1989.

James et al., "Clonal genomic alterations in glioma malignancy stages, *Cancer Res.*, 48:5546, 1988.

James et al., "Chromosome 9 deletion mapping reveals interferon alpha and interferon beta-1 gene deletions in human glial tumors," *Cancer Res.*, 51(6):1684–8, 1991.

James et al., "Localization of chromosome 9p homozygous deletions in glioma cell lines with markers constituting a continuous linkage group," *Cancer Res.*, 53:3674–3676, 1993.

Jameson and Wolf, *Compu. Appl. Biosci.*, 4(l):181–6, 1988.

Jen et al., "Deletions of p15 and p 16 in brain tumors," *Cancer Res.*, 54:6353–6358, 1994.

Jonasson et al., "The analysis of malignancy by fusion.VII. Cytogenetic analysis of hybrids between malignant and diploid cells and of tumors derived from them," *J. Cell Sci.*, 24:217–254, 1977.

Kacker et al., "Consistent karyotypic abnormalities in human malignant melanomas," *Anticancer Res.*, 10:4, 859–71, 1990.

Kamatani et al., "Selective killing of human malignant cell lines deficient in methylthioadenosine phosphorylase, a purine metabolic enzyme," *Proc. Natl. Acad. Sci. USA*, 78:1219–1223, 1981.

Kamb et al., "A cell cycle regulator potentially involved in genesis of many tumor types," *Science*, 264:436–440, 1994.

Kamb et al., "Analysis of the p16 gene (CDKN2) as a candidate for the chromosome 9p melanoma susceptibility locus," *Nat. Genet.*, 8:22–26, 1994.

Kinzler et al., "Identification of FAP locus genes from chromosome 5q21," *Science*, 253:661–665, 1991.

Klinger et al., "Human chromosomes which affect tumorigenicity in human cell hybrids," *Somat. Cell Mol. Genet*, 7:699–712, 1981.

Kowalczyk and Sandberg, "A possible subgroup of ALL with 9p-," *Cancer Genet. Cytogenet.*, 9:383, 1983.

Kwiatkowski and Dfaz, *Hum. Mol. Genet.*, 1:658, 1992.

Kyte and Doolittle, *J. Mol. Biol.*, 157(1):105–132, 1982.

Le Beau, "Cytogenetic analysis of hematological malignant diseases," *The ACT cytogenetics laboratory manual*, in M. J. Barch (Eds): New York, Raven Press Ltd., p. 395, 1994.

Lengyel, "Tumor suppressor genes: news about the interferon connection," *Proc. Natl. Acad. Sci. USA*, 90:5893–5895, 1993.

Lippman and Pearson, "Rapid and sensitive protein similarity searches," *Science*, 227:1435–1441, 1985.

Lovett et al., "Direct selection: A method for the isolation of cDNAs encoded by large genomic regions," *Proc. Natl. Acad. Sci. USA*, 88:9628–9632, 1991.

Lukeis et al., "Cytogenetics of non-small cell lung cancer: analysis of consistent non-random abnormalities," *Genes Chromosome Cancer*, 2(2), 116–24, 1990.

Lydiatt et al., *Genes, Chromosomes and Cancer*, 13:94–98, 1995.

Maloy et al., "Microbial Genetics" 2nd Edition. Jones and Bartlett Publishers, Boston, Mass., 1994.

Maniatis et al., "Molecular Cloning: a Laboratory Manual," Cold Spring Harbor Laboratory, Cold Spring Harbor, N.Y., 1982.

Matsumura et al., "Detection of chromosome 17p loci in breast cancer cells detected by fluorescein in situ hybridization," *Cancer Res.*, 52:3474–3477, 1992.

Mirkovitch et al., "Organization of the higher order chromatin loop:specific DNA attachment sites on nuclear scaffold," *Cell*, 39:223–232, 1984.

Mitelman, "Catalog of Chromosome Aberrations in Cancer," 5th Ed., Wiley-Liss, 1994.

Mitelman, "Catalog of Chromosome Aberrations in Cancer," 4th Ed., Wiley Liss, 1991.

Mori et al., "Frequent somatic mutation of the MTSI/CDK4I (multiple tumor suppressor/cyclin-dependent kinase 4 inhibitor) gene in esophageal squamous cell carcinoma," *Cancer Res.*, 54:3396–3397, 1994.

Moyzis et al., "Human chromosome-specific repetitive DNA sequences: novel marker for genetic analysis," *Chromosoma*, 95:375–386, 1987.

Nakamaki et al., "p16-alterations in myeloid leukemias, *Blood*, 84:48, 1994.

National Center for Health Statistics, "Vital statistics of the United States," 1987," Vol. 2, *Mortality*, Part A, Washington, D.C.; Government Printing office, DHHS publication, no (PHS) 90–1101, 1990.

Nelson et al., "Alu polymerase chain reaction: a method for rapid isolation of human-specific sequences from complex DNA sources," *Proc. Natl. Acad. Sci. USA*, 86:6686–6690, 1989.

Nobori et al., "Absence of methylthioadenosine phosphorylase in human gliomas," *Cancer Res.*, 51:3193–3197, 1991.

Nobori et al., "Deletions of the cyclin-dependent kinase-4 inhibitor gene in multiple human cancers, Nature, 368:753–756, 1994.

Nobori et al., Cancer Res., 53:1098–1101, 1993.

Non Hodgkin's Lymphoma Pathologic Classification Project, "National Cancer Institute sponsored study of classification of non-Hodgkin's lymphoma: Summary and description of a working formulation for clinical usage," Cancer, 49:2112, 1982.

Ogawa et al., "Homozygous loss of the cyclin-dependent kinase 4-inhibitor (p16) gene in human leukemias," Blood, 84:2431, 1994.

Ohta et al., "Rarity of somatic and germline mutations of the cyclin-dependent kinase 4 inhibitor gene, CDK4I, in melanoma," Cancer Res., 54:5269–5272, 1994.

Okamoto et al., "Mutations and altered expression of p $16^{INK4}$ in human cancer," Proc. Natl Acad Sci., USA, 91:11045–11049, 1994.

Olopade et al., "Clinical significance of loss of the interferon genes in gliomas," Plenary session presentation American Society of Clinical Oncology. Proc. Amer. Soc. Clin. Oncol., 10:80, 1991.

Olopade et al., "Construction of a 2.8 megabase YAC contig and cloning of the methyladenosine phosphorylase (MTAP) gene from the tumor suppressor region on 9p21," Proc. Nat. Acad. Sci. USA, 92:6489–6493, 1995.

Olopade et al., "Homozygous loss of the interferon genes defines the critical region on 9p that is deleted in lung cancers," Cancer Res., 53:2410–2415, 1993.

Olopade et al., "Mapping of the shortest region of overlap of deletions of the short arm of chromosome 9 associated with human neoplasia," Genomics, 14:437–443, 1992.

Olopade et al., "Molecular analysis of deletions of the short arm of chromosome 9 in human gliomas," Cancer Res., 52:2523–9, 1992.

Orita et al., "Detection of polymorphisms of human DNA by gel electrophoresis as single-stranded conformation polymorphisms," Proc. Natl. Acad. Sci. USA, 86:2766–2770, 1989.

Parimoo et al., "cDNA selection: efficient PCR approach for the selection of cDNAs encoded in large chromosomal DNA fragments," Proc. Natl. Acad. Sci. USA, 9623–9627, 1991.

Pearson et al., Proc. Natl. Acad. Sci. USA, 85:2444–2448, 1988.

Petty et al., "Cutaneous malignant melanoma and atypical moles associated with a constitutional rearrangement of chromosomes 5 and 9," Amer. J. Med. Genet., 45(l):77–80, 1993.

Pollak and Hagemeijer, "Abnormalities of the short arm of chromosome 9 with partial loss of material in hematological disorders," Leukemia, 1:541, 1987.

Pomykala et al., "The cloning and characterization of two human glioma breakpoints," Molec. Cell Biol., 14:7604–7610, 1994.

Porterfield et al., "Functional Analysis of a tumor suppressor gene on human chromosome 9 in mouse xhuman somatic cell hybrids," Somatic Cell Molec. Genet., 20:391–400, 1994.

Porterfield et al., "Induction of senence in two human neoplastic cell lines by microcell transfer of human chromosome 9," Proc. Amer. Assoc. Cancer Res., 33:72, 1992.

Porterfield et al., "The use of methylthioadenosine phosphorylase activity to select for human chromosome 9 in interspecies and intraspecies hybrid cells," Somatic Cell Molec. Genet., 20:391–400, 1994.

Povey et al., Ann. Hum. Genet., 58:177–250, 1994.

Quesnel et al., "p16 homozygous deletions in acute lymphoblastic leukemia." Blood, 85:657, 1994.

Rowley et al., "Mapping chromosome band 11q23 im human acute leukemia with biotinylated probes: Identification of 11q23 translocation breakpoints with a yeast artificial chromosome," Proc. Natl. Acad. Sci. USA, 87:9358–9362, 1990.

Sambrook et al., "Molecular Cloning: A Laboratory Manual," 2nd Edition; Cold Spring Harbor Laboratory, Cold Spring Harbor, N.Y., 1989.

Sanger et al., "DNA sequencing with chain terminating inhibitors," Proc. Natl. Acad. Sci. USA, 74: 5463–5467, 1977.

Schmidt et al., "CDKN2 (p16/MTSI) gene deletion or CDK4 amplification occurs in the majority of glioblastomas," Cancer Res., 54:632–6324, 1994.

Schneider et al., "Primary structure of the human transferrin receptor deduced from the mRNA sequence," Nature, 311:675, 1984.

Serrano et al., "A new regulatory motif in cell-cycle control causing specific inhibition of cyclin D/CDK4," Nature, 366:704–707, 1993.

Serrano et al., "Inhibition of Ras-induced proliferation and cellular transformation by p16 NK4," Science, 267:249–252,1995.

Serrano et al., Nature, 366:704–707, 1993.

Sheffield et al., "The sensitivity of single-strand conformation polymorphism analysis for the detection of single base substitutions, Genomics, 16:325, 1993.

Sherr, "Mammalian G1 cyclins," Cell, 73:1059–1065, 1993.

Smith and Johnson, "Single step purification of polypeptides expressed as fusions with glutathione S-transferase," Gene, 67:31–40, 1988.

Sperry et al., "Dysfumction of chromosomal loop attachment sites: Illegitimate recombination linked to matrix association regions and topoisomerase II," Proc. Natl. Acad. Sci., 86:5497–5501, 1989.

Spruck et al., "P16 gene in uncultured cells," Nature, 370:183–184, 1994.

Stanbridge, "Human tumor suppressor genes," Annu. Rev. Genet., 24:615–657, 1990.

Tangle et al., "Magnetic bead capture of expressed sequences encoded within large genomic segments," Nature, 361:751–753, 1993.

Tocharoentanaphol et al., "Multicolor fluorescence in situ hybridization on metaphase chromosomes and interphase Halo-preparations using cosmid and YAC clones for the simultaneous high resolution mapping of deletions in the dystrophin gene," Hum. Genet., 92:229–235, 1994.

Tompson et al., "p53 allele loss, mutations and expression in breast cancer and their relationship to clinicopathologic parameters," Int. J. Cancer, 50:528–532, 1992.

Vogelstein et al., "Genetic alterations during colorectal development," New Engl. J. Med., 319:525–528, 1989.

Weaver-Feldhaus et al., Proc. Natl. Acad. Sci. USA, 91:7563–7567, 1994.

Wolf et al., Compu. Appl. Biosci., 4(1):187–91, 1988.

Xiong et al., "p21 is a universal inhibitor of cyclin kinases," Nature (London), 366:707–710, 1993.

Xu et al., "Intraocular tumor formation of RB reconstituted retinoblastoma cells," Cancer Res., 51:4481–4485, 1985.

Yamada et al., "Multiple chromosomes carrying tumor suppressor activity for a uterine endometrial carcinoma cell line identified by microcell mediated chromosome transfer," Oncogene, 5:1141–1147, 1990.

What is claimed is:

1. An isolated polynucleotide comprising a sequence region that encodes a polypeptide comprising the amino acid sequence of SEQ ID NO:2.

2. The isolated polynucleotide of claim 1, wherein said sequence region comprises at least 21 contiguous nucleotides from nucleotide 122 to nucleotide 970 of SEQ ID NO:1.

3. The isolated polynucleotide of claim 2, wherein said sequence region comprises at least 30 contiguous nucleotides from nucleotide 122 to nucleotide 970 of SEQ ID NO:1.

4. The isolated polynucleotide of claim 3, wherein said sequence region comprises at least 40 contiguous nucleotides from nucleotide 122 to nucleotide 970 of SEQ ID NO:1.

5. The isolated polynucleotide of claim 4, wherein said sequence region comprises the sequence from nucleotide 122 to nucleotide 970 of SEQ ID NO:1.

6. The isolated polynucleotide of claim 4, comprising the sequence of SEQ ID NO:1.

7. The isolated polynucleotide of claim 1, wherein said nucleotide is from about 849 to about 1,000 basepairs in length.

8. The isolated poluynuicleotide of claim 1, wherein said sequence region that encodes a polypeptide comprising the amino acid sequence of SEQ ID NO:2 is operably positioned under the control of a promoter.

9. The isolated polynucleotide of claim 1, wherein said sequence region that encodes a polypeptide comprising the amino acid sequence of SEQ ID NO:2 is operatively linked to a second coding region that encodes a selected peptide or polypeptide, said nucleotide encoding a methylthioadenosine phosphorylase fusion peptide or polypeptide.

10. The isolated polynucleotide of claim 1, comprised within a vector.

11. The isolated polynucleotide of claim 1, comprised within a host cell.

12. A vector comprising a nucleotide sequence that encodes a mammalian methylthioadenosine phosphorylase polypeptide comprising the amino acid sequence of SEQ ID NO:2.

13. The vector of claim 12, wherein said nucleotide sequence comprises the nucleic acid sequence of SEQ ID NO:1.

14. The vector of claim 12, comprised within a host cell.

15. A host cell comprising a nucleotide sequence not normally found within the cell and that encodes a mammalian methylthioadenosine phosphorylase polypeptide comprising the amino acid sequence of SEQ ID NO:2.

16. The host cell of claim 15, wherein said nucleotide sequence comprises the nucleic acid sequence of from about nucleotide 122 to nucleotide 970 of SEQ ID NO:1.

17. The host cell of claim 15, wherein said cell is a prokaryotic host cell.

18. The host cell of claim 15, wherein said cell is a eukaryotic host cell.

* * * * *

UNITED STATES PATENT AND TRADEMARK OFFICE
CERTIFICATE OF CORRECTION

PATENT NO. : 6,870,037 B1
DATED : March 22, 2005
INVENTOR(S) : Olufunmilayo I. Olopade It is certified that error appears in the above-identified patent and that said Letters Patent is hereby corrected as shown below:

Title page,
Item [57], ABSTRACT,
Line 2, please delete "methythlioadenosine" and insert -- methylthioadenosine --.

Column 78,
Line 66, please delete "poluynuicleotide" and insert -- polynucleotide --.

Signed and Sealed this

Twelfth Day of July, 2005

JON W. DUDAS
*Director of the United States Patent and Trademark Office*

UNITED STATES PATENT AND TRADEMARK OFFICE
CERTIFICATE OF CORRECTION

PATENT NO. : 6,870,037 B1
APPLICATION NO. : 08/674311
DATED : March 22, 2005
INVENTOR(S) : Olufunmilayo I. Olopade Page 1 of 1

It is certified that error appears in the above-identified patent and that said Letters Patent is hereby corrected as shown below:

Title page, at item (60), please delete "July 2, 1995" and insert therefor --July 3, 1995--.

Signed and Sealed this

Thirtieth Day of October, 2007

JON W. DUDAS
*Director of the United States Patent and Trademark Office*